(12) United States Patent
Carter et al.

(10) Patent No.: US 11,730,625 B2
(45) Date of Patent: Aug. 22, 2023

(54) OPHTHALMIC CUTTING INSTRUMENTS HAVING INTEGRATED ASPIRATION PUMP

(71) Applicant: Carl Zeiss Meditec Cataract Technology Inc., Reno, NV (US)

(72) Inventors: Brett Carter, Reno, NV (US); Scott Chamness, Reno, NV (US); Luke W. Clauson, Reno, NV (US); Michael Schaller, Reno, NV (US)

(73) Assignee: Carl Zeiss Meditec Cataract Technology Inc., Reno, NV (US)

( * ) Notice: Subject to any disclaimer, the term of this patent is extended or adjusted under 35 U.S.C. 154(b) by 368 days.

(21) Appl. No.: 16/875,426

(22) Filed: May 15, 2020

(65) Prior Publication Data

US 2020/0360185 A1  Nov. 19, 2020

Related U.S. Application Data

(60) Provisional application No. 62/872,898, filed on Jul. 11, 2019, provisional application No. 62/868,688, (Continued)

(51) Int. Cl.
*A61F 9/007* (2006.01)
*A61M 1/00* (2006.01)

(52) U.S. Cl.
CPC ...... *A61F 9/00736* (2013.01); *A61F 9/00754* (2013.01); *A61M 1/743* (2021.05); *A61M 1/774* (2021.05); *A61M 2210/0612* (2013.01)

(58) Field of Classification Search
CPC ............ A61F 9/00754; A61F 9/00736; A61F 9/00763; A61F 9/00745; A61F 2250/0093;
(Continued)

(56) References Cited

U.S. PATENT DOCUMENTS 1,833,687 A   11/1931  Neivert
2,947,470 A    8/1960  Ruben et al.
(Continued)

FOREIGN PATENT DOCUMENTS

CN      1242824 A    1/2000
CN      1494443 A    5/2004
(Continued)

OTHER PUBLICATIONS

Vibration, First recorded in 1645-1655, Dictionary.com (Year: 1645).*
(Continued)

*Primary Examiner* — Kai H Weng
*Assistant Examiner* — Brandon W. Levy
(74) *Attorney, Agent, or Firm* — Mintz Levin Cohn Ferris Glovsky and Popeo, P.C.

(57) ABSTRACT

A device for performing an ophthalmic procedure in an eye including a hand-held portion; an elongate member extending from a distal end region of the hand-held portion; and an aspiration pump within the hand-held portion. The elongate member includes a lumen and an opening near a distal end region of the elongate member. The aspiration pump is in fluid communication with the opening of the elongate member. The aspiration pump includes a camshaft extending along a longitudinal axis and having a plurality of lobed cams; tubing extending parallel to the longitudinal axis; and a plurality of cam followers driven by the cams of the camshaft to move in a plane perpendicular to the longitudinal axis to sequentially compress the tubing. Related devices, systems, methods are provided.

88 Claims, 25 Drawing Sheets

Related U.S. Application Data filed on Jun. 28, 2019, provisional application No. 62/849,302, filed on May 17, 2019.

(58) Field of Classification Search
CPC .. A61F 2009/00889; A61F 2009/0087; A61M 1/741; A61M 1/743; A61M 2210/0612; A61M 1/774; A61M 2202/0468; A61M 2202/09; A61M 2205/0294; A61M 2205/103; A61M 2205/3344; A61M 2205/3553; A61M 2205/3584; A61M 2205/3592; A61M 2205/505; A61M 2205/52; A61M 2205/581; A61M 2205/582; A61M 2205/583; A61M 2205/8206; A61M 2205/8243; A61M 2205/8262; A61M 2205/8293; A61M 2209/06; A61M 1/80; A61M 2205/106; A61M 16/0463; A61M 1/76; A61M 1/84; A61M 1/0023; A61B 2217/005; A61B 2217/007; A61B 17/32; A61B 17/32056; A61B 17/3203; A61B 18/082; F04B 43/086; Y10T 29/4924; Y10T 74/2101
See application file for complete search history.

(56) References Cited

U.S. PATENT DOCUMENTS

| | | |
|---|---|---|
| 3,183,849 A | 5/1965 | Raymond |
| 3,589,363 A | 6/1971 | Banko et al. |
| 3,957,052 A | 5/1976 | Topham |
| 3,990,452 A | 11/1976 | Murry et al. |
| 4,368,734 A | 1/1983 | Banko |
| 4,493,706 A | 1/1985 | Borsanyi et al. |
| 4,508,532 A | 4/1985 | Drews et al. |
| 4,643,187 A | 2/1987 | Okada |
| 4,705,500 A | 11/1987 | Reimels et al. |
| 4,732,150 A | 3/1988 | Keener Jr. |
| 4,764,165 A | 8/1988 | Reimels et al. |
| 4,854,825 A | 8/1989 | Bez et al. |
| 4,891,044 A | 1/1990 | Mitchell |
| 4,908,015 A | 3/1990 | Anis |
| 4,921,477 A | 5/1990 | Davis |
| 5,146,921 A | 9/1992 | Terwilliger et al. |
| 5,222,959 A | 6/1993 | Anis |
| 5,275,607 A | 1/1994 | Lo et al. |
| 5,279,547 A | 1/1994 | Costin |
| 5,337,780 A * | 8/1994 | Kee ................ A61M 16/0463 137/557 |
| 5,350,390 A | 9/1994 | Sher |
| 5,437,678 A | 8/1995 | Sorensen |
| 5,651,783 A | 7/1997 | Reynard |
| 5,676,649 A | 10/1997 | Boukhny et al. |
| 5,693,062 A | 12/1997 | Stegmann et al. |
| 5,755,561 A | 5/1998 | Couillard et al. |
| 5,788,667 A * | 8/1998 | Stoller ................ A61M 1/0023 606/167 |
| 5,788,679 A | 8/1998 | Gravlee, Jr. |
| 5,807,401 A | 9/1998 | Grieshaber et al. |
| 5,833,643 A | 11/1998 | Ross et al. |
| 5,843,071 A | 12/1998 | Bath |
| 5,891,153 A | 4/1999 | Peterson |
| 5,911,699 A | 6/1999 | Anis et al. |
| 5,938,677 A | 8/1999 | Boukhny et al. |
| 6,004,284 A | 12/1999 | Sussman et al. |
| 6,013,049 A | 1/2000 | Rockley et al. |
| 6,059,765 A | 5/2000 | Cole et al. |
| 6,074,396 A | 6/2000 | Geuder |
| 6,117,149 A | 9/2000 | Sorensen et al. |
| 6,132,436 A | 10/2000 | Portney |
| 6,165,190 A | 12/2000 | Nguyen |
| 6,183,433 B1 | 2/2001 | Bays |
| 6,186,148 B1 | 2/2001 | Okada |
| 6,241,700 B1 | 6/2001 | Leukanech |
| 6,254,587 B1 | 7/2001 | Christ et al. |
| 6,258,111 B1 | 7/2001 | Ross et al. |
| 6,299,591 B1 | 10/2001 | Banko |
| 6,319,222 B1 | 11/2001 | Andrew et al. |
| 6,322,557 B1 | 11/2001 | Nikolaevich et al. |
| 6,328,747 B1 | 12/2001 | Nun |
| 6,398,754 B1 | 6/2002 | Sutton et al. |
| 6,428,508 B1 | 8/2002 | Ross |
| 6,485,499 B1 | 11/2002 | Oberkamp et al. |
| 6,506,176 B1 | 1/2003 | Mittelstein et al. |
| 6,520,929 B2 | 2/2003 | Zaleski |
| 6,520,955 B2 | 2/2003 | Reynard |
| 6,527,766 B1 | 3/2003 | Bair |
| 6,544,254 B1 | 4/2003 | Bath |
| 6,589,201 B1 | 7/2003 | Sussman et al. |
| 6,592,541 B1 | 7/2003 | Kurwa |
| 6,605,054 B2 | 8/2003 | Rockley |
| 6,623,477 B1 | 9/2003 | Elbrecht et al. |
| 6,852,092 B2 | 2/2005 | Kadziauskas et al. |
| 6,860,868 B1 | 3/2005 | Sussman et al. |
| 6,939,317 B2 | 9/2005 | Zacharias |
| 6,939,341 B2 | 9/2005 | Vijfvinkel |
| 7,041,078 B1 | 5/2006 | Peyman |
| 7,083,589 B2 | 8/2006 | Banko et al. |
| 7,083,591 B2 | 8/2006 | Cionni |
| 7,141,047 B2 | 11/2006 | John |
| 7,172,601 B2 | 2/2007 | Ben-Nun |
| 7,182,759 B2 | 2/2007 | Kadziauskas et al. |
| 7,204,820 B2 | 4/2007 | Akahoshi |
| 7,285,107 B1 | 10/2007 | Charles |
| 7,303,566 B2 | 12/2007 | Kishimoto et al. |
| 7,544,178 B2 | 6/2009 | Kadziauskas et al. |
| 7,549,972 B2 | 6/2009 | Luloh et al. |
| 7,588,553 B2 | 9/2009 | Dewey |
| 7,845,235 B2 | 12/2010 | Sandu et al. |
| 7,846,126 B2 | 12/2010 | Steen et al. |
| 7,857,794 B2 | 12/2010 | Dimalanta et al. |
| 7,876,025 B2 | 1/2011 | Ma et al. |
| 7,955,060 B2 | 6/2011 | Gottschalk |
| 7,967,775 B2 | 6/2011 | Hong |
| 8,070,711 B2 | 12/2011 | Bassinger et al. |
| 8,080,029 B2 | 12/2011 | Charles |
| 8,142,388 B2 | 3/2012 | Gomez |
| 8,187,293 B2 | 5/2012 | Kirchhevel |
| 8,216,246 B2 | 7/2012 | Luloh et al. |
| 8,246,644 B2 | 8/2012 | Rockley et al. |
| 8,287,484 B2 | 10/2012 | Rockley |
| 8,298,253 B2 | 10/2012 | Charles |
| 8,308,735 B2 | 11/2012 | Dimalanta |
| 8,317,739 B2 | 11/2012 | Kuebler |
| 8,376,983 B2 | 2/2013 | Ross et al. |
| 8,423,126 B2 | 4/2013 | Mackool |
| 8,475,480 B2 | 7/2013 | Mackool |
| 8,545,462 B2 | 10/2013 | Ghannoum |
| 8,771,301 B2 | 7/2014 | Boukhny et al. |
| 8,784,361 B2 | 7/2014 | Lane |
| 8,801,653 B2 | 8/2014 | Maaskamp et al. |
| 8,852,139 B2 | 10/2014 | King et al. |
| 8,876,745 B2 | 11/2014 | Escaf |
| 8,876,747 B2 | 11/2014 | Kadziauskas et al. |
| 8,939,927 B2 | 1/2015 | Sorensen et al. |
| 8,986,290 B2 | 3/2015 | Patton |
| 9,050,171 B2 | 6/2015 | Foster |
| 9,144,517 B2 | 9/2015 | Kuebler et al. |
| 9,259,597 B2 | 2/2016 | Romano et al. |
| 9,351,871 B2 | 5/2016 | Ghannoum et al. |
| 9,370,611 B2 | 6/2016 | Ross et al. |
| 9,387,122 B2 | 7/2016 | Mackool |
| 9,402,766 B2 | 8/2016 | Akahoshi et al. |
| 9,433,725 B2 | 9/2016 | Schaller et al. |
| 9,439,807 B2 | 9/2016 | Koplin |
| 9,445,943 B2 | 9/2016 | Wilson et al. |
| 9,486,359 B2 | 11/2016 | Hauger et al. |
| 9,486,360 B2 | 11/2016 | Chon |
| 9,498,377 B2 | 11/2016 | McCary et al. |
| 9,498,378 B2 | 11/2016 | McDonell |
| 9,504,604 B2 | 11/2016 | Alvarez |
| 9,561,129 B2 | 2/2017 | Ross et al. |
| 9,566,188 B2 | 2/2017 | Raney et al. |

(56) References Cited

U.S. PATENT DOCUMENTS

| | | |
|---|---|---|
| 9,592,156 B2 | 3/2017 | Huang |
| 9,629,747 B2 | 4/2017 | Clauson et al. |
| 9,693,896 B2 | 7/2017 | Sussman |
| 9,724,238 B2 | 8/2017 | Heitel |
| 9,731,065 B2 | 8/2017 | Bourne et al. |
| 9,750,639 B2 | 9/2017 | Barnes et al. |
| 9,775,743 B2 | 10/2017 | Clauson et al. |
| 9,827,142 B2 | 11/2017 | Sasazaki et al. |
| 9,839,738 B2 | 12/2017 | Beauvais et al. |
| 9,861,522 B2 | 1/2018 | Sorensen et al. |
| 9,867,635 B2 | 1/2018 | Alvarez et al. |
| 9,878,075 B2 | 1/2018 | Sussman et al. |
| 9,889,247 B2 | 2/2018 | Akahoshi |
| 9,913,752 B2 | 3/2018 | Hauger |
| 10,231,870 B2 | 3/2019 | Clauson et al. |
| 10,251,782 B2 | 4/2019 | Farley |
| 10,278,861 B2 | 5/2019 | Bourne |
| 10,294,934 B2 | 5/2019 | Bourne et al. |
| 10,603,213 B2 | 3/2020 | Clauson et al. |
| 10,639,197 B2 | 5/2020 | Lopez et al. |
| 11,045,354 B2 | 6/2021 | Sorensen et al. |
| 11,147,709 B2 | 10/2021 | Kahook et al. |
| 2002/0052617 A1 | 5/2002 | Anis et al. |
| 2002/0099400 A1 | 7/2002 | Wolf et al. |
| 2002/0151835 A1 | 10/2002 | Ross |
| 2003/0004455 A1 | 1/2003 | Kadziauskas et al. |
| 2003/0055387 A1 | 3/2003 | Sutton et al. |
| 2003/0109867 A1 | 6/2003 | Gluche et al. |
| 2004/0010284 A1 | 1/2004 | Maloof et al. |
| 2004/0049217 A1 | 3/2004 | Ross et al. |
| 2004/0082902 A1 | 4/2004 | Kadziauskas et al. |
| 2004/0092800 A1 | 5/2004 | MacKool |
| 2004/0099247 A1 | 5/2004 | Nelson |
| 2004/0153093 A1 | 8/2004 | Donovan |
| 2005/0113741 A1 | 5/2005 | Huang et al. |
| 2005/0234441 A1 | 10/2005 | Bisch et al. |
| 2005/0234473 A1 | 10/2005 | Zacharias |
| 2006/0135974 A1 | 6/2006 | Perkins |
| 2006/0253056 A1 | 11/2006 | Kadziauskas et al. |
| 2007/0060926 A1 | 3/2007 | Escaf |
| 2007/0260173 A1 | 11/2007 | Boukhny et al. |
| 2008/0188792 A1 | 8/2008 | Barrett |
| 2008/0300531 A1 | 12/2008 | Gills, Jr. |
| 2009/0048607 A1 | 2/2009 | Rockley |
| 2009/0054904 A1 | 2/2009 | Holmen |
| 2009/0137993 A1 | 5/2009 | Kurtz |
| 2009/0149840 A1 | 6/2009 | Kurtz |
| 2009/0156985 A1 | 6/2009 | Hottmann et al. |
| 2009/0171242 A1 | 7/2009 | Hibner |
| 2010/0030134 A1* | 2/2010 | Fitzgerald ............... A61M 1/74 604/35 |
| 2010/0191178 A1 | 7/2010 | Ross et al. |
| 2010/0286651 A1 | 11/2010 | Sorensen |
| 2010/0292631 A1 | 11/2010 | Holden |
| 2010/0312170 A1 | 12/2010 | Maaskamp et al. |
| 2010/0331911 A1 | 12/2010 | Kovalcheck et al. |
| 2011/0015562 A1 | 1/2011 | Akahoshi |
| 2011/0054384 A1 | 3/2011 | Brown |
| 2011/0112466 A1 | 5/2011 | Dimalanta |
| 2011/0137231 A1 | 6/2011 | Sorensen et al. |
| 2011/0144638 A1 | 6/2011 | Heeren et al. |
| 2011/0290854 A1* | 12/2011 | Timm ............... A61B 17/00234 227/178.1 |
| 2011/0295192 A1 | 12/2011 | Geuder |
| 2012/0004595 A1 | 1/2012 | Dubois et al. |
| 2012/0022434 A1 | 1/2012 | Lue et al. |
| 2012/0041358 A1 | 2/2012 | Mann et al. |
| 2012/0072197 A1 | 3/2012 | Ovchinnikov |
| 2012/0078181 A1* | 3/2012 | Smith ............... H02J 7/0029 604/404 |
| 2012/0089080 A1 | 4/2012 | Ross et al. |
| 2012/0157908 A1 | 6/2012 | Underwood et al. |
| 2012/0158030 A1 | 6/2012 | Underwood et al. |
| 2012/0165734 A1 | 6/2012 | Auld et al. |
| 2012/0184892 A1 | 7/2012 | Bigler et al. |
| 2012/0259320 A1 | 10/2012 | Loesel et al. |
| 2013/0043023 A1 | 2/2013 | Hallundbaek |
| 2013/0060210 A1 | 3/2013 | Ross et al. |
| 2013/0231605 A1 | 9/2013 | Walter |
| 2013/0282020 A1 | 10/2013 | Hunter |
| 2013/0317417 A1 | 11/2013 | Claus et al. |
| 2014/0005681 A1 | 1/2014 | Gee et al. |
| 2014/0012186 A1 | 1/2014 | Thyzel |
| 2014/0052113 A1 | 2/2014 | Kuehnert et al. |
| 2014/0074013 A1 | 3/2014 | McCary et al. |
| 2014/0081151 A1 | 3/2014 | Saimovici |
| 2014/0081266 A1 | 3/2014 | Dubois et al. |
| 2014/0114335 A1 | 4/2014 | Banko |
| 2014/0163455 A1 | 6/2014 | Wilson et al. |
| 2014/0194860 A1 | 7/2014 | Dick et al. |
| 2014/0236163 A1 | 8/2014 | Olson et al. |
| 2014/0257258 A1 | 9/2014 | Kurtz |
| 2014/0271251 A1 | 9/2014 | Bourne et al. |
| 2014/0309649 A1 | 10/2014 | Alvarez et al. |
| 2014/0358155 A1 | 12/2014 | DeBoer et al. |
| 2014/0360494 A1 | 12/2014 | Herskovic |
| 2014/0364885 A1 | 12/2014 | Wells et al. |
| 2015/0005753 A1 | 1/2015 | Walter |
| 2015/0025450 A1 | 1/2015 | King et al. |
| 2015/0038894 A1 | 2/2015 | Urich et al. |
| 2015/0045806 A1 | 2/2015 | Urich et al. |
| 2015/0105791 A1 | 4/2015 | Truckai |
| 2015/0125328 A1* | 5/2015 | Bourne ............... F04B 43/086 417/477.4 |
| 2015/0141801 A1 | 5/2015 | Jean et al. |
| 2015/0144514 A1 | 5/2015 | Brennan et al. |
| 2015/0148615 A1 | 5/2015 | Brennan et al. |
| 2015/0196426 A1 | 7/2015 | Kuebler et al. |
| 2015/0202081 A1 | 7/2015 | Eichler |
| 2015/0216722 A1 | 8/2015 | Choate |
| 2015/0216728 A1 | 8/2015 | Keller |
| 2015/0257927 A1 | 9/2015 | Olson |
| 2015/0297405 A1 | 10/2015 | Bourne et al. |
| 2015/0297407 A1 | 10/2015 | Saimovici |
| 2015/0306286 A1 | 10/2015 | Ross et al. |
| 2015/0328047 A1 | 11/2015 | Falck, Jr. |
| 2015/0359672 A1 | 12/2015 | Van Valen et al. |
| 2016/0022489 A1 | 1/2016 | Hartstra |
| 2016/0058614 A1 | 3/2016 | Ross et al. |
| 2016/0067091 A1 | 3/2016 | Wells et al. |
| 2016/0074220 A1 | 3/2016 | Ianchulev et al. |
| 2016/0089268 A1 | 3/2016 | Chon et al. |
| 2016/0095749 A1 | 4/2016 | Raney et al. |
| 2016/0095750 A1 | 4/2016 | Raney et al. |
| 2016/0106580 A1 | 4/2016 | Banko |
| 2016/0106893 A1 | 4/2016 | Zacharias |
| 2016/0128869 A1 | 5/2016 | Zacharias |
| 2016/0135991 A1* | 5/2016 | Farley ............... A61F 9/00763 606/171 |
| 2016/0143780 A1 | 5/2016 | Gunn |
| 2016/0166432 A1 | 6/2016 | Kahook et al. |
| 2016/0175578 A1 | 6/2016 | Roholt |
| 2016/0220807 A1* | 8/2016 | Bono ............... A61M 1/741 |
| 2016/0346121 A1 | 12/2016 | Ianchulev et al. |
| 2017/0007451 A1 | 1/2017 | Depenbusch |
| 2017/0007452 A1 | 1/2017 | Depenbusch |
| 2017/0020728 A1 | 1/2017 | McDonell |
| 2017/0027750 A1 | 2/2017 | Wiley |
| 2017/0087013 A1 | 3/2017 | Prats et al. |
| 2017/0151091 A1 | 6/2017 | Bourne et al. |
| 2017/0151378 A1 | 6/2017 | Raney et al. |
| 2017/0211959 A1 | 7/2017 | Adler et al. |
| 2017/0312125 A1 | 11/2017 | Clauson et al. |
| 2017/0333252 A1 | 11/2017 | Biancalana et al. |
| 2017/0360607 A1 | 12/2017 | Price et al. |
| 2017/0367885 A1 | 12/2017 | Bourne |
| 2018/0028360 A1 | 2/2018 | Kozawa |
| 2018/0036171 A1 | 2/2018 | Clauson et al. |
| 2018/0049920 A1 | 2/2018 | Charles |
| 2018/0049921 A1 | 2/2018 | Sorensen et al. |
| 2018/0058438 A1 | 3/2018 | Ochoa |
| 2018/0064578 A1 | 3/2018 | Clauson et al. |
| 2018/0318132 A1 | 11/2018 | Clauson et al. |
| 2018/0318133 A1 | 11/2018 | Clauson et al. |

(56) References Cited

U.S. PATENT DOCUMENTS

| | | |
|---|---|---|
| 2019/0015252 A1 | 1/2019 | Lake et al. |
| 2019/0041665 A1 | 2/2019 | Widman et al. |
| 2019/0099292 A1 | 4/2019 | Strayer et al. |
| 2019/0133825 A1 | 5/2019 | Clauson et al. |
| 2019/0151149 A1 | 5/2019 | Clauson et al. |
| 2019/0183679 A1 | 6/2019 | Sawicz |
| 2019/0183681 A1 | 6/2019 | Schaller et al. |
| 2019/0254872 A1 | 8/2019 | Clauson et al. |
| 2019/0269557 A1 | 9/2019 | Clauson et al. |
| 2019/0282402 A1 | 9/2019 | Clauson et al. |
| 2019/0321223 A1 | 10/2019 | Chamness et al. |
| 2019/0365567 A1 | 12/2019 | Balkenbush et al. |
| 2019/0388272 A1 | 12/2019 | Clauson et al. |
| 2020/0016001 A1 | 1/2020 | McDonell et al. |
| 2020/0022841 A1 | 1/2020 | Chamness et al. |
| 2020/0060875 A1 | 2/2020 | Clauson et al. |
| 2020/0197222 A1 | 6/2020 | Clauson et al. |
| 2020/0289319 A1 | 9/2020 | Carter et al. |
| 2020/0352784 A1 | 11/2020 | Kahook et al. |
| 2020/0383833 A1 | 12/2020 | Schaller |
| 2021/0100937 A1 | 4/2021 | Bourne et al. |
| 2022/0151831 A1 | 5/2022 | Peterson |
| 2022/0233353 A1 | 7/2022 | Carter et al. |

FOREIGN PATENT DOCUMENTS

| | | |
|---|---|---|
| CN | 103671079 A | 3/2014 |
| CN | 108024854 A | 5/2018 |
| DE | 10 2007 031722 A1 | 1/2009 |
| DE | 102007040290 B4 | 7/2019 |
| EP | 1832259 B1 | 6/2009 |
| EP | 1556099 B1 | 7/2013 |
| EP | 2168540 B1 | 4/2015 |
| EP | 2 094 173 B1 | 3/2016 |
| EP | 1735030 B1 | 8/2016 |
| EP | 2 892 438 B1 | 10/2018 |
| GB | 1304324 A | 1/1973 |
| GB | 2018601 A | 10/1979 |
| JP | H0779826 B2 | 8/1995 |
| JP | 2018035761 A | 3/2018 |
| JP | 6654763 B2 | 2/2020 |
| SU | 728852 A1 | 4/1980 |
| WO | WO-2006/119557 A1 | 11/2006 |
| WO | WO-2013/039742 A2 | 3/2013 |
| WO | WO-2014/039093 A1 | 3/2014 |
| WO | WO-2015/161149 A1 | 10/2015 |
| WO | WO-2018/081295 A1 | 5/2018 |
| WO | WO-2018/217579 A1 | 11/2018 |

OTHER PUBLICATIONS

U.S. Appl. No. 15/970,439, filed May 3, 2018, US 2018-0318132.
U.S. Appl. No. 16/221,239, filed Dec. 14, 2018, US 2019-0183681.
U.S. Appl. No. 16/257,533, filed Jan. 25, 2019, US 2019-0151149.
U.S. Appl. No. 16/404,252, filed May 6, 2019, US 2019-0254872.
U.S. Appl. No. 16/431,560, filed Jun. 4, 2019, US 2019-0365567.
U.S. Appl. No. 16/436,648, filed Jun. 10, 2019, US 2019-0321223.
U.S. Appl. No. 16/577,418, filed Sep. 20, 2019, US 2020-0022841.
U.S. Appl. No. 16/667,030, filed Oct. 29, 2019, US 2020-0060875.
U.S. Appl. No. 16/690,881, filed Nov. 21, 2019, US 2020-0197222.
U.S. Appl. No. 16/811,786, filed Mar. 6, 2020, US 2020-0306083.
U.S. Appl. No. 16/875,421, filed May 15, 2020, US 2020-0383833.
U.S. Appl. No. 17/177,017, filed Feb. 16, 2021, US 2021-0161712.
U.S. Appl. No. 17/570,094, filed Jan. 6, 2022, US 2022-0233353.
U.S. Appl. No. 16/345,182, filed Apr. 25, 2019, US 2019-0282402.

\* cited by examiner

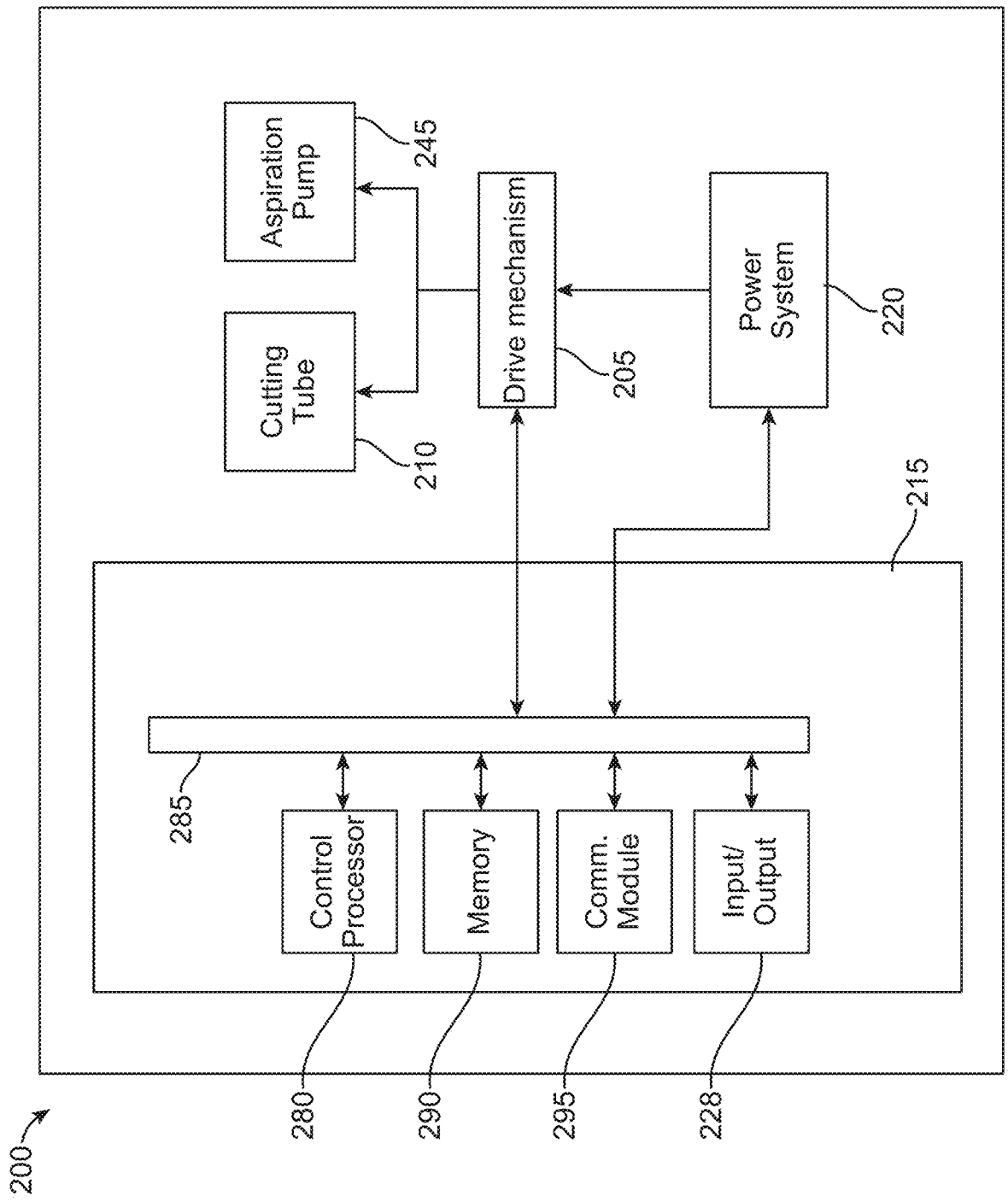

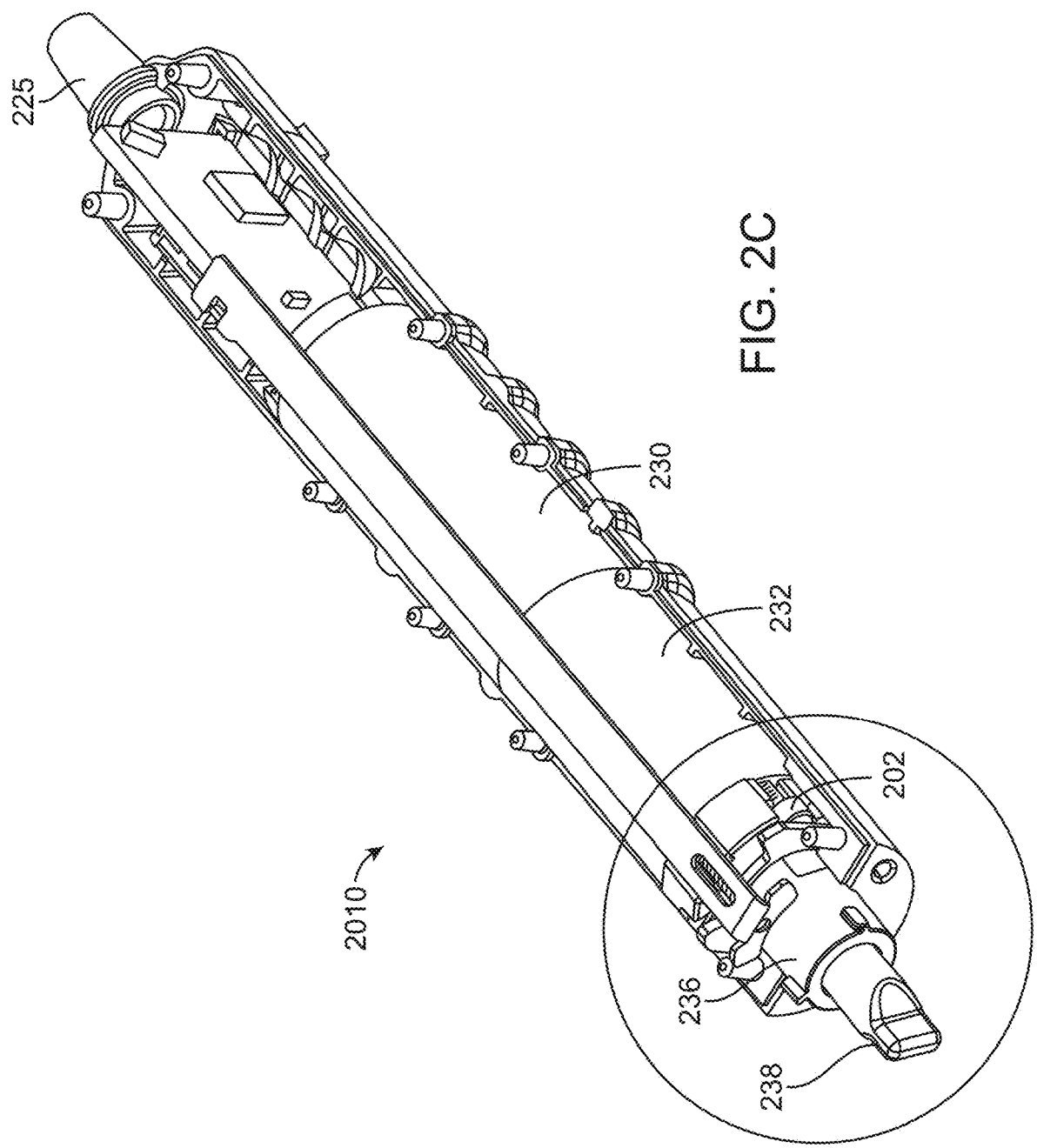

OPHTHALMIC CUTTING INSTRUMENTS HAVING INTEGRATED ASPIRATION PUMP

CROSS-REFERENCE TO RELATED APPLICATIONS

This application claims the benefit of priority under 35 U.S.C. § 119(e) to U.S. Provisional Patent Application Ser. No. 62/849,302, filed May 17, 2019, U.S. Provisional Patent Application Ser. No. 62/868,688 filed Jun. 28, 2019, and U.S. Provisional Patent Application Ser. No. 62/872,898, filed Jul. 11, 2019. The disclosures of the provisional applications are hereby incorporated by reference in their entireties.

FIELD

The present technology relates generally to ophthalmic microsurgical tools and systems, in particular, ophthalmic cutting tools having a reusable durable driver portion configured to operatively couple with different disposable working portions in an interchangeable manner.

BACKGROUND

Certain types of conventional ophthalmic surgery require breaking up lenticular tissue and intraocular objects, such as the intraocular lens or vitreous so that they can be extracted from the eye. For example, extraction of lenses for cataract surgery is one of the most common surgical procedures with more than 3 million cases performed annually in the United States alone. During cataract surgery, a commonly used method for lens extraction is phacoemulsification, which uses ultrasonic energy to emulsify the lens and aspiration to remove the lens emulsate from the eye. Other methods of lens fragmentation and extraction may include the use of instruments such as hooks, knives, or lasers to fragment the lens into pieces small enough to be extracted through an incision in the cornea in an ab interno approach. Intraocular, ab interno fragmentation of the lenticular tissue is important in cataract surgery in order to allow removal of cataracts from ocular incisions that are typically not exceeding 2.8-3.0 mm.

Typical phacoemulsification systems include a console in operative communication with a phacoemulsification hand piece that provides the control of the electronics of the hand piece, aspiration, and irrigation. During typical phacoemulsification procedures, the phaco tip is inserted into the anterior segment of the eye through a small incision in the cornea. The phaco tip is brought into contact with the lens of the eye so that the oscillating phaco top emulsifies the lens. The emulsate is then aspirated through the lumen of the phaco tip.

A challenge associated with conventional phaco devices and other devices using a remote vacuum source is that the suction lines are quite long and flexible contributing to the fluidic system compliance. Phacoemulsification machines incorporate remote pumps, typically a peristaltic pump, venturi pump, or a combination of both, to provide fluid management during a procedure. Peristaltic pumps function by sequentially compressing a segment of tubing between a plate or rollers to move an amount of fluid or tissue away from the operative site. The plates or rollers are arranged so that at any time at least one is occluding the tubing. A transient pressure increase is experienced in the tubing. Peristaltic pumps can cause mild flow fluctuations as the rollers compress the tube. Turbulence can cause posterior capsule bounce and iris flutter, which are undesirable movements. Long, compliant suction lines containing compressible material affects the responsive times at the tip when suction is turned on and off. These remote pumps suffer from post-occlusion surge.

In the context of cataract surgery, vitrectomy is used when a complication occurs during lens removal. For example, phacoemulsification has a risk of penetrating the posterior lens capsule leading to inadvertent prolapse of vitreous into the anterior segment. Vitrectomy is essentially a rescue procedure performed during cataract surgery. The goals of anterior vitrectomy are to remove the vitreous from the anterior chamber, to clear vitreous from entry incisions, and to allow the IOL to be placed.

Vitreous has an unpredictable flow behavior that is difficult to characterize due to its semi-solid structure. Vitreous is composed of mostly water, but also collagen fiber and hyaluronic acid. Vitreous requires cutting before going through the probe. Chopped vitreous has a lower viscosity than intact gel-like vitreous. Small bite sizes pieces are preferred to improve aspiration and removal of vitreous. Most commercially available anterior vitrectors are designed for coaxial irrigation and vitreous cutting. Local turbulent flow and vitreous volume expansion from hydration can be an issue with coaxial irrigation and cutting systems. Irrigation can also be performed with a bimanual approach separating the vitrector from the irrigation. Vitrectors are typically inserted through limbal incisions although vitrector can also be inserted through a stab incision made 3 mm posterior to the limbus through the pars plana using a microvitreoretinal blade. Low level cutting (300 cuts per minute (cpm)) and aspiration can be used to remove the lens fragments prior to initiation of the vitreous removal. For vitreous removal, the cut rate is set high (500-600 cpm), with low to moderate aspiration. The high cut speed for vitreous removal causes the vitreous to flow continuously into the cutter. The vitrector is placed through the capsular tear just below the capsule with the aspiration port facing up toward the cornea. The vitreous is removed to a level just posterior to the capsule.

SUMMARY

According to a first aspect, disclosed is a device for performing an ophthalmic procedure in an eye. The device includes a hand-held portion and an elongate member extending from a distal end region of the hand-held portion. The elongate member includes a lumen and an opening near a distal end region of the elongate member. The device includes an aspiration pump within the hand-held portion in fluid communication with the opening of the elongate member. The aspiration pump includes a camshaft extending along a longitudinal axis and having a plurality of lobed cams; tubing extending parallel to the longitudinal axis; and a plurality of cam followers driven by the cams of the camshaft to move in a plane perpendicular to the longitudinal axis to compress the tubing sequentially.

The tubing can include a proximal flow path that splits into a pair of peripheral tubes positioned on either side of the camshaft, the pair of peripheral tubes combine distal to a pumping manifold to form a distal flow path in fluid communication with the lumen of the elongate member. The plurality of cam followers sequentially compressing the pair of peripheral tubes can create a substantially non-pulsatile aspiration. The substantially non-pulsatile aspiration can be less than about 3 cc/minute. The substantially non-pulsatile aspiration can be between 3 cc/minute to about 10 cc/minute. The substantially non-pulsatile aspiration can be greater than 10 cc/minute up to about 25 cc/minute.

The elongate member can be movable in a reciprocating motion relative to the hand-held portion. The elongate member can be configured for lens fragmentation, lens emulsification, or anterior vitrectomy. The elongate member can have a maximum cross-sectional diameter of about 1.25 mm. The elongate member can have a maximum cross-sectional diameter that is no more than about 3 mm. The elongate member can be a vitrectomy probe that is between 20 gauge and 27 gauge. The elongate member can be configured to slide reciprocally within an outer tube that is fixedly coupled within an interior of the hand-held portion. A distal tip of the elongate member can form a cutting edge. The outer tube can include an opening through a side wall. The elongate member further can include a side opening near its distal end region configured to create two cuts in concert with the outer tube. The elongate member can include a proximal opening positioned within a chamber of a vacuum manifold in fluid communication with the aspiration pump.

The elongate member can be configured to oscillate at 300 cuts per minute. The elongate member can be configured to oscillate at 500-600 cuts per minute. The elongate member can be configured to oscillate up to about 5000 cuts per minute. The elongate member can be configured to oscillate up to about 7500 cuts per minute. The device can further include a gearbox configured to amplify the input from the pump to achieve an output of the elongate member configured for vitrectomy. The gearbox can be a planetary gearbox. The device can further include a drive mechanism configured to operatively couple with the camshaft. The drive mechanism is configured to rotate the camshaft. The device can further include gearing to ramp up input from the drive mechanism. The camshaft of the aspiration pump can rotate at a fixed rate to deliver between about 15 cc/minute and 30 cc/minute of aspiration potential. The input from the drive mechanism can be about 140 RPMs and the gearing can have a ratio that is at least about 3:1, 4:1, 5:1, 6:1, up to about 30:1. The drive mechanism configured to rotate the camshaft can also drive oscillation of the elongate member. The camshaft can operatively interface with a cutter assembly configured to convert rotary motion of the camshaft with reciprocal linear motion of the elongate member. The cutter assembly can include a ramp cam and a cutter return spring. Proximal motion of the elongate member can be a function of the ramp cam and distal motion of the elongate member can be a function of the cutter return spring.

The cutter assembly can include a translating magnet disc and a rotating magnet disc. The translating magnet disc can include one or more magnets and the rotating magnet disc can include one or more magnets. The one or more magnets of the translating magnet disc and the rotating magnet disc can create a local magnetic field as the one or more magnets of the rotating magnet disc spin in and out of alignment with the one or more magnets of the translating magnet disc. The translating magnet disc can be coupled to a cutter spline and the cutter spline can be coupled to the elongate member such that the translating magnet disc, the cutter spline, and the elongate member all translate axially together. The translating magnet disc, cutter spline, and the elongate member can be configured to move bidirectionally a distance axially along the longitudinal axis due to rotation of the camshaft. Alignment of the one or more magnets of the rotating magnet disc with the one or more magnets of the translating magnet disc can cause linear motion by magnetic attraction or magnetic repulsion. The rotating magnet disc can include a plurality of magnets oriented relative to one another so that poles of the magnets alternate. Rotation of the rotating magnet disc relative to the translating magnet disc can cause the poles of the plurality of magnets to cause alternating repulsion and attraction with the one or more magnets of the translation magnet disc causing oscillation of the elongate member. The device can further include a second rotating magnet disc comprising one or more magnets. The second rotating magnet disc can be positioned distal to the translating magnet disc. Alignment of the one or more magnets of the first and second rotating magnet discs with the one or more magnets of the translating magnet disc can cause oscillation of the cutting tube. The one or more magnets of the second rotating magnet disc can have poles arranged to cause repulsion of the one or more magnets of the translating magnet disc with the one or more magnets of the first rotating magnet disc have poles arranged to cause attraction. The repulsion and attraction can create a stronger magnetic field to urge the translating magnet disc to move linearly between the first and second rotating magnet discs. The second rotating magnet disc can form a distal hard stop and the first rotating magnet disc can form a proximal hard stop for the translating magnet disc.

The device can include a cutter switch configured to decouple physically rotation of the camshaft from oscillation of the elongate member. The cutter switch can control whether the elongate member oscillates upon activation of an input on the hand held portion. The cutter switch can lock out oscillation of the elongate member during rotation of the cutter assembly. A bleed valve can be functionally coupled to an input of the hand-held portion. The bleed valve can be configured to modulate effective flow rate of the aspiration pump through the lumen of the elongate member. The input can be a trigger configured to be pressed. An open configuration of the bleed valve can siphon substantially all aspiration generated by the aspiration pump away from the lumen of the elongate member. A closed configuration of the bleed valve can direct full aspiration generated by the aspiration pump through the lumen of the elongate member. The bleed valve can be a needle valve having a helical driven needle movable relative to a valve seat in a fluidic channel. An open configuration of the needle valve can connect the aspiration pump to an irrigation fluid line resulting in minimal aspiration through the lumen of the elongate member. A first amount of travel of the trigger away from a resting state can activate the aspiration pump. The needle valve can remain open so that aspiration from the aspiration pump is not delivered through the lumen of the cutting tube. A second further amount of travel of the trigger away from the resting state can urge the needle toward the valve seat. The first amount of travel can be greater than zero and less than about 20% of a trigger stroke. The second further amount of travel can be at least 20% of a trigger stroke.

In an interrelated implementation, provided is a kit for performing an ophthalmic procedure in an eye. The kit includes a driver portion having a motor and a rotatable coupler. The kit includes a first working portion for performing a first ophthalmic procedure in the eye and configured to operatively couple with the rotatable coupler of the driver portion. The first working portion includes a first elongate member extending from a distal end region of the first working portion. The first elongate member includes a lumen and an opening near a distal end region of the first elongate member, and a piston pump within the first working portion in fluid communication with the opening near the distal end region of the first elongate member, the piston pump configured to generate pulsed aspiration. The kit includes at least a second working portion configured to operatively couple with the rotatable coupler of the driver portion for performing a second ophthalmic procedure in the eye. The second working portion includes a second elongate member extending from a distal end region of the second working portion. The second elongate member includes a lumen and an opening near a distal end region of the second elongate member. The second working portion includes a linear peristaltic pump within the second working portion in fluid communication with the opening of the second elongate member. The linear peristaltic pump is configured to generate smooth flow aspiration.

The piston pump can include a plurality of pistons and a rotational cam assembly capable of being rotated by the motor via the rotatable coupler. Rotation of the rotational cam assembly can cause the plurality of pistons to generate pulses of discontinuous negative pressure within the lumen of the first elongate member. The piston pump can be configured to generate up to about 100 cc/minute volume aspiration. The linear peristaltic pump can include a camshaft extending along a longitudinal axis and having a plurality of lobed cams. The linear peristaltic pump can include tubing extending parallel to the longitudinal axis and a plurality of cam followers driven by the cams of the camshaft to move in a plane perpendicular to the longitudinal axis to compress the tubing sequentially. The plurality of cam followers can sequentially compress the tubing creating a substantially non-pulsatile aspiration. The substantially non-pulsatile aspiration can be up to about 10 cc/minute. The motor can be configured to drive reciprocating motion of the first elongate member and the second elongate member. The first elongate member can be configured for lens fragmentation and the second elongate member can be configured for anterior vitrectomy.

In some variations, one or more of the following can optionally be included in any feasible combination in the above methods, apparatus, devices, and systems. More details of the devices, systems, apparatus, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking, the figures are not to scale in absolute terms or comparatively, but are intended to be illustrative. In addition, relative placement of features and elements may be modified for the purpose of illustrative clarity.

FIG. 1B is a block diagram of an implementation of a microsurgical instrument having an integrated aspiration pump;

FIG. 2C shows a partial view of the driver portion of the instrument of FIG. 2B;

Figure 1A:
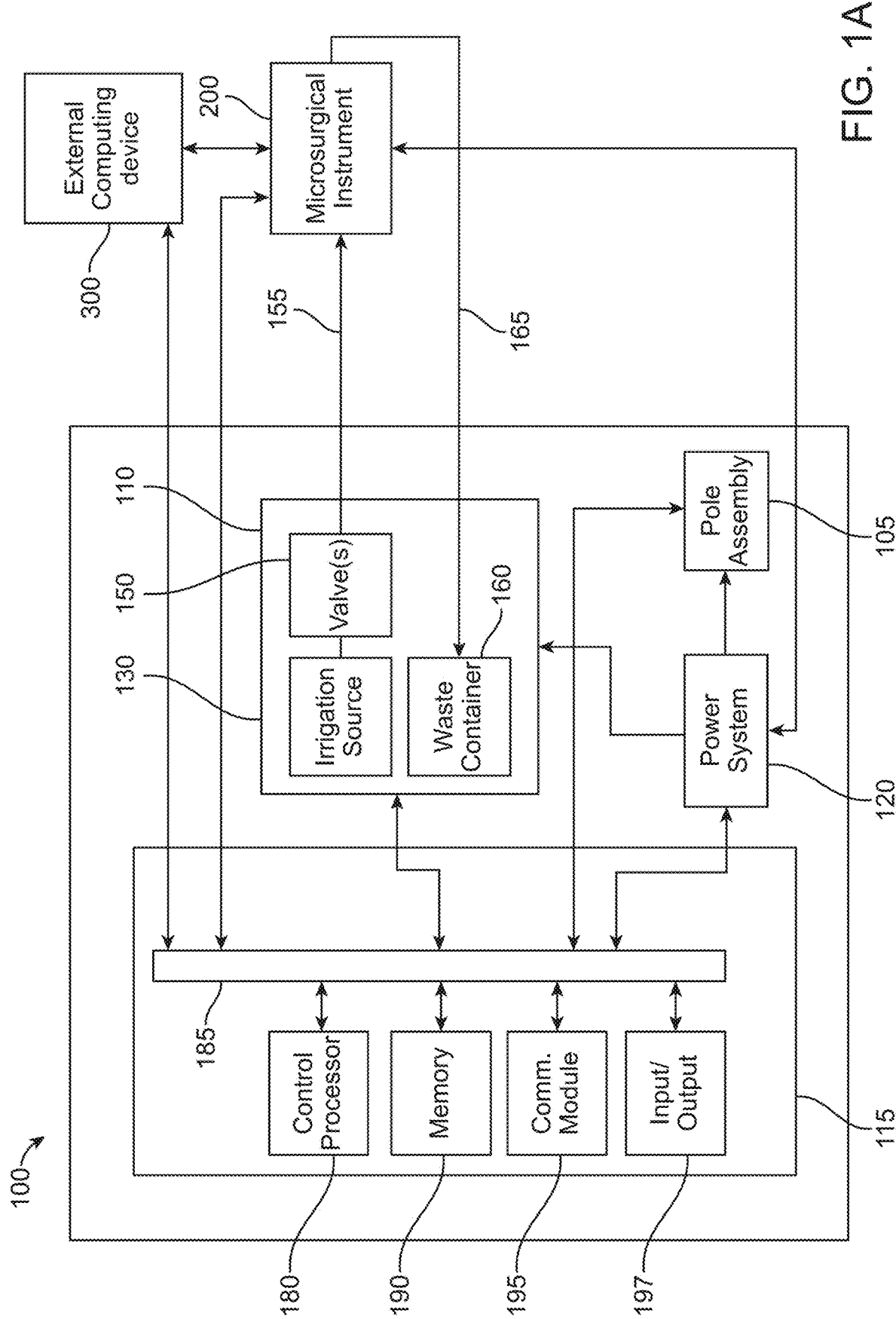
FIG. 1A is a block diagram of a microsurgical control system for use with a microsurgical instrument.

It should be appreciated that the drawings are for example only and are not meant to be to scale. It is to be understood that devices described herein may include features not necessarily depicted in each figure.

DETAILED DESCRIPTION

Described herein are systems, devices, and methods for useful for intraocular fragmentation and removal of the lens, vitreous, and other tissues during intraocular surgery. The various systems, devices, and methods are configured to perform one or more functions useful in ophthalmic procedures including, but not limited to, cutting, fragmentation, emulsification, aspiration, and/or irrigation of material present at a target location during a procedure in the eye. The systems, devices, and methods described herein are configured to apply vacuum and deliver fluids to maintain a pressure balance within the eye. The systems, devices, and methods described herein that apply vacuum and/or deliver fluids may also be configured to cut, fragment, emulsify, or otherwise make smaller material in and near the surgical site.

"Material" as used herein can include fluids (from the eye or provided to the eye), tissues, or fragments of tissues such as lenticular tissue, vitreous, cells, and any other fluid or tissue or other material that may be present during a procedure in the eye (e.g. cataract procedure, vitrectomy procedures, and the like).

The systems described herein can include a single, reusable driver portion configured to operatively couple with one or more disposable working portions in an interchangeable manner. The disposable working portions can be configured for different types of ophthalmic procedures including lens fragmentation, phacoemulsification, vitrectomy, bag polishing, aspiration, irrigation, coagulation, illumination, visualization, intraocular lens (IOL) insertion, and others.

The operating parameters of the instrument can differ according to, for example, the configuration of the disposable working portion that is attached to the reusable driver portion.

The various features and functions of the devices described herein may be applied to one or more devices described herein even though they may not be expressly described in combination. It should also be appreciated that various features and functions of the devices described herein can be applied to conventional devices and systems known in the art also useful for cutting, fragmenting, emulsifying, or otherwise impacting tissues at or near a surgical site, including, but not limited to phacoemulsification systems, vitrectomy systems, bag polishing systems, and other tools useful in performing cataract surgeries or vitrectomy surgery, and the like.

The instruments described herein are configured to apply vacuum and deliver fluids to the eye as well as to cut, fragment, emulsify, or otherwise make smaller material in and near the surgical site. Ophthalmological systems are often controlled using a foot pedal. The user may control the hand piece functions based on position of the foot pedal. As an example, when the foot pedal is not depressed the hand piece is in an idle, resting position where no irrigation, aspiration, and/or cutting occurs. A user may actuate the foot pedal by pressing down to a first position to turn on irrigation, a second further depression of the foot pedal may add aspiration to the irrigation, and a third degree of depression of the foot pedal may activate cutting. Travel of the foot pedal into various positions provides the user with control of different surgical functions.

The instruments described herein need not be controlled by a foot pedal. For example, the instruments described herein preferably include a finger-actuated throttle rather than a foot-actuated throttle. The functions of the instruments described herein (i.e. irrigation, aspiration, and/or cutting functions) can be initiated using an input on the housing of the instrument capable of being actuated with a single finger or thumb. Because the instruments described herein require no foot pedal, a user can stand more comfortably and naturally (e.g. on two feet or shifting their weight from foot to foot) to perform a procedure. The instruments described herein are capable of providing background flow or irrigation/aspiration with or without tip cutting action. The instruments described herein can produce low-level irrigation and/or suction without cutter action upon actuation of a finger-actuated input. The finger control on the instrument allows the surgeon to easily activate and finely control the system for short periods in a manner more convenient and easier than would a foot pedal used in most conventional phacoemulsification/vitrectomy systems.

The instruments are sometimes referred to herein as a "device" or "tool" or "peripheral device" or "hand piece" or "hand held unit". Use of the term "hand piece" herein can include a hand piece coupled to a robotic arm or robotic system or other computer-assisted surgical system in which the user uses a computer console to manipulate the controls of the instrument. The computer can translate the user's movements and actuation of the controls to be then carried out on the patient by the robotic arm.

The instruments described herein are capable of aspiration through a cutting tube via a vacuum source (e.g. a pump) located within the housing of the instrument. The vacuum source within the hand-held portion of the device (e.g. near the distal cutting tip) minimizes the volume of the aspiration flow path improving control and responsiveness while decreasing latency or hysteresis. Conventional systems rely on a vacuum source located in a remote console that is several feet away and connected by long, compressible tubing and suffer from slow responsiveness and lower effective vacuum applied at the treatment site. Conventional systems have long, compliant suction lines connecting the vacuum source to the hand-piece. Compliance within a fluidic system can increase the time for suction to be transmitted from the suction source to the treatment site when the suction source is activated (and deactivated). Compliance within a fluidic system can also contribute to frictional losses in vacuum transmitted to the treatment site resulting in the effective vacuum amount being different from the theoretical vacuum setting at the source. For example, a remote vacuum source set at 600 mmHg may effectively transmit to the treatment site only 200 mmHg. The latency and hysteresis in conventional phaco devices having a remote vacuum source suffer from the risk of large surge volume following a clog, particularly when the vacuum source is set at the higher flow rates. Surge volume in conventional systems includes the compliant suction line extending between the remote vacuum source and the hand-piece, which can be quite large (e.g. greater than 20 mL in some instances). Users tend to set the vacuum source at lower levels to mitigate this lack of control and increased risk in surge volume at the higher flow rates. The instruments described herein have a relatively low amount of surge volume, and therefore cycling the device on and off has minimal downside. These features can allow the instruments to be activated for only brief periods when the surgeon is ready to remove lenticular tissue. This contributes to overall less irrigation fluid being removed and thus less irrigation fluid needed to be delivered.

The instruments described herein can apply a greater effective vacuum at the treatment site and more rapidly respond to pressure changes, and by avoiding the line losses associated with conventional systems. The devices described herein have improved responsiveness and control even when used with the higher vacuum settings. If an occlusion occurs due to a piece of lens blocking the distal opening, the vacuum will build (e.g. up to about 500 to 600 mmHg or more). When the blockage passes breaking the seal, the surge associated with the devices described herein is significantly improved as compared to conventional devices having only remote vacuum sources. For example, the surge volume of the devices described herein can be as low as about 100 cubic mm, 200 cubic mm, or no more than about 300 cubic mm, whereas conventional phacoemulsification machines can have surge volumes that can be 10×, 20×, 50×, or 100× greater than this volume. The surge volume is smaller because the devices described herein have a comparatively shorter aspiration flow path between vacuum source and target treatment site. The short aspiration flow path may also be substantially rigid or non-compliant. For example, greater than 50%, 55%, 60%, 65%, 70%, 75%, 80%, 85%, 90% of the aspiration flow path of the devices described herein can be rigid resulting in no more than 10%, 15%, 20%, 25%, 30%, 35%, 40%, 45%, or 50% compliance in the aspiration flow path. The substantially non-compliant and short aspiration flow path of the devices described herein reduces the potential surge volume and reduces the dead space that can contribute to the latency effect and lack of responsiveness.

The instruments described herein include a cutting tube capable of oscillating or sliding in a reciprocating manner relative to the housing. As used herein, "oscillate" or "oscillating movements" can include any periodic, repetitive movement that occurs according to a pattern and need not be sinusoidal. The oscillating movement can include reciprocating sliding movements that occur in a back and forth manner relative to the hand piece. The oscillating movement can include repeatedly advancing and retracting the cutting tube along its longitudinal axis. The repeated advancing and retracting may occur along the longitudinal axis, but the path the oscillating movements take need not be linear. The path of movement can occur non-linearly (i.e. away from the longitudinal axis during at least a portion of the movement) along an elliptical pathway or a curvilinear pathway. The path of movement can be rotational, orbital, or torsional around the longitudinal axis of the device or other type of movement relative to the longitudinal axis of the device including three-dimensional movements in which the cutting tube moves back and forth as well as from side-to-side. The oscillating movements include profiles of repetitive patterns that may change depending on where in the cycle of oscillation the movement occurs. The oscillating movements can be asymmetric in profile, as described in U.S. Publication No. 2018/0318133, published Nov. 8, 2018, which is incorporated herein by reference.

The elongate component of the instrument being oscillated may be referred to herein as a "shaft" or "cutter" or "cutting tube" or "elongate member" and can be configured for different techniques, including phacoemulsification, vitrectomy, bag polishing, or other technique. At least a portion of the cutter can be tubular and having an internal lumen extending through it such that fluids can be delivered and/or aspirated through the internal lumen between a distal opening and a proximal opening from the lumen.

Oscillation of the cutter can jackhammer lens tissue and aspirate it out of the eye similar to conventional phacoemulsification cutting tips. The cutter can include an inner elongate member coaxially arranged within an outer tubular member or the cutter can be a solid rod and need not include an inner lumen. In some implementations, the cutter has a sharpened cutting tip or bevel, which can include a needle tip. The cutter can include a sharpened needle tip and can be a solid element extending through an outer tubular member and aspiration forces applied through the lumen of the outer tubular member such that fluids and tissues are drawn into an annular gap extending between the inner and outer members. The cutter can have an inner lumen and distal edge configured to cut tissue. The distal edge can be sharpened while the opening into the tube can be cut at an angle to the elongate axis of the cutter or perpendicular to the elongate axis of the cutter. The inner lumen of the cutter can be configured to aspirate material therethrough, such as ocular lens material, lens fragments, vitreous, and/or fluids from the eye. Thus, aspiration forces can be applied through the inner lumen of the cutter. However, aspiration forces can also be applied through a lumen of a tubular outer member extending over the cutter such that aspiration occurs through the annular space between the two in order to receive and/or deliver fluids to the treatment site. In such a configuration, the gap between the tubular outer member and the inner member can vary, for example, between about 0.001" to about 0.100". In some implementations, the aspiration forces can be applied through both the inner elongate member having a lumen and the lumen through the outer tubular member.

The instruments described herein integrate oscillating cutting action with aspiration pumping within the hand piece. The oscillating movements of the cutter and the aspiration generated by the pump are both powered by a motor in the hand piece. As will be described in more detail below, the aspiration and the cutting can be driven by the motor independently thereby decoupling these functions of the instrument.

Figure 1C:
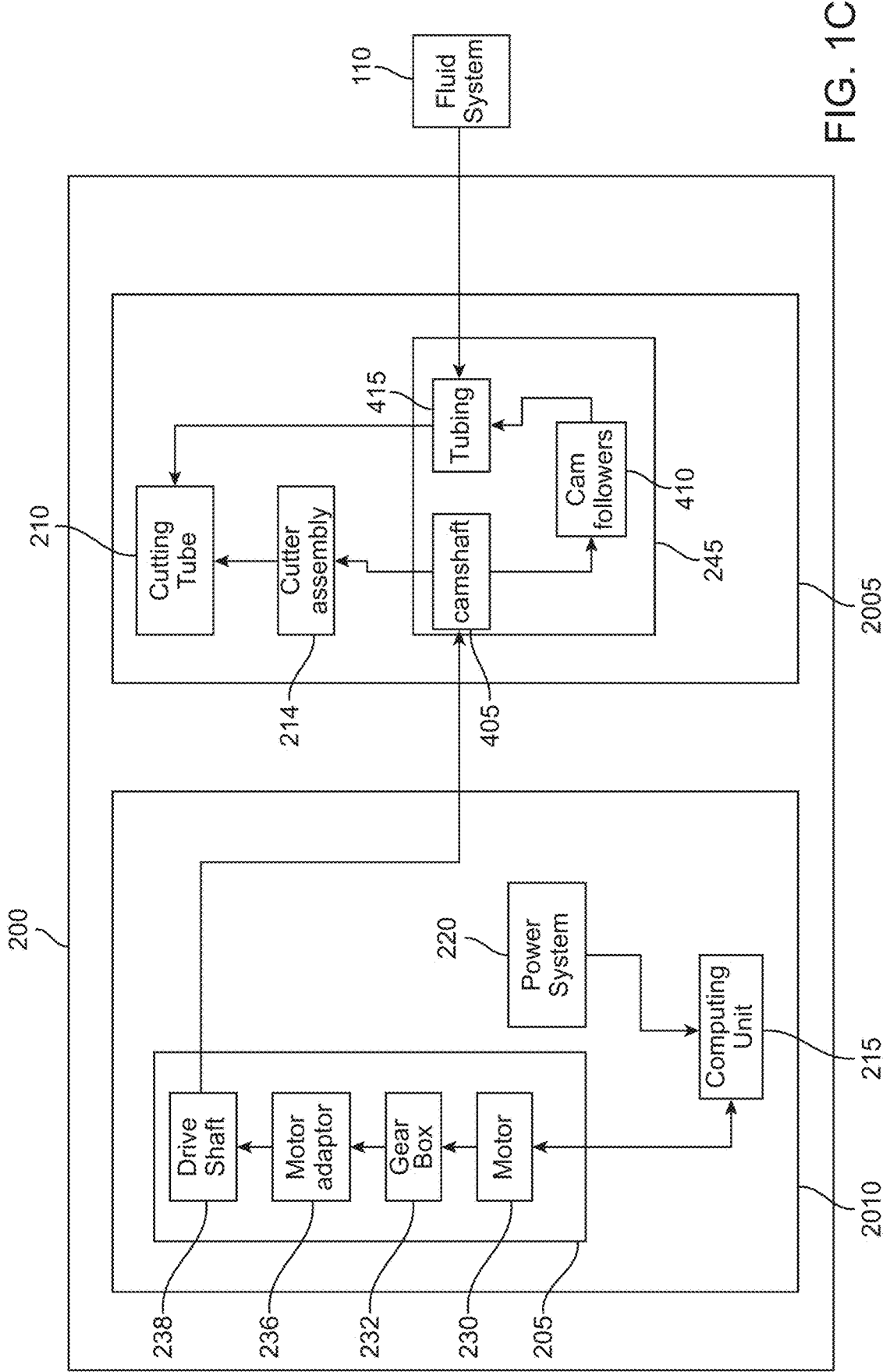
FIG. 1C is a block diagram of an implementation of a microsurgical instrument including disposable working portion having another implementation of an integrated aspiration pump configured to operatively couple with the reusable driver portion.

FIG. 1A shows a box diagram of a system 100 configured to be used with a microsurgical instrument 200 for use by a surgeon in performing various ophthalmic surgical procedures. FIGS. 1B-1C show box diagrams of an instrument 200 (sometimes referred to herein as a "device" or "tool" or "peripheral device" or "hand piece" or "hand held unit") according to implementations and will be described in more detail below. The microsurgical instruments 200 can be used with the system 100 shown in FIG. 1A and can be used separate from the system 100 and used as fully hand-held independent instruments.

In some implementations, the microsurgical system 100 can include a fluid system 110 that is coupled to a pole assembly 105. The pole assembly 105 and the fluid system 110 can each be controlled by a computing unit 115 powered by power system 120. The fluid system 110 can include an irrigation fluid source 130, an irrigation line 155 leading to the microsurgical instrument 200, a waste line 165 leading from the microsurgical instrument 200 towards and a waste container 160. The system 100 can provide irrigation to the microsurgical instrument 200 by coupling the irrigation line 155 of the fluid system 110 to an irrigation inlet of the instrument 200.

Some commercially available anterior vitrectors are not designed for coaxial irrigation and vitreous cutting. Local turbulent flow and vitreous volume expansion from hydration can be an issue with the coaxial irrigation and cutting systems. Thus, in some implementations, irrigation can be performed with a bimanual approach separating the cutting from the irrigation. Thus, the irrigation line 155 can also be coupled to a different instrument configured to deliver irrigation to the treatment site.

One or more components of the system 100 can be controlled by the computing unit 115 powered by a power system 120. The computing unit 115 can include a control processor 180, a memory 190, a communication module 195, and one or more input/outputs 197. Components of the computing unit 115 such as the control processor 180, memory 190, communication module 195, one or more input/outputs 197, storage devices, etc. can be interconnected via a system bus 185. The control processor 180 can be in operative communication with one or more of the pole assembly 105, the fluid system 110, and the microsurgical instrument 200 operatively coupled to the system 100. The control processor 180 can also be in operative communication with one or more external computing devices 300. The external computing device 300 can vary including, but not limited to, desktop computer, laptop computer, tablet computer, smartphone, or other device capable of communicating and receiving user input.

The memory 190 is configured for receiving and storing user input data. The memory 190 can be any type of memory capable of storing data and communication that data to one or more other components of the system 100, such as the control processor 180. The memory 190 may be one or more of a Flash memory, SRAM, ROM, DRAM, RAM, EPROM, dynamic storage, and the like. The memory 190 can be configured to store one or more user-defined profiles relating to the intended use of the instrument 200. The memory 190 can be configured to store user information, history of use, measurements made, and the like.

The communication module 195 of the computing unit 115 can be in operative communicate with one or more components of the system 100, such as the control processor 180, as well as with one or more peripheral devices such as the one or more external computing devices 300 and the microsurgical instrument 200. The connection between the communication module 195 of the computing unit 115 and the external computing device 300 or microsurgical instrument 200 can include a wired communication port such as a RS22 connection, USB, Fire wire connections, proprietary connections, or any other suitable type of hard-wired connection configured to receive and/or send information to the external computing device 300 and/or microsurgical instrument 200. The communication module 195 can also include a wireless communication port such that information can be fed between the computing unit 115 and the external computing device 300 and/or microsurgical instrument 200 via a wireless link, for example, to display information in real-time on the external computing device 300 about operation of the system 100, and/or control programming of the microsurgical instrument 200. It should be appreciated that the external computing device 300 can communicate directly to the microsurgical instrument 200, for example, if the instrument 200 is being operated independently of the system 100. Any of a variety of adjustments to and programming of the system 100 can be performed using the external computing device 300. The wireless connection can use any suitable wireless system, such as Bluetooth, Wi-Fi, radio frequency, ZigBee communication protocols, infrared, or cellular phone systems, and can also employ coding or authentication to verify the origin of the information received. The wireless connection can also be any of a variety of proprietary wireless connection protocols.

The control processor 180 can be capable of processing instructions for execution within the system 100. Such executed instructions can implement one or more of the processes described herein related to the use of the system or peripheral devices in operative communication with the system 100. The control processor 180 can be a single-threaded processor or a multi-threaded processor. The control processor 180 can be capable of processing instructions stored in the memory 190 and/or on a storage device to provide an output of information to the user about operation of the system 100. The control processor 180 can include software capable of being programmed to adjust or provide limits on the one or more aspects of the system 100 as well as a microsurgical instrument 200 coupled to the system 100. The software run by the control processor 180 can provide certain aspects of the system 100 or a microsurgical instrument connected to the system 100 without any user input during use. In an implementation, the adjustments or programming can be via the control processor 180 that is controlled by software, either within the system 100 or on the external computer device 300. A user can program the controller 180 remotely via the external computing device 300 in communication with the system 100 via a wireless connection such as Bluetooth. One or more aspects of the system 100, which will be described in detail below, can be programmed including the height of irrigation source 130, position of the valve 150 configured to control irrigation flow, etc.

As mentioned, the computing unit 115 of the system 100 (or of the instrument 200) can be controlled, adjusted, and/or programmed remotely such as via an external computing device 300. The computing unit 115 of the system 100 can also be controlled, adjusted, and/or programmed directly via one or more inputs 197 on the system 100 (as well as one or more inputs 228 on the instrument 200). The devices described herein can be used such that one or more aspects are manually controlled and/or adjusted according to manual inputs by the user or programmed to control the one or more aspects. The controller can include software capable of being programmed to adjust or provide limits on the one or more aspects of the device. The software run by the controller can provide certain aspects of the device without any user input during use. In an implementation, the adjustments or programming can be via a controller that is controlled by software, either within the device or on an external computer device 300 in operative communication with the device directly or via the system 100. A user can program the controller remotely via an external computing device, the external computing device being in communication with the device via a wireless connection such as Bluetooth.

The inputs 197 of the system 100 can include one or more triggers, buttons, sliders, dials, keypads, switches, touchscreens, foot pedals, or other input that can be retracted, pressed, squeezed, slid, tapped, or otherwise actuated to activate, modify, or otherwise cause a response of the system 100. In some implementations, the one or more inputs 197 includes a microphone configured to receive voice commands to control, adjust, and/or program one or more components of the system 100 as well as peripheral devices in operative communication with the system 100. The inputs 197 of the system can be separate from and in addition to one or more inputs 228 on the microsurgical instrument 200, which will be discussed in more detail below. The system 100 (and the instrument 200) may include one or more outputs such as lights, speakers, vibration motors, displays or other sort of output configured to communicate information to the user by visual, audio, and/or tactile outputs.

Again, with respect to FIG. 1A, one or more of the pole assembly 105, the fluid system 110, the computing unit 115, as well as a microsurgical instrument 200 or other peripheral device connected to the system 100, can be powered by the power system 120. For example, the power system 120 can provide power to the pole assembly 105 to adjust the height of the irrigation source 130 by telescopically adjusting the pole relative to a base such as with a motor or other powered mechanism. The power system 120 can provide power to the one or more valves 150 configured to control fluid flow towards the irrigation line 155. The power system 120 can also provide power to any peripheral devices, such as the microsurgical instrument 200, in operative communication with the system 100.

Still with respect to FIG. 1A, and as mentioned above, the fluid system 110 can include an irrigation fluid source 130, one or more valves 150, an irrigation line 155, a waste line 165, and a waste container 160. The fluid system 110 may optionally include a pump, such as an irrigation fluid pump configured to deliver irrigation fluid from the irrigation fluid source 130. Irrigation fluid may exit the irrigation fluid source 130 and travel toward the microsurgical instrument 200 through the irrigation fluid line 155. The lines 155 and 165 may fluidly couple to the instrument 200 either directly or through an irrigation port.

The irrigation fluid source 130, instrument 200, and/or the irrigation line 155 may optionally include one or more valves 150 and/or sensors configured to provide additional control of fluid flow through the irrigation line 155 fluidly coupled to the instrument 200 either directly or through an irrigation port. The one or more valves 150 can be pinch valves or pinch clamps configured to pinch tightly the irrigation line 155 thereby preventing fluid flow towards the microsurgical instrument 200 or allowing full fluid flow from the irrigation source 130 towards the microsurgical instrument 200 upon opening the valve 150.

The valve 150 can be opened/closed manually as is known in the art. The valve 150 can alternatively or additionally be actuated upon input by the computing unit 115, for example, upon actuation of the microsurgical instrument 200 as will be described in more detail below. Other valve and clamp types are considered herein. The instrument 200 and/or the waste line 165 (which may be referred to herein as the aspiration line) may optionally include one or more valves and/or sensors configured to provide additional control of fluid flow from the instrument 200. The one or more valves 150 can be integrated within a region of the telescoping pole near wherein the irrigation source 130 hangs such that the valves 150 can control flow through the irrigation line 155.

FIGS. 1B-1C show box diagrams of instruments 200 (sometimes referred to herein as a "device" or "tool" or "peripheral device" or "hand piece" or "hand held unit"). The instrument 200 can include a drive mechanism 205 in operative communication with a vacuum source such as the aspiration pump 245 in the housing of the instrument 200, and in operative communication with the cutting tube 210 coupled to the housing. The cutting tube 210 is configured to be inserted into an eye to cut, aspirate, and/or inject material in the eye, such as during a cataract procedure. At least a portion of the cutting tube 210 is configured to move such as by oscillating or sliding reciprocally relative to the housing in order to remove lens or other tissues of the eye. Each of these will be described in more detail below.

Any of a number of microsurgical instruments 200 are considered herein for use with the microsurgical system 100 described above, including vitrectomy cutters, phacoemulsification or phacofragmentation hand-pieces, electric micro-scissors, fiber optic illumination instruments, coagulation hand-pieces, and other microsurgical instrument. In some implementations, the instrument 200 is one or more of those described in U.S. Patent publication No. 2018/0318133, published Nov. 8, 2018, which is incorporated by reference herein in its entirety. The operating parameters can differ according to, for example, the particular procedure being performed, the different stages of the procedure, the surgeon's personal preferences, whether the procedure is being performed in the anterior or posterior portion of the patient's eye, and so on.

The microsurgical instruments 200 can be used with the system 100 described with respect to FIG. 1A. The microsurgical instruments 200 described herein can also be used separate from the system 100 and can be fully hand-held independent instruments. FIGS. 1B and 1C illustrate implementations of the instrument 200 having an integrated aspiration pump 245 within the housing. In some implementations, a single input (i.e., drive mechanism) can drive both the cutting tube 210 and the aspiration pump 245. The single input or drive mechanism of the instrument 200 can control the cutting tube 210 and the aspiration pump 245 independently.

Figure 3B:
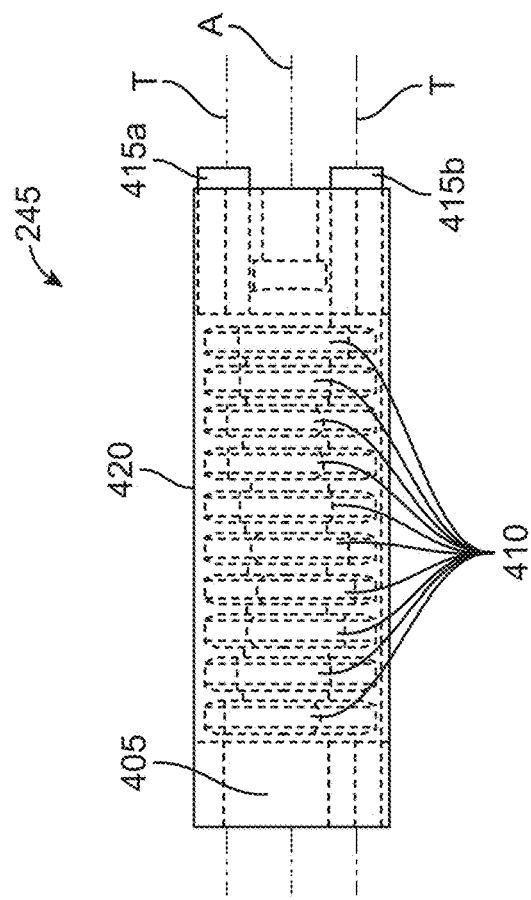
FIG. 3B shows a top view of the aspiration pump of FIG. 3A.
Figure 3A:
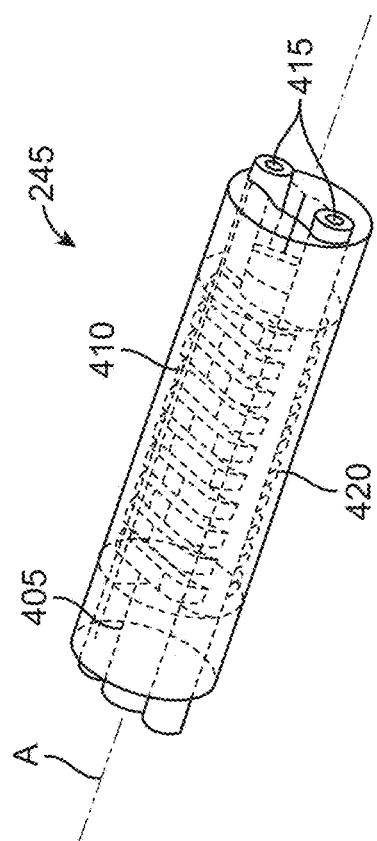
FIG. 3A shows a perspective view of an implementation of an aspiration pump configured to be integrated within a working portion of a microsurgical instrument.
Figure 12:
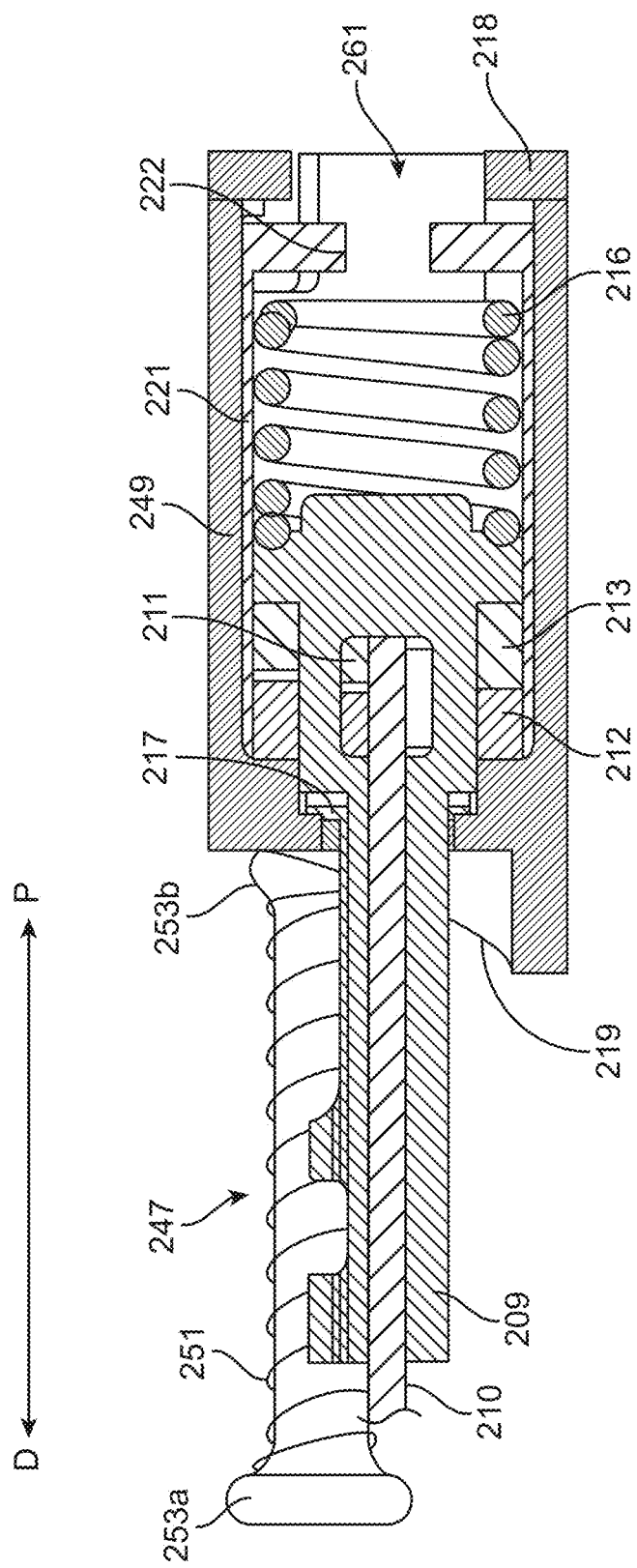
FIG. 12 shows a camming mechanism for cutting and aspiration configured to couple with the driver portion of FIG. 10.

The configuration of the aspiration pump 245 of the instrument 200 can vary. Preferably, the aspiration pump 245 has a small form factor such that it does not significantly affect the relative ergonomics of the hand piece. The aspiration pump 245 can be a piston pump, roller pump, peristaltic pump, linear peristaltic pump, scroll-type pump, venturi, rotary vane, gear, screw, diaphragm, centrifugal, bellows mechanism, entrapment pump, positive displacement pump, regenerative pump, momentum transfer pump, micro pumps, or the like. In some implementations, the aspiration pump 245 of the instrument 200 is a linear peristaltic pump as shown in FIGS. 3A-3B. In other implementations, the aspiration pump 245 of the instrument 200 is a piston pump as shown in FIG. 12. The aspiration pump 245 of the instrument will be described in more detail below.

FIG. 1C illustrates the instrument 200 can include a disposable, working portion 2005 configured to be releasably coupled to a durable, reusable driver portion 2010. Each of the working portion 2005 and the driver portion 2010 can include a housing portion formed of a relatively rigid, lightweight material(s). The working and driver portions 2005, 2010 can couple together using a variety of mechanisms such as threads, snap-lock, bayonet, and similar mechanisms. The coupling mechanism can include a release button configured to uncouple the two housing portions. The coupling between the working portion 2005 and the driver portion 2010 may be purely mechanical or may involve both mechanical and electronic couplings. For example, the working portion 2005 may have an electronic input configured to electronically couple with a portion of the driver portion 2010. Alternatively, the working portion 2005 may have an input configured to mechanically couple and interact with the driver portion 2010. Coupling between the portions 2005, 2010 will be described in more detail below.

The working portion 2005 generally includes components of the instrument 200 configured to come into direct contact with fluids and materials from the eye, for example the cutting tube 210 as well as the connection sites for the irrigation line 155 and waste line 165, etc. (not shown in FIG. 1C). The aspiration pump 245 can be within the working portion 2005. The durable, driver portion 2010 of the instrument 200 generally includes the components of the instrument 200 that are configured to remain outside the fluid path, for example, the components of the drive mechanism 205.

The instrument 200 can include a computing unit 215 including a control processor 280, memory 290, and/or communication module 295 in operative communication with one or more components of the instrument 200, such as a power system 220 and the drive mechanism 205. The components of the computing unit 215 such as the control processor 280, the memory 290, communication module 295, and one or more input/outputs 228, etc. can be interconnected via a system bus 285. The computing unit 215 and the power system 220 can be contained within the durable, driver portion 2010 of the instrument 200. The input 228 may be on the reusable, durable driver portion 2010 or the working portion 2005. The driver portion 2010 may be resterilized and reused while the working portion 2005 is not. It should be appreciated, however, that the entire instrument 225 including the driver portion 2010 may also be disposable and manufactured by lower cost materials such that it is financially feasible for the portion 2010 to be disposed of after use.

The devices described herein can be programmed to control the one or more aspects. The controller can include software capable of being programmed to adjust or provide limits on the one or more aspects of the device. Thus, the software run by the controller can provide certain aspects of the device without any user input during use. In an implementation, the adjustments or programming can be via a controller that is controlled by software, either within the device or on an external computer device. A user can program the controller remotely via an external computing device in communication with the device via a wireless connection such as Bluetooth.

As mentioned above, the instrument 200 can include a power system 220. Power also can be supplied to the drive mechanism 205 by the power system 120 of the system 100 when the instrument 200 is operatively coupled to the system 100. The instrument 200 can include a cable 225 extending through the housing 226 of the durable driver portion 2010. The cable 225 may also be configured to connect the instrument 200 to a wall socket. The drive mechanism 205 can also be powered by one or more batteries. The battery can be incorporated within a region of the durable driver portion 2010, either internally or coupled to a region of the housing such as within a modular, removable battery pack. The battery can have different chemical compositions or characteristics. For instance, batteries can include lead-acid, nickel cadmium, nickel metal hydride, silver-oxide, mercury oxide, lithium ion, lithium ion polymer, or other lithium chemistries. The device can also include rechargeable batteries using either a DC power-port, induction, solar cells, or the like for recharging. Power systems known in the art for powering medical devices for use in the operating room are also to be considered herein such as spring power or any other suitable internal or external power source. In some implementations, rather than the battery back mounted on or in the housing, which can increase the size of the housing, the battery pack can be mounted elsewhere such as on a user's arm or wrist of the arm holding the instrument 200 during a procedure. A short cable connector can connect the mounted battery back to the instrument 200 such that only this linkage extends from the housing of the instrument 200 during use.

The processor 280 can be capable of processing instructions for execution within the instrument. Such executed instructions can implement one or more of the processes described herein related to the use of the instrument. The processor 280 can be a single-threaded processor or a multi-threaded processor. The processor 280 can be capable of processing instructions stored in the memory 290 and/or on a storage device to provide an output of information to the user about operation of the device.

The memory 290 can be configured for receiving and storing user input data. The memory 290 can be any type of memory capable of storing data and communication that data to one or more other components of the device, such as the processor. The memory 290 may be one or more of a Flash memory, SRAM, ROM, DRAM, RAM, EPROM, dynamic storage, and the like. The memory 290 can be configured to store one or more user-defined profiles relating to the intended use of the device. The memory 290 can be configured to store user information, history of use, measurements made, and the like.

The connection between the communication module 295 of the instrument 200 and the system 100 or the external computing device 300 can include a wired communication port such as a RS22 connection, USB, Firewire connections, proprietary connections, or any other suitable type of hard-wired connection configured to receive and/or send information to the external computing device. The communication module 295 can also include a wireless communication port such that information can be fed between the device and the external computing device via a wireless link, for example, to display information in real-time on the external computing device 300 about operation of the instrument, and/or control programming of the instrument. For example, a user can program the speed profile of the motor of the device on the external computing device. Any of a variety of adjustments to and programming of the device can be performed using the external computing device 300. The wireless connection can use any suitable wireless system, such as Bluetooth, Wi-Fi, radio frequency, ZigBee communication protocols, infrared, or cellular phone systems, and can also employ coding or authentication to verify the origin of the information received. The wireless connection can also be any of a variety of proprietary wireless connection protocols. The external computing device 300 with which the instrument communicates can vary including, but not limited to, desktop computer, laptop computer, tablet computer, smartphone, or other device capable of communicating and receiving user input.

As mentioned, the microsurgical instrument 200 can include one or more user inputs 228 that can be separate from the one or more inputs 197 of the system 100. The instrument 200 can be actuated using the one or more user inputs 228 on the instrument itself, as well as inputs remote from the device (e.g. on the system 100 or an external computing device 300 in operative communication with the system 100), or both. The one or more inputs 228 on the instrument 200 include any of a variety of actuator, trigger, button, slider, dial, keypad, switch, touchscreen, foot pedal, footswitch, or other input that can be retracted, pressed, squeezed, slid, tapped, or otherwise actuated to activate, modify, or otherwise cause the oscillation, aspiration, and/or infusion of fluid through the cutting tube. In a preferred implementation, the input 228 is a multi-way trigger configured to activate more than a single function of the instrument 200 depending on degree of actuation (i.e. depression or sliding by a finger or thumb). For example, the instrument 200 can be configured for irrigation, fluid aspiration, and cutting. The one or more inputs 228 can be urged by a user into a position that causes the drive mechanism 205 to ramp up one or more of the actions, for example, increase the frequency of oscillation of the cutting tube 210 or aspiration pressure of the pump 245 the more the trigger is actuated by increasing the spinning of a motor). Finger-actuated instruments that are fully hand-held without any foot pedal or other tethering connection linked to the instrument provide the user with more portability, flexibility, and freedom of movement and without worrying about catching cables or other tethers during use.

Power can be supplied to the drive mechanism 205 by the power system 220 of the instrument and/or the power system 120 of the system 100 when the instrument 200 is operatively coupled to the system 100. The instrument 200 can include a cable 225 extending through a housing of the instrument 200 (see FIGS. 2A-2C). The cable 225 may also be configured to connect the instrument 200 to a wall socket. The power system 220 of the instrument 200 can include one or more batteries. The battery can be incorporated within a region of the instrument housing, internally or coupled to a region of the housing, such as within a modular, removable battery pack. The battery can have different chemical compositions or characteristics. For instance, batteries can include lead-acid, nickel cadmium, nickel metal hydride, silver-oxide, mercury oxide, lithium ion, lithium ion polymer, or other lithium chemistries. The device can also include rechargeable batteries using either a DC power-port, induction, solar cells, or the like for recharging. Power systems known in the art for powering medical devices for use in the operating room are also to be considered herein such as spring power or any other suitable internal or external power source. In some implementations, rather than the battery back mounted on or in the housing, which can increase the size of the housing, the battery pack can be mounted elsewhere such as on a user's arm or wrist of the arm holding the instrument 200 during a procedure. A short cable connector can connect the mounted battery back to the instrument 200 such that only this linkage extends from the housing of the instrument 200 during use.

Figure 2A:
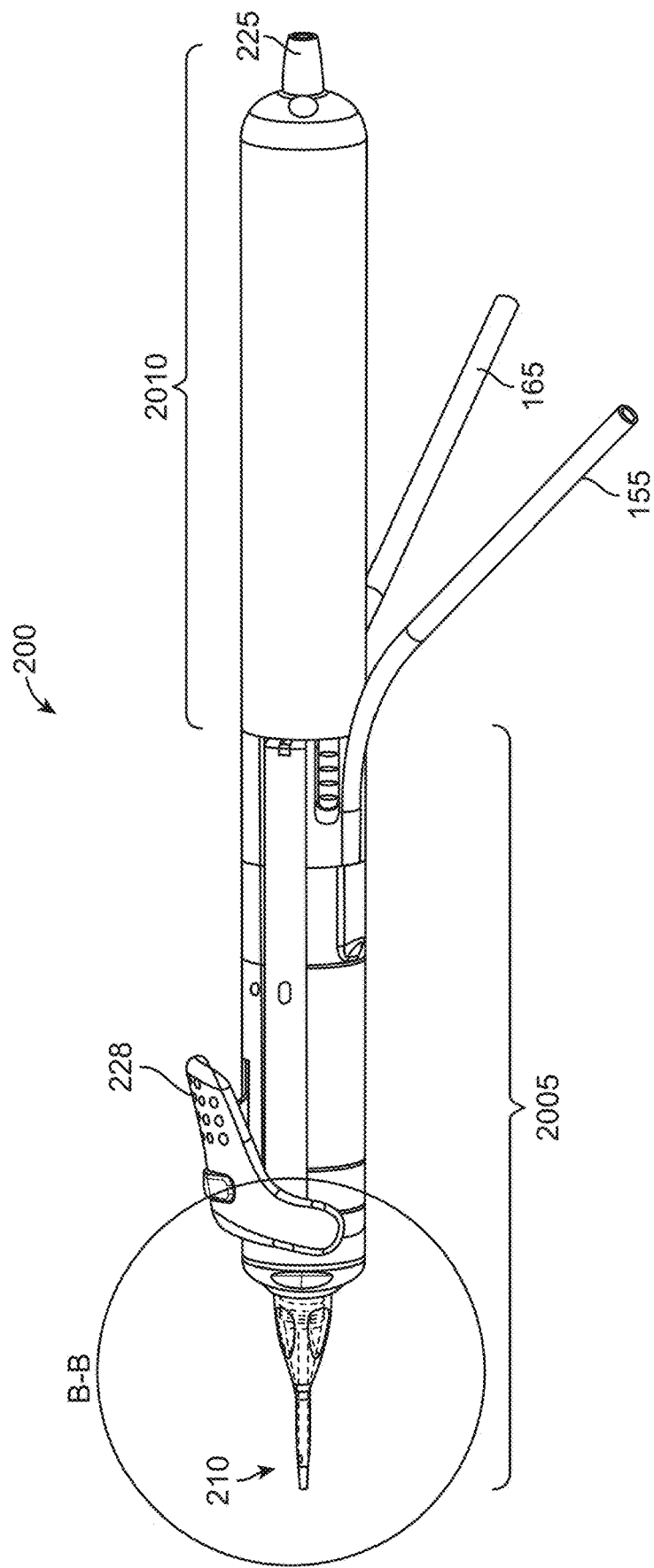
FIG. 2A shows a perspective view of an implementation of a microsurgical instrument.
Figure 2B:
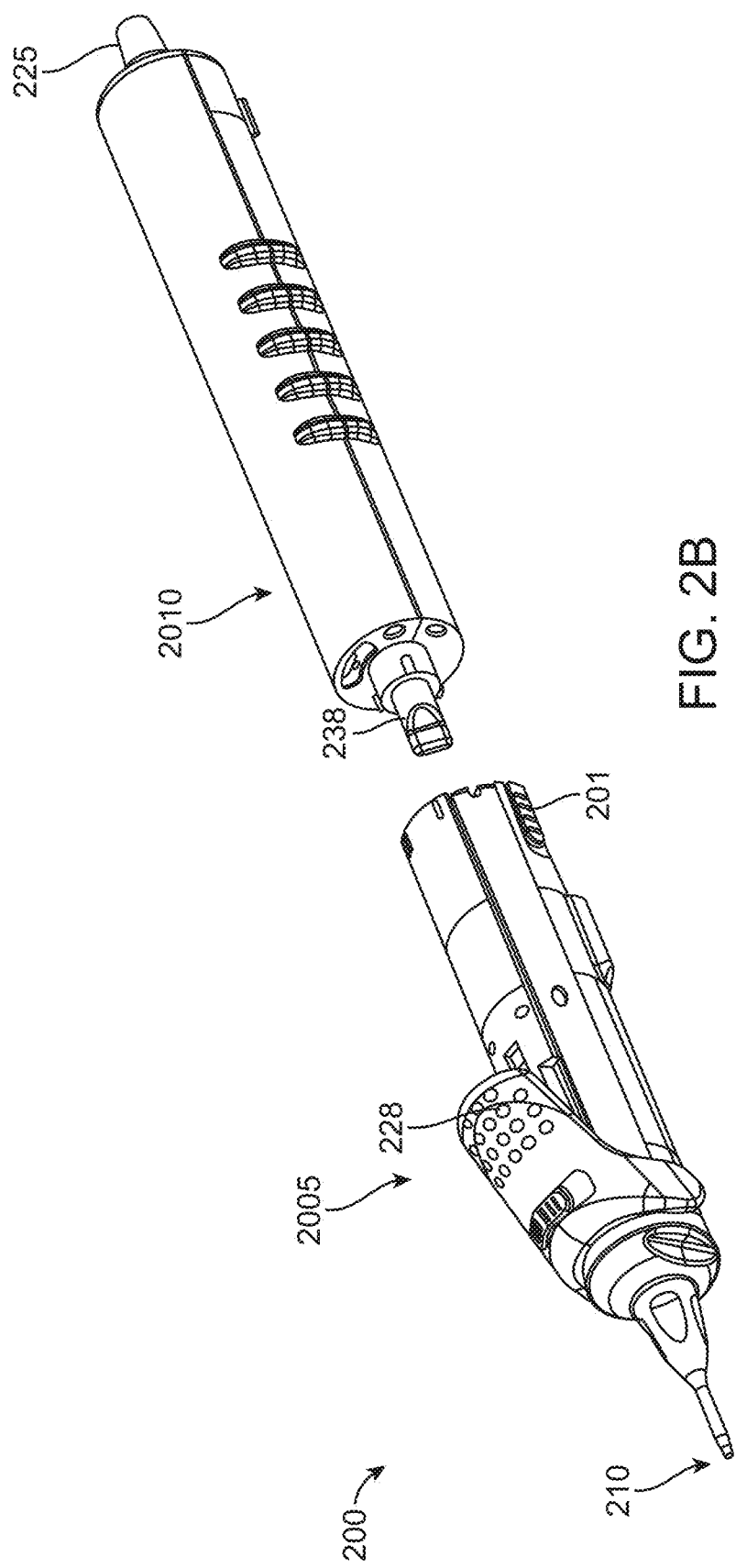
FIG. 2B shows a perspective view of the driver and working portions of the microsurgical instrument of FIG. 2A separated from one another.

FIG. 1C shows the microsurgical instrument 200 can include a disposable working portion 2005 configured to releasably operatively coupled to a durable, reusable driver portion 2010 (see also FIG. 2A-2C). Each of the disposable working portion 2005 and the reusable driver portion 2010 can include a housing portion formed of a relatively rigid, lightweight material(s). The working portion 2005 generally includes components of the instrument 200 configured to come into direct contact with fluids and materials from the eye and the driver portion 2010 of the instrument 200 generally includes the components of the instrument 200 that are configured to remain outside the fluid path. For example, the disposable working portion 2005 can incorporate the cutting tube 210 configured to be inserted into an eye to cut, aspirate, and/or inject material in the eye and a cutter assembly 214 configured to oscillate the cutting tube 210. The aspiration pump 245 as well as the connection sites for the irrigation line 155 and waste line 165, etc. (see FIG. 1A) can also be part of the disposable working portion 2005. One or more components of the drive mechanism 205, the computing unit 215, and the power system 220 may be part of the reusable driver portion 2010 of the instrument 200. The input 228 may be on the reusable driver portion 2010 or the disposable working portion 2005. The reusable driver portion 2010 may be re-sterilized and reused while the disposable working portion 2005 is not. It should be appreciated, however, that the entire instrument 200 including the reusable driver portion 2010 may also be disposable and manufactured by lower cost materials such that it is financially feasible for the driver portion 2010 to be disposed of after use.

A single reusable driver portion 2010 can be configured to operatively couple with one or more disposable working portions 2005 in an interchangeable manner. The disposable working portions 2005 can be configured for different types of procedures including lens fragmentation, emulsification, vitrectomy, bag polishing, aspiration, irrigation, coagulation, illumination, visualization, IOL insertion, and others. The disposable working portions 2005 therefore may be used for any of a variety of procedures including vitrectomy, phacoemulsification, intraocular lens insertion, etc. The operating parameters of the instrument can differ according to, for example, the disposable working portion 2005 attached to the reusable driver portion 2010 and/or the particular procedure being performed, the different stages of the procedure, the surgeon's personal preferences, whether the procedure is being performed in the anterior or posterior portion of the patient's eye, and so on. The components of the working portion 2005 can vary depending on the type of procedure and each of the different working portions 2005 regardless the procedure it is configured to perform can operatively couple and be operated by a single reusable driver portion 2010. The different disposable working portions 2005 will be described in more detail below.

FIG. 1C illustrates one implementation of a working portion 2005 operatively coupled to a driver portion 2010. The working portion 2005 can be used for procedures in which smooth flow aspiration through an oscillating cutting tube 210 is desired. Briefly, the working portion 2005 can include an aspiration pump 245 that is a linear peristaltic pump having a camshaft 405 extending along a longitudinal axis and having a plurality of lobed cams 425 (see, e.g., FIGS. 3A-3B). The camshaft 405 can be driven by the drive mechanism 205 of the driver portion 2010. The lobed cams 425 of the camshaft 405 can drive and cause motion of a plurality of cam followers 410 configured to sequentially compress tubing 415 and translate that generated aspiration pressure to the cutting tube 210 positioned within an eye. The plurality of cam followers 410 can be driven by the cams of the camshaft 405 to move in a plane that is substantially perpendicular to the longitudinal axis to compress sequentially the tubing 415. As an example, the tubing 415 can extend spatially parallel to or along the z-axis, or the center of rotation of the camshaft 405. The tubing 415 can be compressed by the cam followers 410 along an axis that is aligned substantially 90 degrees relative to the z-axis. For example, the cam followers 410 can be driven side-to-side along the horizontal position or x-axis relative to the z-axis of the camshaft 405. The cam followers 410 can also be driven along the vertical position or along the y-axis relative to the z-axis of the camshaft 405. The relative angle of the cam followers 410 and the tubing 415 can be more than or less than a 90 degree angle as well. However, the cam followers 405 do not translate axially along the sidewall of the tubing 415 (i.e. along the z-axis).

The single drive mechanism 205 rotating the camshaft 405 can also drive oscillation of the cutting tube 210, which can be a vitrectomy probe. It should be appreciated that the aspiration pump 245 can be a different type of pump (e.g. piston pump configured to apply pulsatile aspiration) and the cutting tube 210 can be a different type of probe (e.g. lens fragmentation working tip). The camshaft 405 rotated by the drive shaft 238 from the drive mechanism 205 can interface with a cutter assembly 214 resulting in oscillation of the cutting tube 210. It should be appreciated that the cutter assembly 214 and the way in which it interfaces with the camshaft 405 of the pump 245 can vary. In some implementations, the cutter assembly 214 incorporates a camming mechanism configured to cause reciprocal linear motion of the cutting tube 210. The cutter assembly 214 can include gearing to ramp up the ratio of rotations as needed between the rotations of the camshaft 405 and the number of oscillations desired in the cutting tube 210. Various configurations are described in more detail below.

Figure 1D:
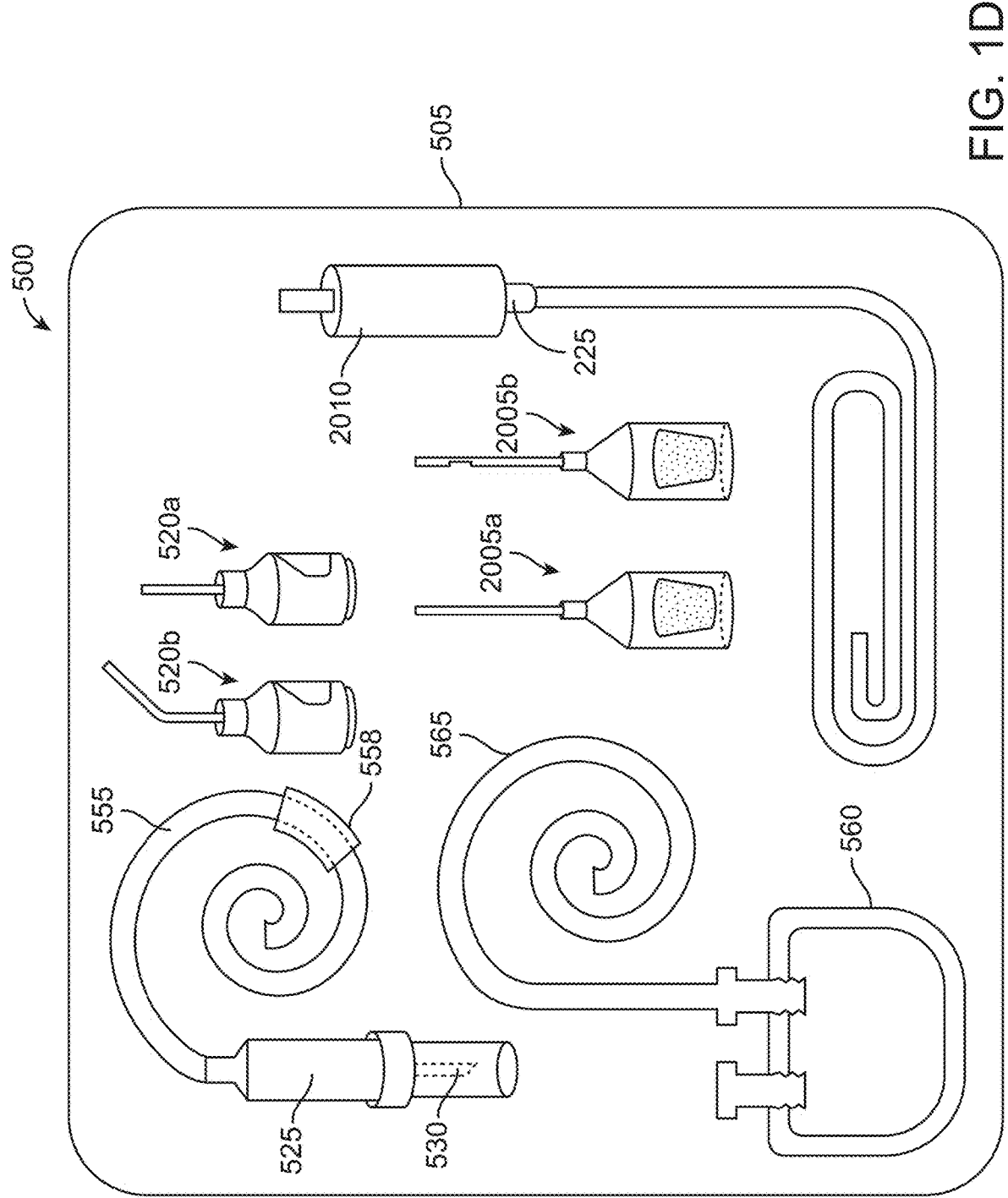
FIG. 1D shows an implementation of a kit containing a microsurgical instrument in a sterile package.

FIG. 1D illustrates an implementation of a kit 500 that includes a microsurgical instrument having one reusable driver portion 2010 configured to interchangeably couple with one or more disposable working portions 2005a, 2005b. In some implementations, a first working portion 2005a can be configured for lens fragmentation and a second working portion 2005b can be configured for vitrectomy. The first working portion 2005a can incorporate a cutting tube configured to oscillate in an asymmetric manner and a piston pump configured to generate pulsed aspiration as described in U.S. Publication No. 2018/0318132, published Nov. 8, 2018 and U.S. Publication No. 20190365567, published Dec. 5, 2019, which are each incorporated by reference herein. The second working portion 2005*b* can incorporate a cutting tube (e.g., one having a vitrectomy port) and a peristaltic pump configured to generate smooth flow aspiration, as described in more detail below. It should be appreciated that any of a variety of cutting tube configurations that are driven according to various embodiments and having any number of different pump configurations are considered herein. These are provided as examples.

A distal end region of the working portions 2005*a* can be configured to interchangeably couple with one or more working tips provided in the kit 500. For example, the kit 500 can include a lens removal working tip 520*a* and a bag polishing working tip 520*b*. The lens removal working tip 520*a* and the bag polishing working tip 520*b* can be interchanged for one another on the same disposable working portion depending on the stage of the procedure. The kit 500 can also include a drip chamber 525 having a spike 530 configured to insert within an irrigation source such as a bottle of balanced saline solution. The drip chamber 525 can be coupled to irrigation tubing 555, which in turn can couple with an irrigation coupling on the instrument 200. The irrigation tubing 555 can be provided with a pinch valve 558 that is finger-actuated in order to open and close the irrigation tubing 555. The kit 500 can also include a waste container 560 having waste tubing 565 configured to couple an outlet from the instrument 200 to the waste container 560. All the components in the kit 500 can be sterile packaged together within a single, sterile container 505.

Again, with respect to FIGS. 2A-2C showing the reusable driver portion 2010 coupled to a disposable working portion 2005. FIG. 2A shows the instrument 200 with the two portions 2005, 2010 coupled together and FIG. 2B shows the instrument 200 with the two portions 2005, 2010 separated from one another. FIG. 2C shows the reusable driver portion 2010 of the instrument 200 with a portion of the housing removed revealing components of the drive mechanism 205. In an implementation, the drive mechanism 205 can include a motor 230 with or without a gearbox or gearhead 232, a motor adaptor 236, and a drive shaft 238. The drive shaft 238 can extend through the motor adaptor 236 such that the drive shaft 238 can freely rotate with the motor 230.

The configuration of the motor 230 can vary including, any of a variety of rotation motors, stepper motor, AC motor, DC motor, a piezoelectric motor, a voice coil motor, or other motor. The motor 230 can be a brushless DC motor or any type of motor or driver suitable for rotating a shaft. The motor 230 may be an electric motor that incorporates gear reduction via the gearhead 232 or other mechanism. A harmonic drive can be incorporated to produce the desired output speed. In an implementation, a Harmonic Drive gear reduction configured to achieve at least a 30:1 reduction is incorporated. In an implementation, gearing can be incorporated to achieve an increase in output. For example, the input from the motor driving the pump can be increased via gearing to achieve an oscillation speed suitable for cutting (see FIGS. 6A-6B below). In some implementations, the gearing allows the single motor to drive rotation of two different shafts independently (see FIGS. 10, 11A-11B below).

Still with respect to FIGS. 2A-2C, the reusable driver portion 2010 can be interchangeably coupled with one or more disposable working portions 2005. The disposable working portion 2005 and reusable driver portion 2010 can couple together using a variety of mechanisms such as threads, snap-lock, bayonet, and similar mechanisms. The coupling mechanism can include a release button 201 configured to uncouple the two housing portions. The coupling between the disposable working portion 2005 and the reusable driver portion 2010 may be purely mechanical or may involve both mechanical and electronic couplings. For example, the disposable working portion 2005 may have an electronic input configured to electronically couple with a portion of the reusable driver portion 2010. Alternatively, the disposable working portion 2005 may have an input configured to mechanically couple and interact with the reusable driver portion 2010.

Figure 2D:
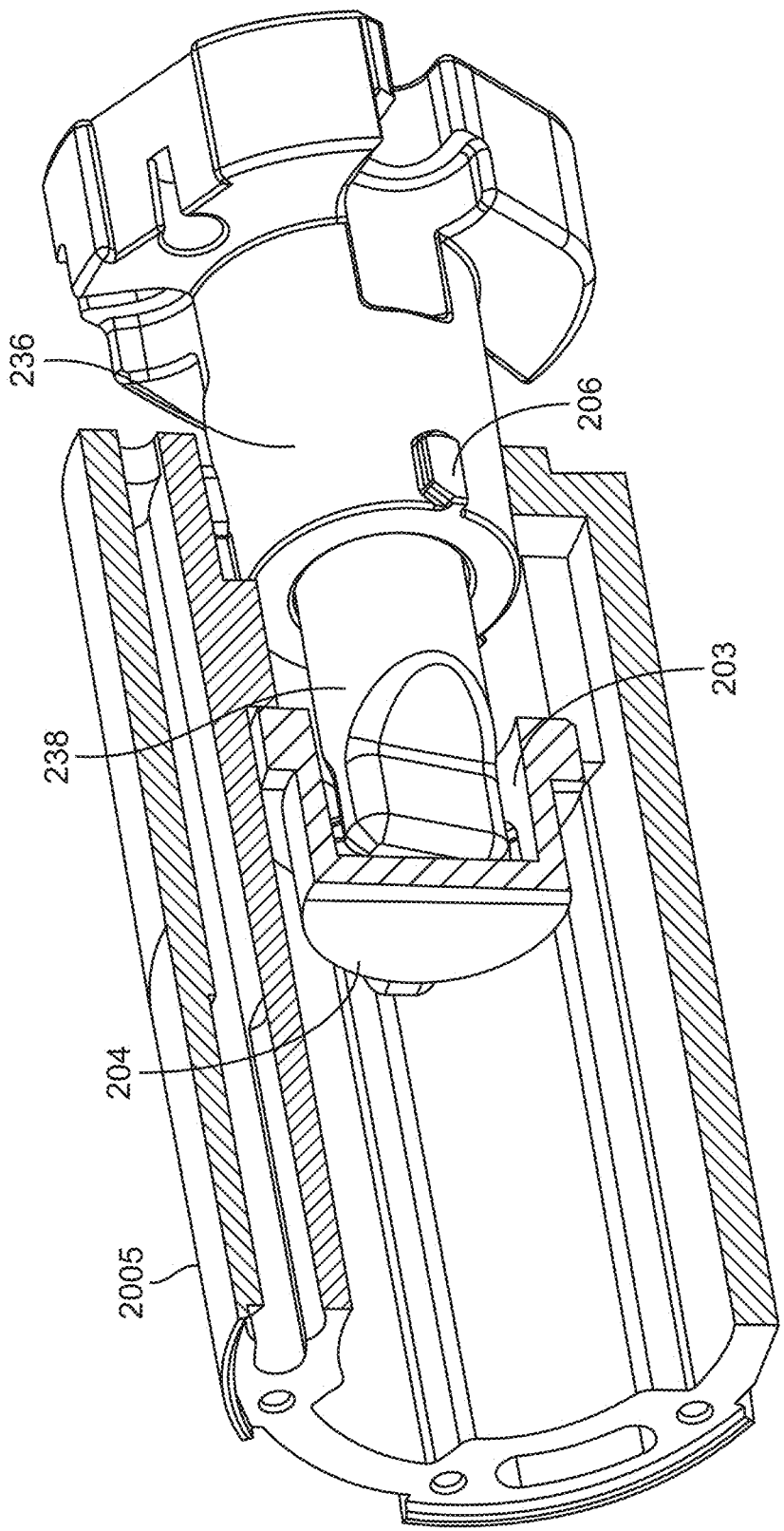
FIG. 2D shows a partial, cross-sectional view of a coupling between the driver portion and the working portions of the microsurgical instrument of FIG. 2A.

Again, with respect to FIGS. 2A-2B and also FIGS. 2C-2D the bayonet motor adaptor 236 can be fixed to the gear box 232 via plurality of motor screws 202. The drive shaft 238 of the driver portion 2010 can insert into the proximal end of the disposable working portion 2005 such that the aspiration pump 245 in the disposable working portion 2005 functionally mates with the motor 230 of the durable driver portion 2010. The drive shaft 238 can extend distal from the adaptor 236 at a distal end region of the driver portion 2010. The driver portion 2010 can insert into the proximal end of the working portion 2005 such that the end of the drive shaft 238 mates with a slot 203 on a rotating camshaft coupler 204 in the working portion 2005 (see FIG. 2D). Bosses 206 on the bayonet motor adaptor 236 can slide through L-shaped slots on the proximal end of a rear manifold of the working portion 2005. The driver portion 2010 can be rotated around the longitudinal axis relative to the working portion 2005 (i.e. clockwise) such that the bosses 206 lock the drive shaft 238 into the rear manifold in the axial direction. The bosses 206 on the bayonet motor adaptor 236 can slide into the slot 203 on the camshaft coupler 204. Once rotated, the bosses 206 on the bayonet motor adaptor 236 can lock the driver portion 2010 and working portion 2005 together in the axial direction. The release button 201 can be spring-loaded and attached to the rear manifold of the working portion 2005.

Again with respect to FIGS. 2A-2B, and also FIGS. 2C-2D, the working portion 2005 can include components of the instrument 200 configured to come into direct contact with fluids and materials from the eye whereas the driver portion 2010 generally includes the components of the instrument 200 that are configured to remain outside the fluid path, for example the components configured to drive the aspiration pump and/or the cutting element. The drive mechanism 205 of the durable driver portion 2010 is configured to drive the aspiration pump 245 integrated in the hand piece of the disposable working portion 2005. The same drive mechanism 205 can also drive the cutting tube 210. The function of the instrument can depend upon the components of disposable working portion 2005 that is coupled to the durable driver portion 2010. The configuration of the aspiration pump 245 within the disposable working portion 2005 can vary as can the type of cutting tube 210 coupled to the distal end of the disposable working portion 2005 (e.g., vitrector probe vs. lens fragmentation probe).

The configuration of the aspiration pump 245 in the disposable working portion 2005 can vary, including but not limited to bellows mechanism, diaphragm pump, venturi pump, entrapment pump, positive displacement pump, regenerative pump, momentum transfer pump, micro pumps, or the like.

In some implementations, the disposable working portion 2005 can include an aspiration pump 245 that is a piston pump. The piston pump can be configured to provide smooth continuous and/or discontinuous pulsatile aspiration, for example, as described in U.S. Publication No. 2018/0318132, published Nov. 8, 2018, which is incorporated herein by reference. The piston pump can have a plurality of pistons driven by a piston cam, which in turn is driven by the drive mechanism 205 in the reusable driver portion 2010. The pulsatile vacuum allows for application of full vacuum through the cutting tube without risk for collapse of the anterior chamber. While at the peak of the pulse, the instrument 200 can generate a high vacuum. However, since it is pulsed, the average aspiration flow rate can be low enough for the irrigation inflow to maintain proper anterior chamber support even under these high vacuums at the pulse peak. Movement of the pistons in a first direction within the pumping chambers creates a vacuum such that material from the eye is drawn into the lumen of the cutting tube. Movement of the pistons in a second, opposite direction within the pumping chambers expels material from the pumping chamber and out of the instrument. The higher flow pulsatile aspiration can be useful during lens fragmentation. The disposable working portion 2005 incorporating the piston pump can also include an oscillating working tip useful for lens fragmentation. The drive mechanism 205 of the reusable driver portion 2010 can drive both the piston pump and the oscillating working tip of the working portion 2005.

The aspiration pump can be a roller, a peristaltic, a scroll-type, a helical, a horseshoe, a rotary vane, gear, screw, diaphragm, centrifugal, or other pump type. In some implementations, the disposable working portion 2005 can include an aspiration pump 245 that is a peristaltic pump. The peristaltic pump can be configured to provide smooth continuous aspiration. The smooth continuous aspiration can be useful during anterior vitrectomy. The disposable working portion 2005 incorporating the smooth flow peristaltic pump can also include a vitrectomy probe having an inner shaft oscillating within an outer shaft as described elsewhere herein. The drive mechanism 205 of the reusable driver portion 2010 can drive both the peristaltic pump and the vitrectomy probe of the working portion 2005.

FIGS. 3A-3B show an implementation of an aspiration pump 245 for incorporation within a working portion 2005 configured to provide smooth, continuous aspiration through the cutting tube 210. The aspiration pump 245 can be a linear peristaltic pump having a symmetrical double chamber pumping manifold 420, a central camshaft 405 extending longitudinally through the manifold 420 along longitudinal axis A, a plurality of cam followers 410, and a pair of peripheral tubes 415. The pumping manifold 420 can be disposed within the working portion 2005 between a proximal manifold and a distal manifold. The camshaft 405 can couple on a proximal end region of the camshaft 405 to the drive shaft 238 such as via the rotating camshaft coupler 204 in the working portion 2005. As the pump motor 230 spins the drive shaft 238 drives rotation of the camshaft 405 thereby powering the aspiration pump 245. The camshaft 405 can also couple on a distal end region of the camshaft 405 to the cutting tube 210 such as via rotating cam follower 213. Motion of the cutting tube 210 will be described in more detail below.

Figures 4A, 4B:
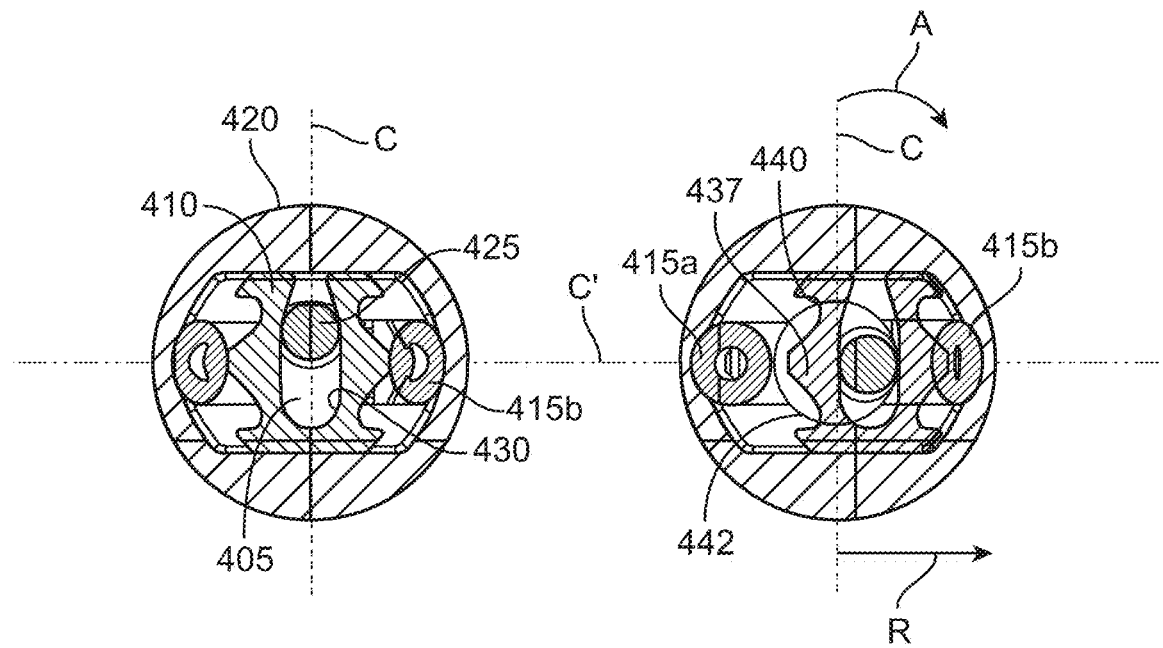
FIGS. 4A-4D show end views of the aspiration pump of FIG. 3A illustrating side-to-side motion of a cam follower as the camshaft rotates.

The two tubes 415 can be positioned on either side of a centerline C of the pumping manifold 420 (see FIG. 4A). The two tubes 415 can extend through the pumping manifold 420 in a substantially straight manner such that each forms a longitudinal axis T (see FIG. 3B) through the pumping manifold 420 that are positioned parallel with the longitudinal axis A of the camshaft 405 extending through the pumping manifold 420. A first tube 415a of the two tubes 415 can be positioned on one side of the camshaft 405 and a second tube 415b of the two tubes 415 can be positioned on a second, opposite side of the camshaft 405. A proximal flow path splits into two flow paths connected on a proximal end with the pair of tubes 415 within the proximal manifold (not shown). The two tubes 415 can combine distal to the pumping manifold 420 into the distal manifold (not shown). The distal flow path can be in fluid communication with the lumen of the distal cutting tube 210.

Figure 3C:
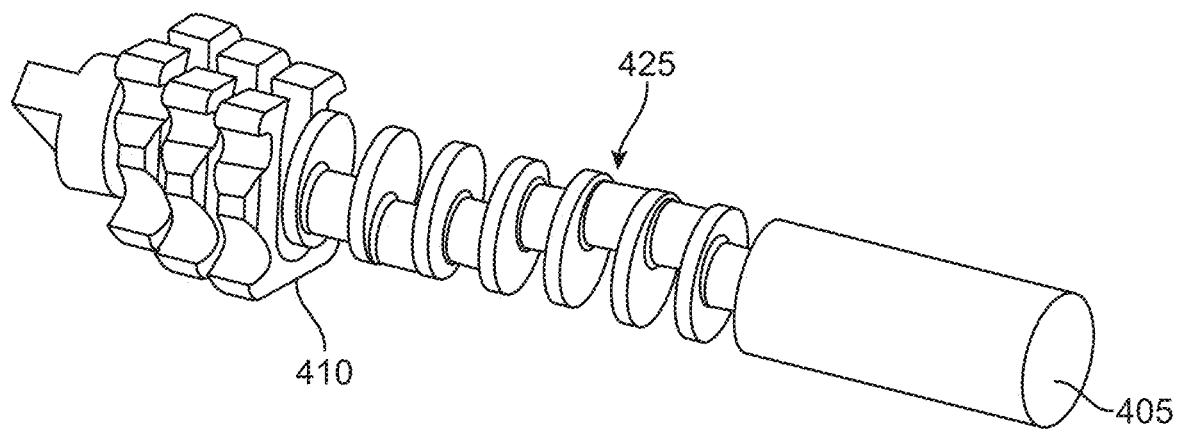
FIGS. 3C-3D show a camshaft of the aspiration pump of FIG. 3A.
Figure 3D:
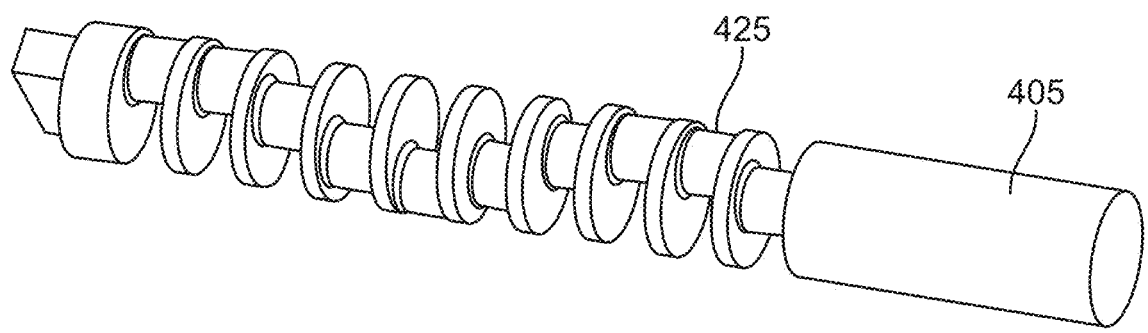

FIGS. 3C-3D show the camshaft 405 of the aspiration pump 245 in FIGS. 3A-3B.

The camshaft 405 can incorporate a plurality of lobed cams 425 that work in time to drive the plurality of cam followers 410 side-to-side or towards and away from the pair of tubes 415 such that each tube experiences sequential, progressive compression, thereby pushing its fluid volume along its flow path. The pair of tubes 415 can be aligned with the longitudinal axis A (rotational axis) of the camshaft 405. The side-to-side motion of the cam followers 410 can be in a plane perpendicular to the longitudinal axis A of the camshaft 405 and the longitudinal axis T (see FIG. 3B) of each of the tubes 415. As an example, the tubing 415 can extend spatially parallel to or along the rotational axis of camshaft 405 through the pumping manifold. The tubing 415 can be compressed by the cam followers 410 along an axis that is substantially 90 degrees relative to the rotational axis of the camshaft 405. For example, the cam followers 410 can be driven side-to-side along the horizontal position or along the vertical position relative to the camshaft 405. Although the relative angle of the cam followers 410 and the tubing 415 can be more than or less than a 90 degree angle, the cam followers 405 do not translate axially along the side wall of the tubing 415 as occurs in conventional peristaltic pumps that use rollers that compress and roll along the length of the tubing moving its fluid volume along its flow path.

Each of the tubes 415 can be sequentially compressed by the cam followers 410 in a wave-like fashion. The maximum extent of the compression closes off the tube, capturing a discrete volume of fluid that is urged along the tube's length resulting in aspiration fluid flow moving through the tubes 415. Conventional peristaltic pumps can involve the translation of a roller or other component along the longitudinal axis of the tubing thereby urging fluid through the tube. This sort of linear translation along a tube can lead to the creation of holes or tears in the sidewall of the tubing as it wears over time. The aspiration pump 245 described herein need not involve translation of a compression element along the longitudinal axis of the tubing 415 (i.e., axis T shown in FIG. 3B). Rather, the compression of each tube 415 is in a plane perpendicular to the longitudinal axis T of the tube 415. This arrangement avoids pulling or stretching of the tube and generates little to no friction on its sidewall. In other words, the plurality of cam followers apply no force along the axis of the two tubes and generate little to no friction on the two tubes. The chamber volume is maintained consistent and the pump 245 has a lower risk of tube failure or loss of pump performance that can result from compression that translates along the tube length.

Figures 4C, 4D:
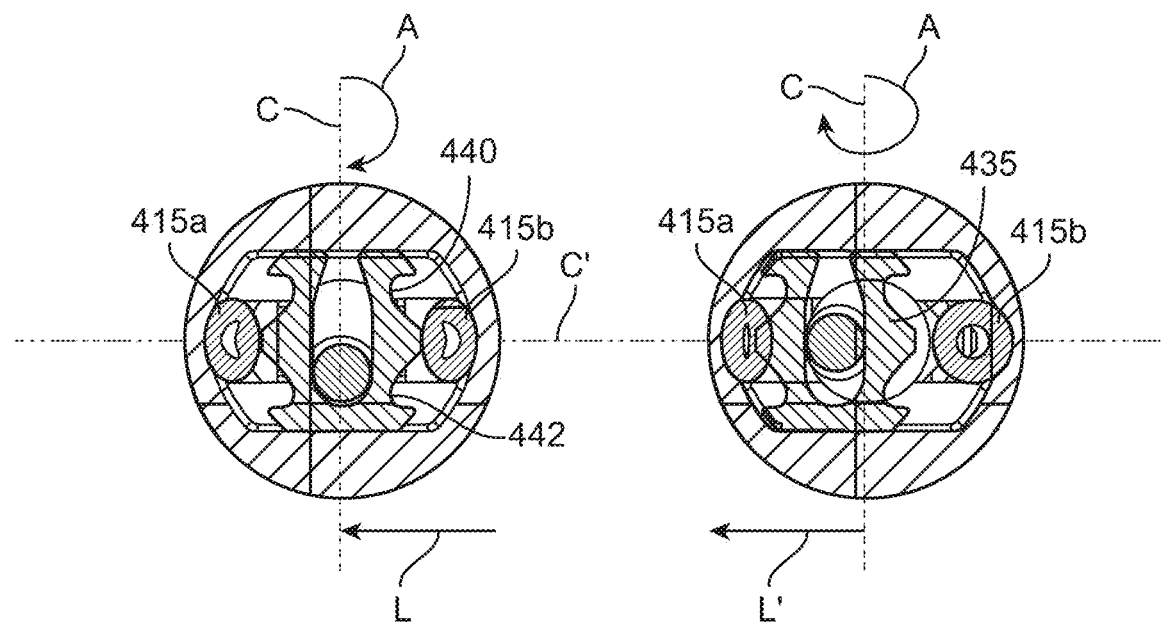

As best shown in FIGS. 4A-4D, each of the plurality of cam followers 410 can include an inner slot 430 configured to receive their respective cam lobes 425. The cam lobes 425 can travel up and down relative to and within the inner slot 430 as the camshaft 405 rotates about its longitudinal axis A. The cam followers 410 in turn are urged side-to-side by the cam lobes 425 relative to a centerline C of the pumping manifold 420. FIG. 4A shows one cam follower 410 aligned with the centerline C. The cam lobe 425 is shown substantially aligned with the centerline C and positioned in an upper end region of the slot 430 of the cam follower 410. As the camshaft 405 turns a first degree around its axis A along arrow A, the cam follower 410 is urged away from the centerline C along axis C' in the direction of arrow R and the cam lobe 425 travels downward through the slot 430 of the cam follower 410 (FIG. 4B). As the camshaft 405 turns a second further degree around its axis A along arrow A, the cam follower 410 is urged back towards the centerline C along axis C' in the direction of arrow L and cam lobe 425 travels further downward through the slot 430 of the cam follower 410 (FIG. 4C). As the camshaft 405 turns a third further degree around its axis A along arrow A, the cam follower 410 is urged away from the centerline C along axis C' in the direction of L' as cam lobe 425 travels back up through slot 430 of the cam follower 410 towards the upper end region of the slot 430 (FIG. 4D).

The side-to-side motion of the cam followers 410 can create offset pulses or incremental, sequential compression of each tube 415 such that the aspiration created in the distal flow path that is in communication with the cutting tube is smooth or substantially non-pulsatile aspiration. The geometry of the camshaft 405 (e.g. pitch, length) as well as the number of cam lobes 425 and cam followers 410 can vary to achieve a particular timing along the longitudinal axis T of the tubes 415. The number of cam followers 410 in the pump 245 can vary, for example, at least 2, 3, 4, 5, 6, 7, 8, 9, 10, up to about 20 cam followers 410. The number of cam lobes 425 and cam followers 410 can more closely approximate perfect smooth flow as the number of lobes and followers increases. For example, the implementation of the aspiration pump 245 shown in FIG. 3B includes 10 cam lobes 425 and 10 cam followers 410. The aspiration pump 245 can thereby create a smooth, sine wave sort of curve as each cam follower 410 is urged side-to-side to compress the opposing tubes 415.

Figure 5A:
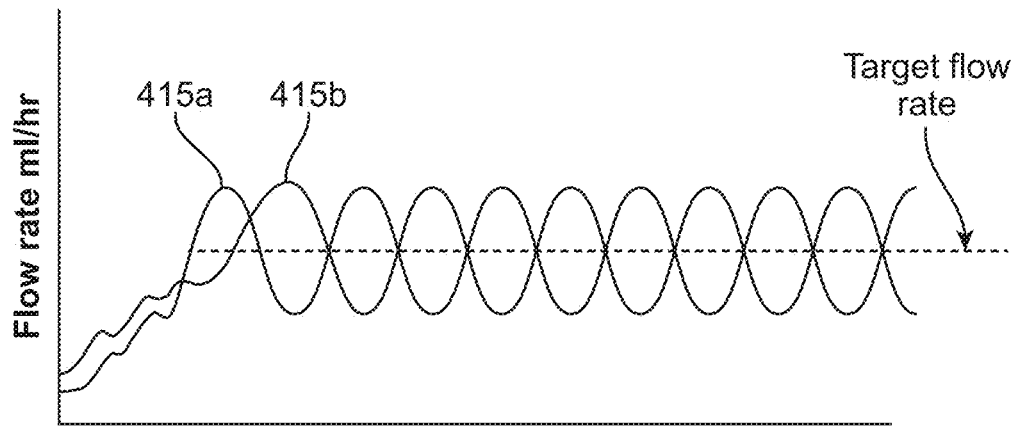
FIG. 5A shows an example of aspiration flow rate provided by an aspiration pump.

FIG. 5A shows how initially, the pump 245 can undergo a warm-up period upon activation as the camshaft 405 starts rotating. The cam followers 410 are urged side-to-side within the pumping manifold 420 to compress sequentially the pair of tubes 415 and the negative pressure within the flow line of tube 415a and tube 415b builds. The flow rate through tube 415a can be offset from the flow rate through tube 415b such that the target flow rate achieved is substantially constant with minimal pulsatile flow through the distal flow path.

Figure 5B:
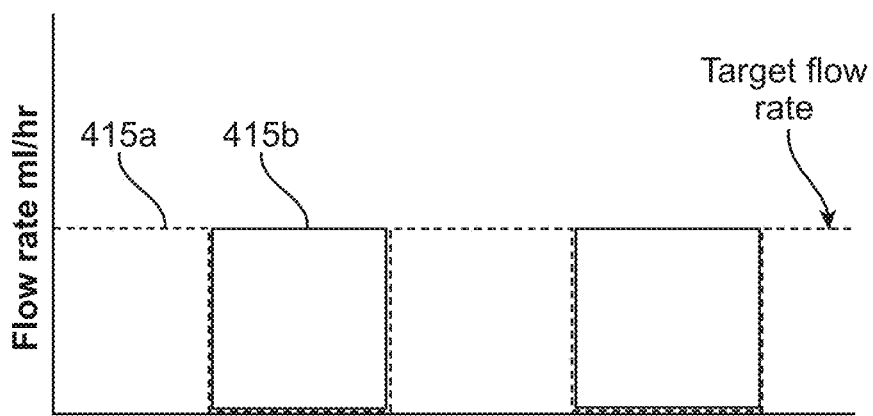
FIG. 5B shows another example of aspiration flow rate provided by an aspiration pump.

The pump 245 can include fewer cam followers 410 than is shown in the embodiment of FIGS. 3A-3B. In such an implementation, the timing of the camshaft 405 can create a curve that is more like an off-on type of square curve (see FIG. 5B). The on-off square curve can provide a more consistent chamber length (i.e., the sealed volume within the tubing between the locations where the tube is closed off by the cam followers) compared to, for example, a helical driven peristaltic pump where the tube is squeezed shut using a more gradual motion. The cam lobes of the implementation of the pump shown in FIGS. 3A-3B follow a circular path relative to the device at large and a linear path relative to the cam followers 410. The cam followers compress the tubes on both sides. As it moves one direction, the compresses one tube and as it moves in the opposite direction, it compresses the opposite tube. However, the cam lobes need not be driven by a helical path with such gradual compression. Rather, the layout of the cam lobes can be positioned radially or lengthwise along axis T relative to one another such that the spacing between each cam lobe can create compression on the tube 415 to achieve the desired timing.

Again, with respect to FIGS. 4A-4D, the shape of the cam followers 410 not only provides for the travel of the cam followers 410 in a side-to-side motion as the camshaft 405 spins. The shape of the cam followers 410 provides efficient compression of the pair of tubes 415. Each cam follower 410 can incorporate a first compression zone 435 on an outer surface of the cam follower 410 on a first side of centerline C and a second compression zone 437 on an outer surface of the cam follower 410 on a second, opposite side of centerline C. Each of the first and second compression zones 435, 437 can be arranged substantially aligned with the centerline C'. As the cam follower 410 moves along arrow R, the first compression zone 435 compresses tube 415b (FIG. 4B). As the cam follower 410 moves along arrow L', the second compression zone 437 compresses tube 415a (FIG. 4D). Each cam follower 410 can also include two displacement zones 440, 442 for each compression zone 435, 437. As the tubes 415 are compressed by the compression zones 435, 437, the corresponding two displacement zones 440, 442 can receive the material of the tubes 415 that are being compressed by the compression zones 435, 437 of the cam follower 410.

The pair of tubes 415 can extend in a straight line along longitudinal axis T and parallel with the longitudinal axis A of the camshaft 405. The pair of tubes 415 extend generally parallel to the rotational axis of the camshaft 405 through the pumping manifold. As such, the compression on the tubes 415 occurs in a side-to-side motion along a horizontal plane relative to the rotational plane of the camshaft, which can be in a plane perpendicular to the longitudinal axis A (and also axis T). This compression does not therefore translate axially along the sidewall of the tubing thereby providing the advantage of less wear on the tubing material. Additionally, the configuration of the pair of straight tubes 415 can provide additional side-to-side force on the cam follower 410. For example, as one tube 415a is being compressed by the cam follower 410, the opposing tube 415b that just was compressed by a cam follower 410 can spring back to its original shape. The spring force can help to compress the opposing tube 415. Each tube 415 can aid in causing compression of its partner by urging the cam follower 410 in the opposite direction of the compression.

The configuration of the peristaltic pump within the working portion 2005 can vary and need not be a linear peristaltic pump. For example, the peristaltic pump can be a helical design or a horseshoe peristaltic pump.

In the context of cataract surgery, vitrectomy is used when a complication occurs during lens removal, for example, inadvertent prolapse of vitreous into the anterior segment after rupture of the posterior capsule. Vitrectomy is generally considered an unwelcome part of cataract surgery. The goal of anterior vitrectomy is to remove the vitreous from the anterior chamber, to clear vitreous from entry incisions, and to allow an intraocular lens to be inserted. Vitreous has an unpredictable flow behavior that is difficult to characterize due to its semi-solid structure. Vitreous is composed of mostly water, but also collagen fiber and hyaluronic acid. Vitreous requires cutting before going through the probe. Chopped vitreous has a lower viscosity than intact gel-like vitreous. Small bite sizes pieces are preferred to improve aspiration and removal of vitreous.

The cutting tube 210 and aspiration pump 245 can be driven to achieve low level cutting (e.g. 300 cpm) and low level aspiration (e.g. less than about 3 cc/min), for example, to remove lens fragments from the eye prior to initiation of vitreous removal. The cutting tube 210 and aspiration pump 245 can be driven to achieve higher-level cutting (e.g. 500-600 cpm) with low to moderate aspiration (e.g. 3 cc/min to about 10 cc/min) for vitreous removal and to cause vitreous to flow continuously into the cutter. The cutting tube 210 and aspiration pump 245 can be driven to achieve high-level cutting (e.g. up to about 7,500 cpm) with high aspiration (e.g. greater than 10 cc/min up to about 25 cc/min) for vitreous removal and to cause vitreous to flow continuously into the cutter. In other implementations, the cutting tube 210 and aspiration pump 245 can be drive to achieve asymmetric cutting and high, pulsatile aspiration (e.g., greater than 10 cc/min up to about 30 cc/min or up to about 100 cc/min), for example, useful for lens fragmentation and emulsification. The motion profiles and aspiration profiles can vary depending on the procedure being performed and the stage of the procedure itself.

Figure 6A:
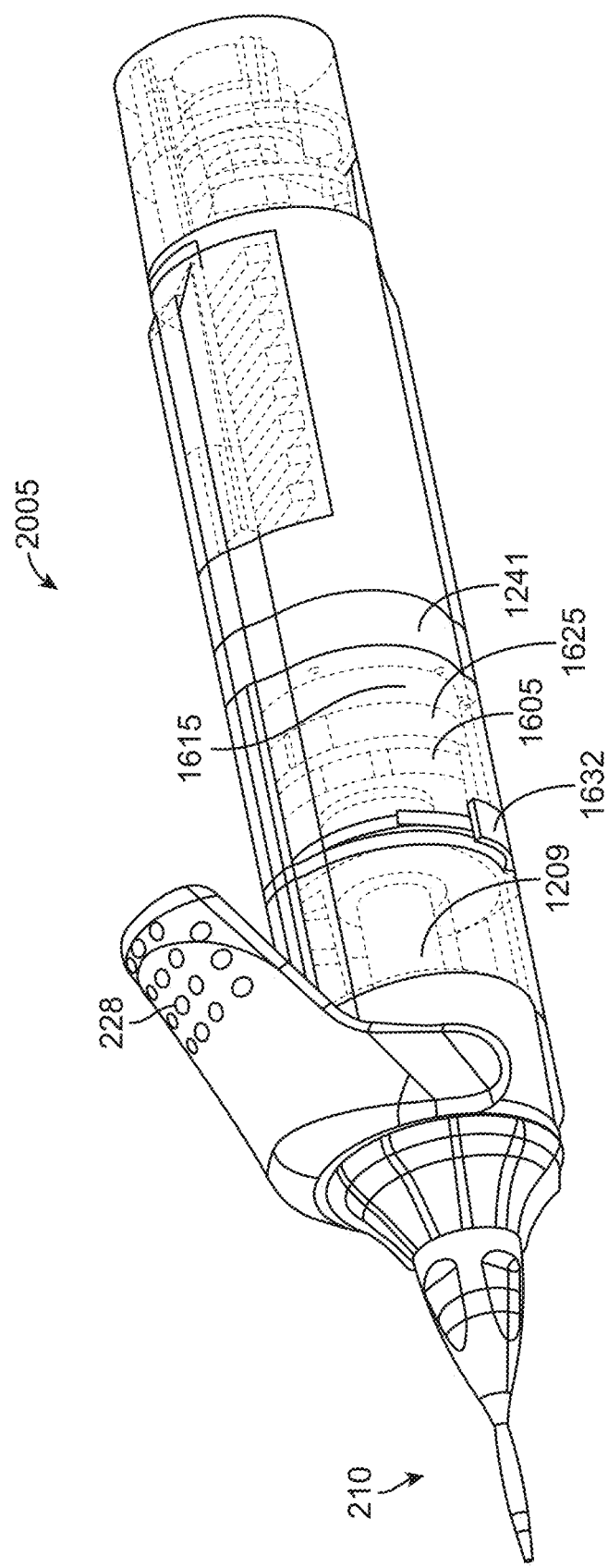
FIG. 6A and FIG. 6B shows perspective and cross-sectional view, respectively, of another implementation of a working portion of a microsurgical instrument.
Figure 6B:
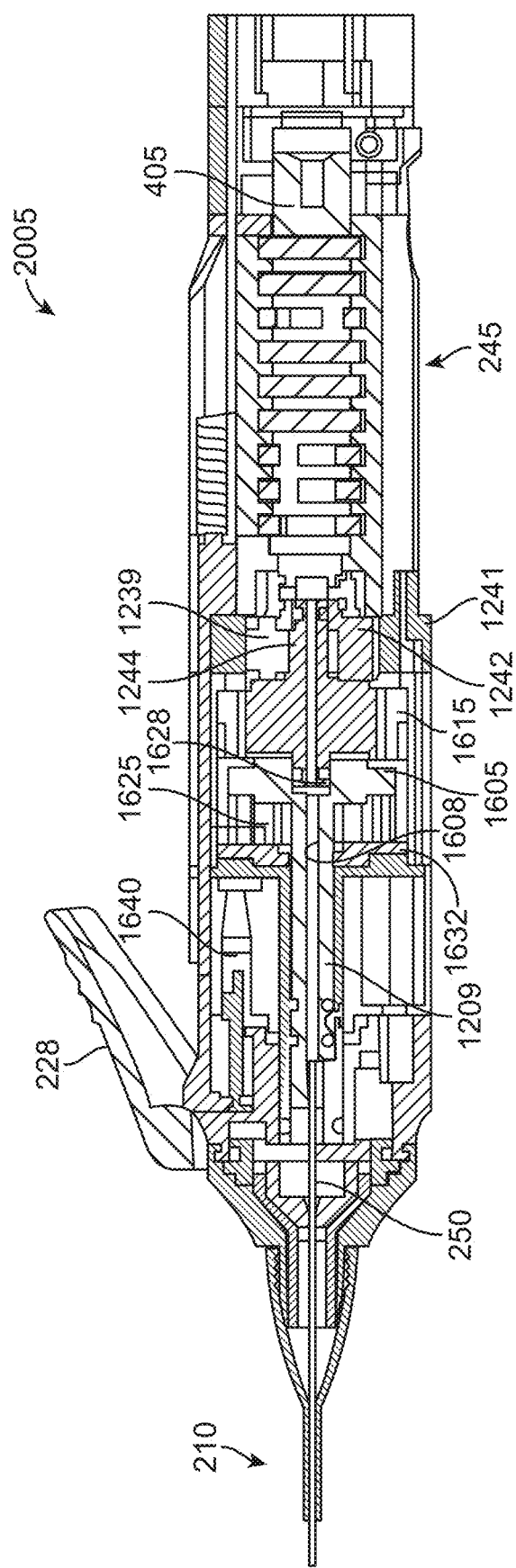

FIGS. 6A-6B illustrate a disposable working portion 2005 of a microsurgical instrument 200 having an integrated aspiration pump 245 that is a linear peristaltic aspiration pump 245 as described above. The disposable working portion 2005 can be configured to perform anterior vitrectomy and can coupled with a reusable, driver portion 2010 that incorporates any of a variety of features described herein. Thus, a single reusable, driver portion 2010 can drive different working portions 2005 having different functional capabilities (e.g., lens fragmentation, vitrectomy, bag polishing, etc.).

The cutting tube 210 can have any of a variety of configurations such that it can be used for lens fragmentation, lens emulsification, vitrectomy, and other anterior segment procedures. Generally, the cutting tube 210 has a maximum cross-sectional diameter that is suitable for minimally invasive procedures in the eye to minimize the corneal incision size. In some implementations, the maximum cross-sectional diameter of the cutting tube 210 is about 1.25 mm. The maximum cross-sectional diameter can be smaller than this or can be larger than this diameter, for example, no more than about 2 mm in diameter, no more than about 3 mm in diameter, up to about 4 mm in diameter, or up to about 5 mm in diameter. The cutting tube 210 can be a 20 gauge, a 23 gauge, a 25 gauge, or a 27 gauge vitrectomy probe as known in the art.

Figure 7A:
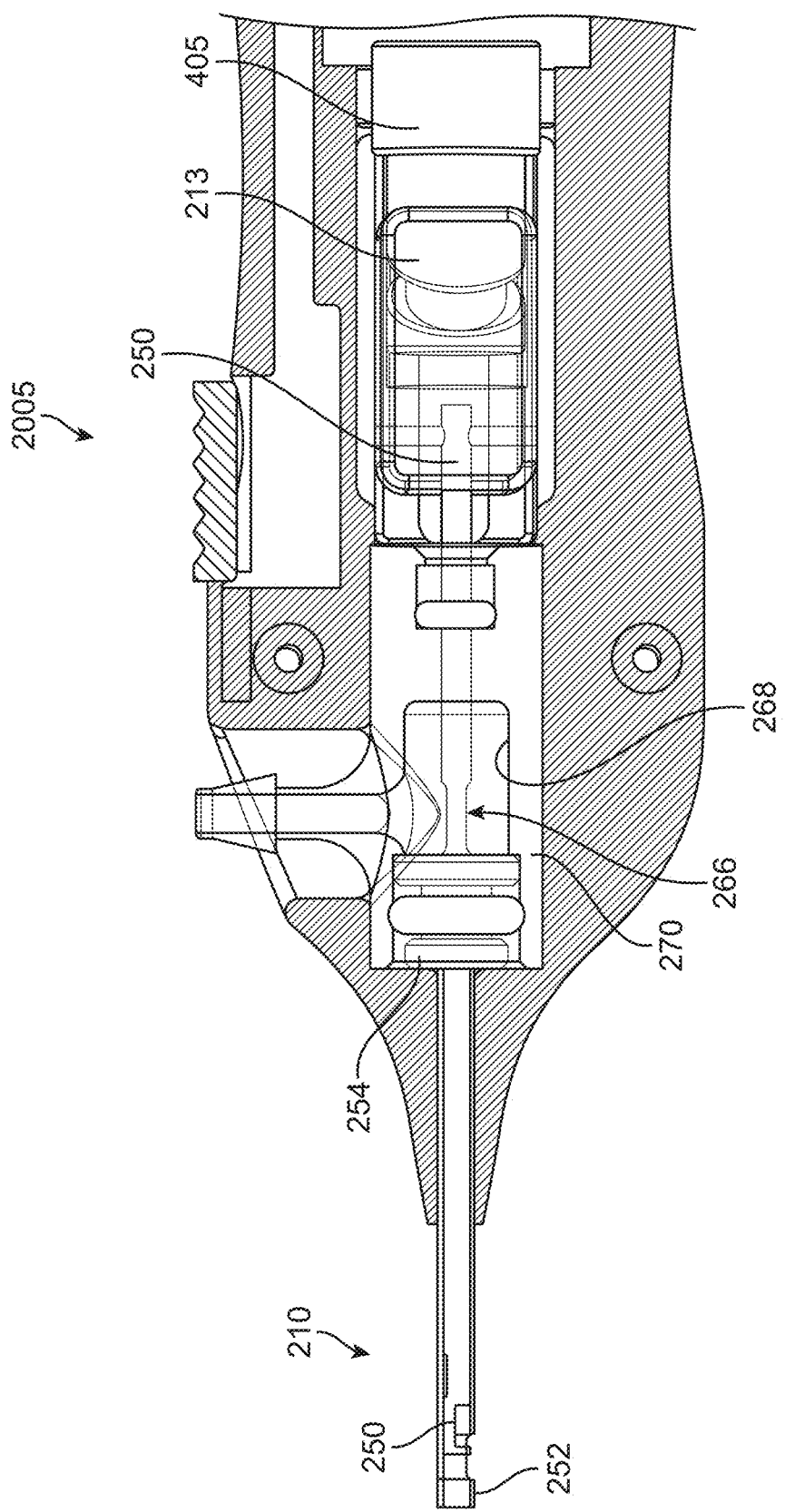
FIG. 7A shows a cross-sectional partial view of an implementation of a microsurgical instrument for cutting and aspirating lens material from an eye.
Figure 7B:
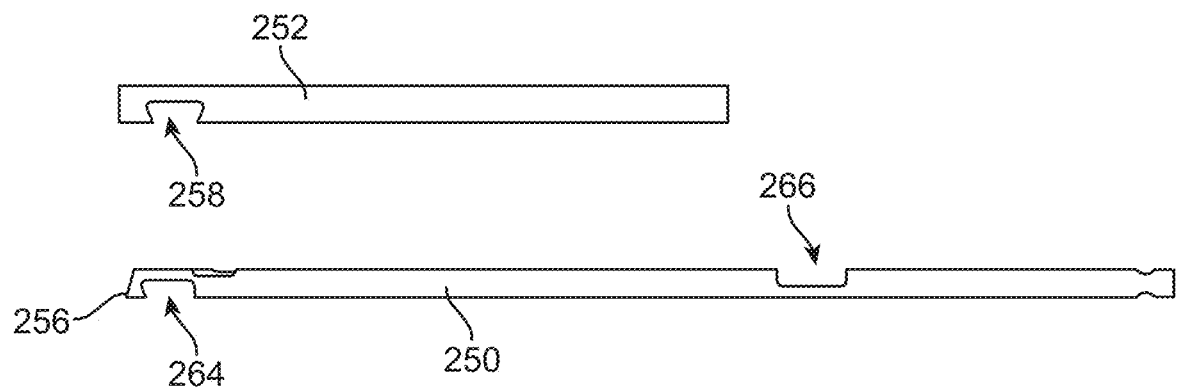
FIGS. 7B-7C shows exploded and assembled views, respectively, of the cutting tube of the microsurgical instrument shown in FIG. 7A.
Figure 7C:
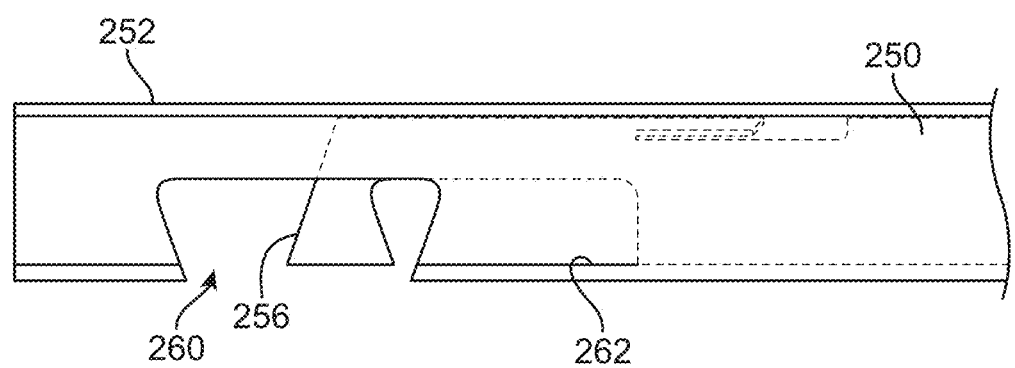

In some implementations, the cutting tube 210 is a standard guillotine-shaped vitrectomy probe having an inner tubular elongate member 250 configured to slide reciprocally within an outer tube 252 (see FIGS. 7A-7C). The outer tube 252 can be a stationary tubular element coupled to a region of the working portion 2005. The outer tube 252 can be fixedly coupled within an interior of the working portion 2005 by a retainer 254. The retainer 254 can be a donut-shaped element configured to receive the outer tube 252 therethrough such that the retainer 254 is positioned about a proximal end region of the outer tube 252. The elongate member 250 can also be a tubular element, but unlike the outer tube 252, is movable such that it can be oscillated within the lumen of the outer tube 252.

A distal tip of the elongate member 250 can be formed into a cutting edge 256 (see FIG. 7C). In some implementations, the cutting edge 256 is a short, sharpened bevel. Together, the cutting edge 256 of the elongate member 250 and the opening 258 in a sidewall of the outer tube 252 form a port 260. The port 260 can vary in size depending on the position of the elongate member 250 relative to the outer tube 252. In operation, tissue may enter into the cutting tube 210 through the port 260 and be dissected by the cutting edge 256 as the elongate member 250 is reciprocated within the outer tube 252. Vitreous enters the port 260 upon drawing aspiration through the lumen 262. The oscillating inner elongate member 250 can trap lens material between cutting edge 256 and the opening 264 to cut small pieces of the lens material drawn into the port 260 as the elongate member 250 moves distally. If the elongate member 250 has no side opening, the port 260 can undergo a complete closure as the elongate member 250 moves distally past side opening 264. This closure of the port 260 can result in flow instability, fluid acceleration, and retinal traction. Thus, the elongate member 250 can also incorporate a side opening 258 near its distal end regions. This configuration is described as a two-dimensional cutter that has an increased cutting rate and overall better efficiency while also improving retinal traction problems. As the inner elongate member 250 oscillates within the outer tube 252, the distal shaft edge 256 can chop vitreous that enters the port on a distal stroke. On a proximal stroke of the elongate member 250, vitreous that enters the opening 258 can also be chopped. The double-port two-dimensional cutters can increase the amount of cutting achieve in a single back-and-forth motion of the inner elongate member 250 and avoids closing off the port 260 completely.

The port 260 can have a width that is optimized for fully chopping and aspirating the eye tissue. In some implementations, the port 260 can have an axial length that is greater than 0.05" up to about 0.175". The port 260 can have a width that can be between 0.015" and 0.06". The distal tip of the outer tube 252 can be sharp as shown in FIG. 7C or can be blunt-tipped or bullet-shaped. The port 260 can be biased to remain in an open position to avoid snagging tissue during removal of the instrument. The cut rate achieved can vary as is known in the art, for example, up to about 7,500 cuts per minute (cpm). The duty cycle of the probe can be controlled, for example, using the finger trigger type input 228 of the instrument as well as another input described herein.

In some implementations, the lumen 262 extends through the elongate member 250 to a proximal opening 266 (see FIGS. 7A-7B). The proximal opening 266 is maintained within a chamber 268 of a vacuum manifold 270 that is in fluid communication with the distal aspiration line from the aspiration pump 245. The proximal opening 266 is maintained within this chamber 268 during oscillating movements of the elongate member 250. A vacuum is applied by the aspiration pump 245 within the vacuum manifold 270 to aspirate the dissected tissue from the eye through the lumen 262. The dissected tissue enters the lumen 262 at port 260 and exits the lumen 262 through the proximal opening 266.

As described above, the pump 245 can include a camshaft 405 extending along a longitudinal axis of the housing. The camshaft 405 can be driven by a drive mechanism of the driver portion 2010 (not shown). The proximal end region of the camshaft 405 can couple to the drive shaft 238 such as via the coupler 204 in the disposable working portion 2005 and the distal end of the camshaft 405 can operatively couple with the cutting tube 210. Thus, the drive mechanism 205 that drives the aspiration pump 245 can also drive oscillation of the cutting tube 210. The oscillation drive mechanism can incorporate a cam assembly to convert the rotary motion of the camshaft 405 into linear motion of the cutting tube 210.

Figure 7D:
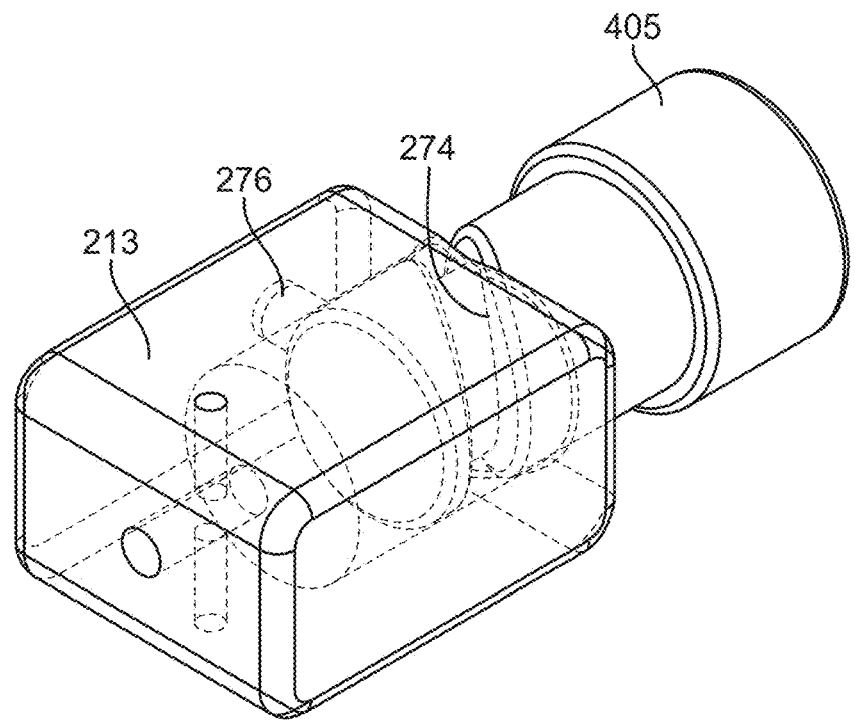
FIGS. 7D-7E shows a cam mechanism configured to oscillate the cutting tube of the microsurgical tool implementation shown in FIG. 7A.
Figure 7E:
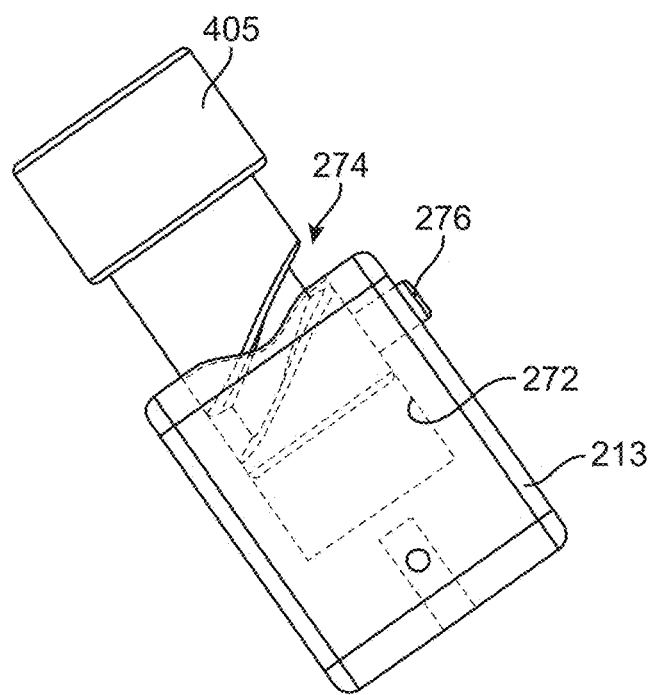

FIGS. 7A-7E illustrate an implementation of a cutter cam assembly 214 configured to oscillate the cutting tube 210. The cutter assembly is provided as an example and can vary. In some implementations, the cutter assembly is configured for lens fragmentation and can achieve an asymmetric motion profile as described in U.S. Pat. No. 10,231,870, published Mar. 19, 2019. In other implementations, the cutter assembly is configured for anterior vitrectomy. The cutter assembly 214 can include a cutter cam follower 213 configured to move axially along the longitudinal axis A as the camshaft 420 rotates. FIG. 7A shows a distal end region of the camshaft 405 (i.e. distal to the pumping manifold 420) engaged with the cutter cam follower 213 and the cutter cam follower 213 fixedly coupled to a proximal end of the elongate member 250. The rotary motion of the camshaft 405 is converted to linear motion of the cutter cam follower 213 and thus, linear motion of the elongate member 250. FIGS. 7D-7E show the cutter cam follower 213 can have a bore 272 in a proximal end configured to receive the distal end of the camshaft 405. The outer surface of the distal end of the camshaft 405 can include a channel 274 configured to receive a corresponding pin element 276 of the cutter cam follower 213. As the camshaft 405 turns around its longitudinal axis A, the pin element 276 moves through the channel 274 around the outside surface of the camshaft 405. The channel 274 can follow an elliptical path from a first proximal end region towards a distal end region and back toward the first proximal end region. As the pin element 276 moves through the channel 274, the cutter cam follower 213 is urged to move axially along a longitudinal axis A. The cutter cam follower 213 moves in a distal direction for at least a fraction of the rotation. The cutter cam follower 213 then moves in a proximal direction for at least another fraction of the rotation. As such, a complete revolution of the camshaft 405 provides reciprocating axial movement of the cutter cam follower 213 and the elongate member 250. It should be appreciated that other drive mechanisms to create oscillating movements of the elongate member 250 of the cutting tube 210 are considered herein.

In another implementation, the cam assembly can include a ramp cam incorporating asymmetric or symmetric profiles. The elongate member 250 of the cutting tube 210 configured to translate along the longitudinal axis of the instrument can interface with the ramp cam configured to rotate. In some implementations, the ramp cam incorporates a simple saw tooth configuration having an asymmetric profile. In other implementations, the ramp cam incorporates a double ramp cam with a symmetric plateau and valley. The ramp cam can incorporate a cutter return spring. The backward (proximal motion) of the elongate member 250 be a function of the ramp profile and the forward (distal motion) of the elongate member 250 can be a function of the cutter return spring. The elongate member 250 can pop back and forth over the ramp cam as the ramp cam rotates for oscillating movements.

The RPMs of the motor can be increased by incorporating a gearbox. The gearing can have a ratio that increases the input at least about 3:1, 4:1, 5:1, 6:1, up to about 30:1. For example, the gearing can be a single stage 5:1 planetary gear drive, to increase the rate of rotation from 140 RPM input to approximately 700 RPM. The gear ratio can be driven by the cam profile and spacing for the ramp angle driving the speed of 2 ms and the dwell of approximately 4 ms. The cam can be designed to ensure the cutting stops the elongate member 250 of the cutting tube 210 in an open position relative to the outer tube. It should be appreciated that the oscillation drive mechanism can incorporate other cam configurations including an acentric cam, barrel cam, or helical cam.

The oscillation drive mechanism need not incorporate a cam and instead can rely on magnetic forces to achieve the linear motion of the elongate member 250 of the cutting tube 210. The magnetic drive can rely on the push-and-pull magnetic array for linear translation of the elongate member 250 of the cutting tube 210 and avoids use of springs. The cutting tube oscillation achieved by the magnetic drive is relatively smooth and has very little vibration and noise. Similar to pneumatic drive systems, the speed of the elongate member 250 of the cutting tube 210 in the magnetic drive is force-driven and not dependent on the rotational speed. The 140 rpm input speed can achieve a frequency of 6 Hz.

Again with respect to FIG. 6B and FIGS. 8A-8B, the elongate member 250 of the cutting tube 210 can be coupled to a cutter spline 1209 having a translating magnet disc 1605 on a proximal end. The cutter spline 1209 and the translating magnet disc 1605 are free to move bidirectionally a distance axially along a longitudinal axis of the housing in a proximal and distal direction in response to motion of the camshaft 405 while prevented from rotating around the longitudinal axis. The translating magnet disc 1605 can include one or more magnets configured to interact with one or more magnets of a rotating magnet disc 1615 positioned proximal to the translating magnet disc 1605 to create a local magnetic field. The rotating magnet disc 1615 is configured to rotate, for example, with the rotation of the camshaft 405 of the pump 245, preferably with a gearbox positioned therebetween. The one or more magnets of the rotating magnet disc 1615 spin in and out of alignment with the one or more magnets of the translating magnet disc 1605. The magnetic forces between the magnets of the rotating magnet disc 1615 and the magnets of the translating magnet disc 1605 cause the translating magnet disc 1605 (and thus, the cutting tube 210) to oscillate back and forth relative to the housing. The oscillation can be achieved by magnetic attraction and/or magnetic repulsion. For example, the rotating magnet disc 1615 can have a first magnet having a positive pole positioned towards a distal end of the housing. The translating magnet disc 1605, positioned within the housing at a location distal to the rotating magnet disc 1615, can have a second magnet having a negative pole positioned towards a proximal end of the housing. The first magnet of the rotating magnet disc 1615 and the second magnet of the translating magnet disc 1605 can align with one another upon rotation of the rotating magnet disc 1625 an increment of the circumference around the longitudinal axis. Once aligned, the first and second magnets can magnetically attract to achieve linear translation of the cutter spline 1209 in a first direction. The next increment of the circumference around the longitudinal axis aligns the poles of the magnets on their respective magnet discs 1605, 1615 to repel one another to achieve linear translation of the cutter spline 1209 in a second, opposite direction. As the rotating magnet disc 1615 continues to spin relative to the translating magnet disc 1605 magnetic forces alternate between them to achieve reciprocal linear motion. Thus, rotation of the rotating magnet disc 1615 relative to the translating magnet disc 1605 causes the poles of the plurality of magnets of the rotating magnet disc 1615 to cause alternating repulsion and attraction with the one or more magnets of the translation magnet disc 1605 causing oscillation of the elongate member 250 of the cutting tube 210.

Figure 8B:
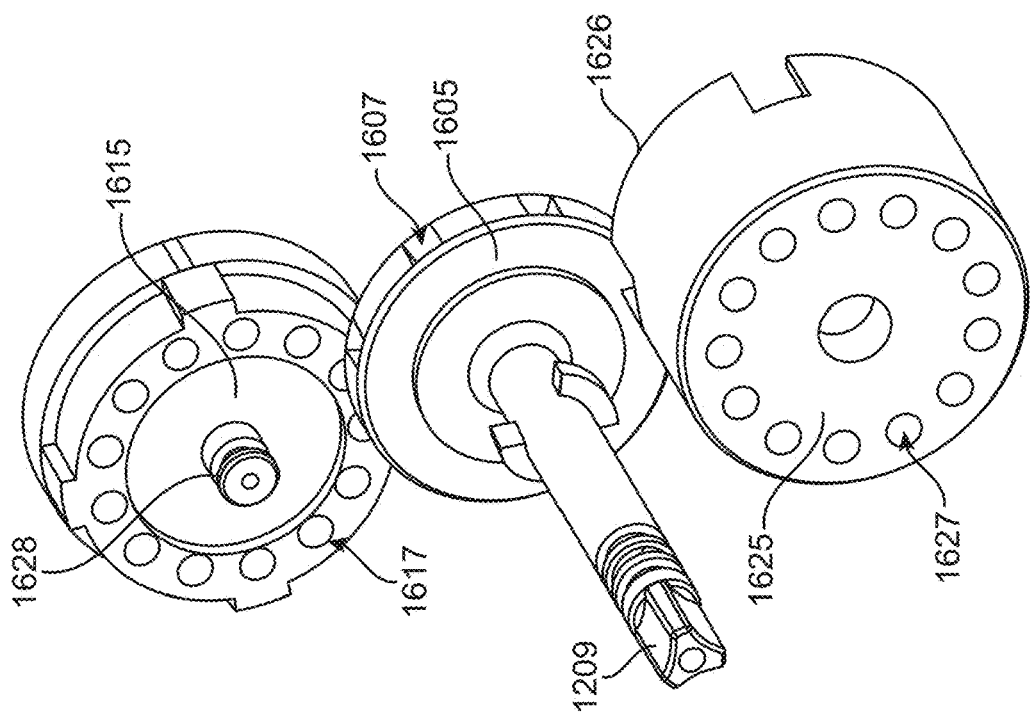
FIGS. 8A-8B show exploded views of a magnetic drive configured to oscillate the cutting tube of the microsurgical tool implementation shown in FIGS. 6A-6B.
Figure 8A:
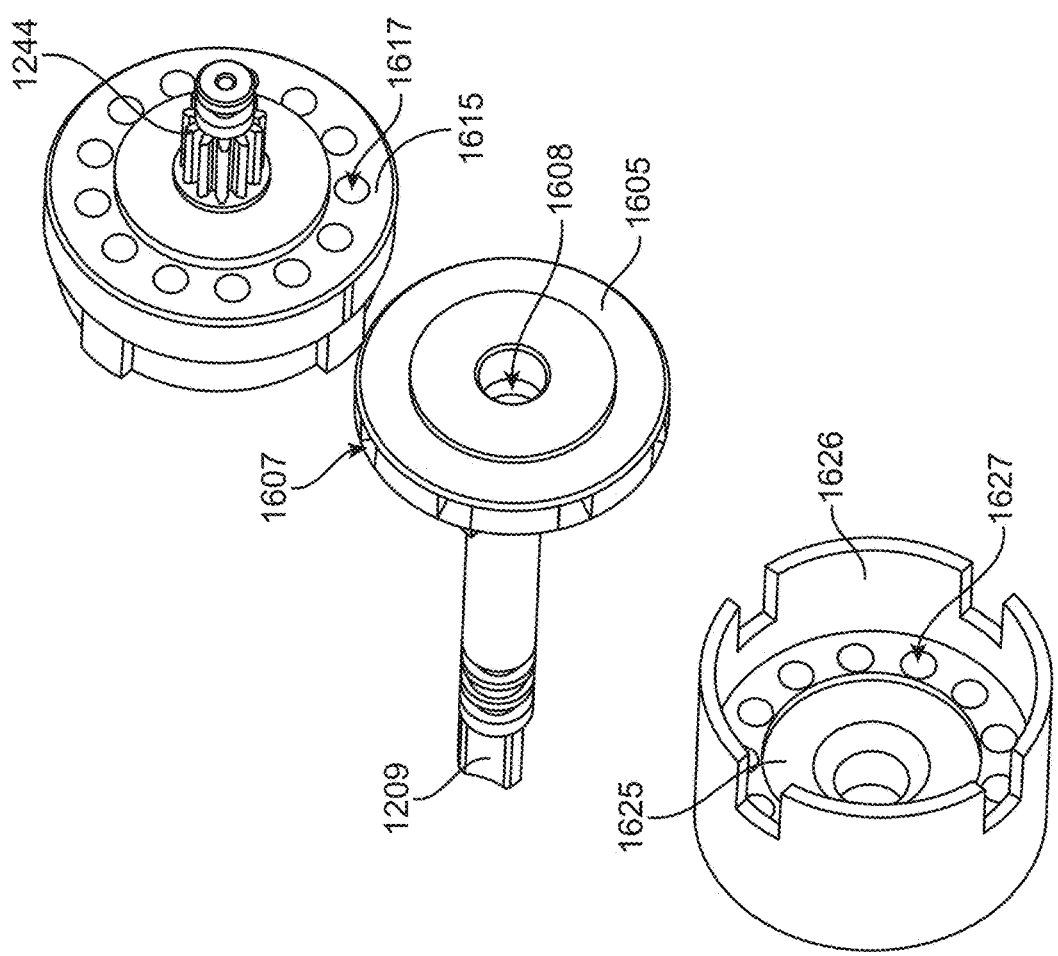

In some implementations, the magnetic field of the magnet discs 1605, 1615 can be made stronger by incorporate a second rotating magnet disc 1625. FIG. 6B and FIGS. 8A-8B illustrate the second rotating magnet disc 1625 positioned distal of the translating magnet disc 1605. These proximal and distal rotating magnet discs 1615, 1625 can create a stronger magnetic field to achieve linear translation of the translating magnet disc 1605 positioned therebetween. The proximal and distal rotating magnet discs 1615, 1625, can be fixed relative to one another so that they spin together. The translating magnet disc 1605 can be positioned within a space between the proximal and distal rotating magnet discs 1615, 1625. The distal rotating magnet disc 1625 can incorporate one or more magnets configured to amplify the magnetic field. For example, a magnet of the proximal magnet disc 1615 can create an attractive magnetic field for the magnet of the translating magnet disc 1605 to urge the translating magnet disc 1605 in a proximal direction towards the proximal magnet disc 1615. A magnet of the distal magnet disc 1625 can create simultaneously a repulsive magnetic field for the magnet of the translating magnet disc 1605 to urge the translating magnet disc 1605 further in the proximal direction toward the proximal magnet disc 1615. Thus, the repulsive and attractive magnetic fields work in concert with one another to achieve linear motion in the proximal direction. To achieve the motion in the opposite (i.e., distal) direction, the magnet of the proximal rotating magnet disc 1615 can repel the magnet of the translating magnet disc 1615 and the magnet of the distal rotating magnet disc 1625 can attract the magnet of the translating magnet disc 1605 creating a simultaneous distal push and distal pull to ensure the translating magnet disc 1605 travels in the distal direction.

The number of magnets on each of the magnet discs and their relative arrangement with each other can vary to achieve the desired oscillation motion of the elongate member 250 of the cutting tube 210. FIG. 8A-8B shows the translating magnet disc 1605 can include bores 1607 sized to contain its magnets. The proximal rotating magnet disc 1615 can include a plurality of bores 1617 sized to receive its magnets and the distal rotating magnet disc 1625 can include bores 1627 sized to receive its magnets. The bores 1607, 1617, 1627 of each of the discs can be located near its perimeter such that they are substantially aligned along the longitudinal axis of the housing. The distal rotating magnet disc 1625 can incorporate walls 1626 creating a barrel housing sized to contain the translating magnet disc 1605 such that the translating magnet disc 1605 can slide back and forth a distance within the walls 1626 of the barrel housing. A proximal-facing surface of the distal rotating magnet disc 1625 can create a hard stop on a distal end for the translating magnet disc 1605. A distal-facing surface of the proximal rotating magnet disc 1615 can create a hard stop on a proximal end for the translating magnet disc 1605. In an implementation having only one rotating magnet disc 1615, a separate distal hard stop feature can be formed within the housing to limit distal motion of the cutter spline 1209.

The oscillation can be achieved by incorporating a rotating disc with a plurality of magnets positioned around a circumference of the disc in alternating fashion such that the single disc has magnets with alternatingly reversed poles. The mating ring can include identical magnets. When the opposite poles of the magnets align, an attractive magnetic force is generated urging the mating ring toward the spinning disc. When the identical poles of the magnets align, a repulsive magnetic force is generated urging the mating ring away from the spinning disc. Each increment around the circumference of the discs aligns the magnets generating either attractive or repulsive magnetic fields between the mating ring and the spinning disc. With each increment of rotation, a different force is generated between the two. The speed of cutting tube oscillation is a function of the speed of rotation of the spinning disc. The discs can incorporate permanent magnets or electromagnets. The electromagnets can be controlled to program a leading edge and trailing edge of the magnetic force. In some implementations, the discs can be angled relative to one another in order to orient the magnetic field on the translating ring to encounter a sharp increase in electromagnetic force relative to its opposite ring for a sharp change during extension and a gradual decrease during retraction to achieve asymmetry in cutting tube motion. The magnets on the discs can have an offset of about 10 degrees relative to one another as opposed to being flush with respect to each other. The rotating ring can encounter a sharper density of magnetic gradient on the leading edge of the advancing stroke, but the trailing edge can taper off more slowly than the leading edge. The gradient per increment of rotation can be much higher in the forward edge.

The oscillation drive mechanism, whether using a cam assembly or magnetic drive to convert rotary motion into axial motion, can incorporate gearing to increase the output from the rotation of the camshaft 405. The aspiration pump 245 generally requires a slower turning speed for driving aspiration compared to the turning speed needed for oscillation of the elongate member 250 of the cutting tube 210. For example, in vitrectomy it can be desirable to achieve up to 5000 cuts per minute and to achieve a vacuum capability of 650 mmHg or 25 cc/minute volume. The instrument can incorporate a small transmission or gear train to effect a desired oscillation speed. The gear train can be positioned between the camshaft 405 and the elongate member 250 of the cutting tube 210 and, in some implementations, can be configured to engage and disengage the elongate member 250 of the cutting tube 210 acting as a clutch mechanism in the oscillation of the elongate member 250. A gear train can effect a fixed ratio between the cutting tube oscillation speed and the aspiration pump rotational speed.

The camshaft 405 of the aspiration pump 245 can rotate at a fixed rate to deliver about 15-30 cc/minute of aspiration potential. However, this rotation may be increased using gearing to ramp up the input from the motor to an output of a desired cutting rate. For example, the double ramp cam described above can include a single stage 5:1 planetary gear drive to increase the rate of rotation from the 140 input RPMs to approximately 700 RPMs. The ratio can be driven by the cam profile and the spacing for the ramp angle driving the cut speed of 2 ms and a dwell of approximately 4 ms. The rotational input of the camshaft 405 can be increased to achieve up to about 5000 CPMs. The gearing can be at any of a variety of ratios depending on the input speed and the output desired. A gearbox may be excluded for higher input speeds. Higher gearbox ratios can also reduce the number of magnets incorporated in the magnetic drive. The gearing can also be used as a transmission element to turn on/off the cutting of the elongate member 250.

Figure 9A:
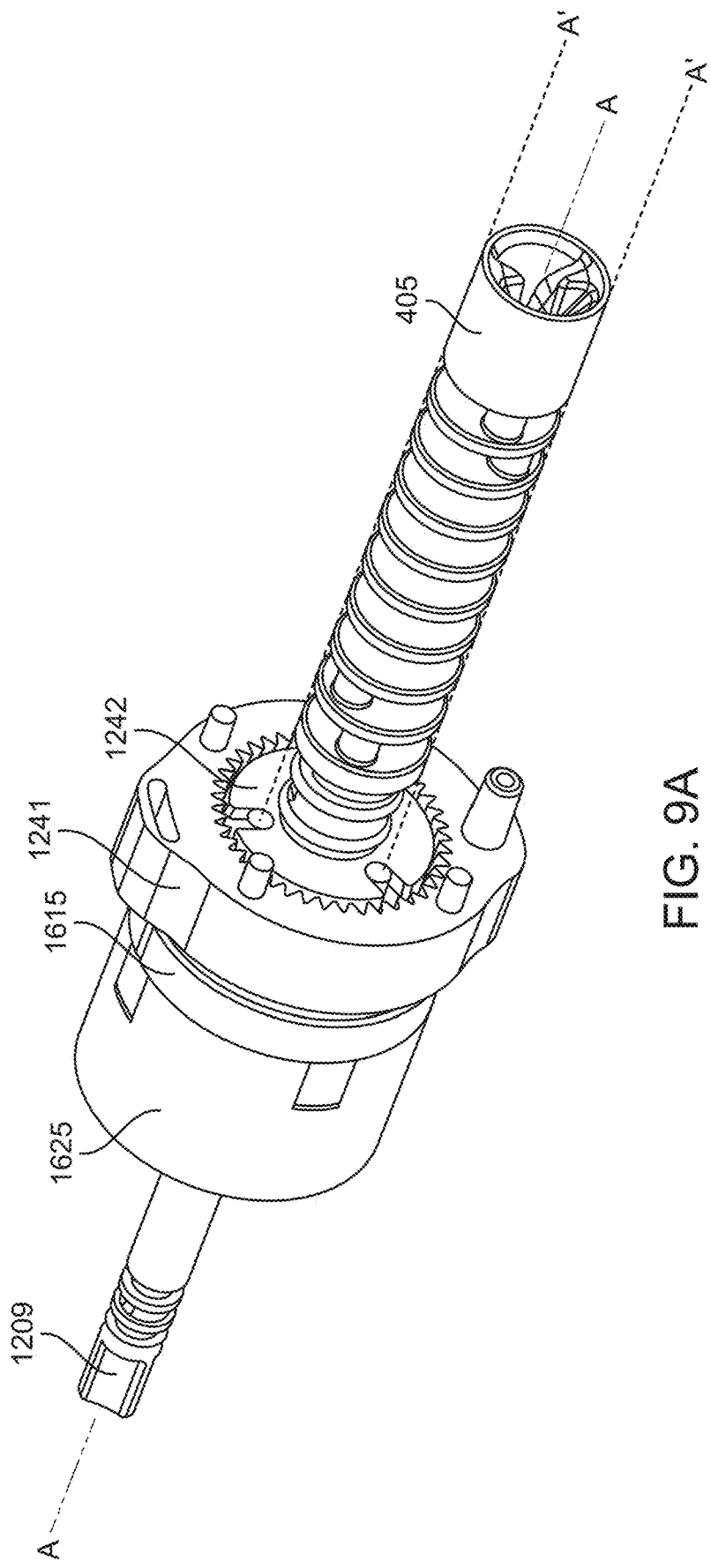
FIG. 9A illustrate a partial perspective view of the magnetic drive of FIGS. 8A-8B assembled with a camshaft of the aspiration pump.
Figure 9B:
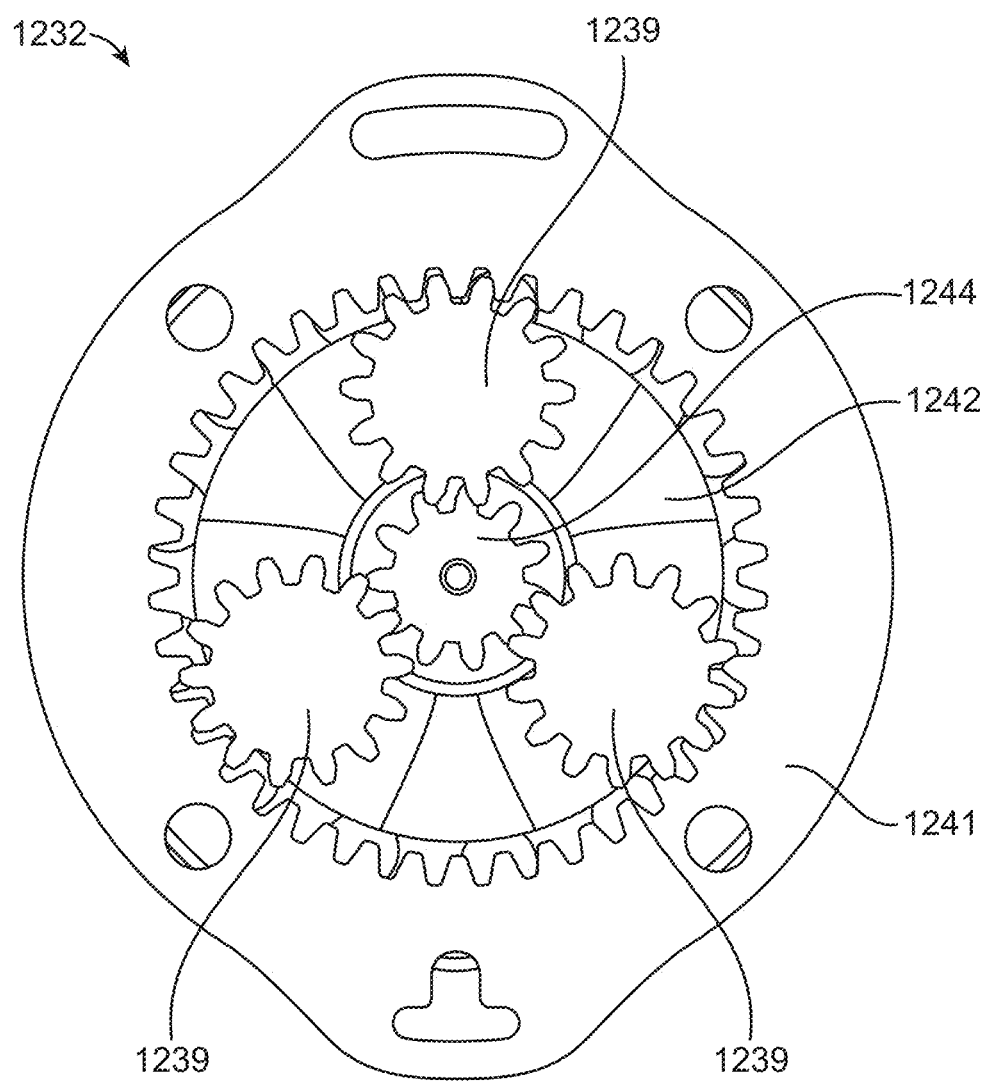
FIG. 9B shows a cross-sectional end view of the gearbox coupled to the camshaft of the aspiration pump of FIG. 9A.

In an implementation, the magnetic drive mechanism can include a planetary gear box 1232 to amplify the input from the drive motor for the pump 245 to achieve a desired output of the elongate member 250 of the cutting tube 210 (i.e., 5000 CPMs). FIGS. 9A-9B illustrates a gear box 1232. The gear box 1232 can include a planet carrier 1242 configured to rotate around a central axis A. The planet carrier 1242 can be fixed to and driven by the camshaft 405, which in turn is driven by the drive shaft of the motor within the driver portion (not shown). The planet carrier 1242 can be coupled to a plurality of planet gears 1239. The planet carrier 1242 and planet gears 1239 are positioned within a ring gear 1241. The planet gears 1239 mesh with internal threads on the ring gear 1241 encircling the planet gears 1239 as well as with a sun gear 1244 positioned internal to the planet gears 1239. The ring gear 1241 causes each planet gear 1239 to rotate around their own central axes A' as they rotate with the planet carrier 1242 around the central axis A of the planet carrier 1242. The rotation of the planet gears 1239 causes the internal sun gear 1244 to rotate around the central axis A.

Rotation of the internal sun gear 1244 drives the oscillation of the elongate member 250 of the cutting tube 210 as discussed in more detail above. The sun gear 1244 in the implementation shown in FIGS. 6A-6B is positioned on a proximal side of the proximal rotating magnet disc 1615, which as discussed above causes reciprocating motion of the translating magnet disc 1605 on the cutter spline 1209 and thus, the cutting tube 210.

The gear ratio between the camshaft 405 rotation and the rotation of the sun gear 1244 can vary. The gear ratio can be about 5:1 or 6:1 although the ratio can vary.

The proximal rotating magnet disc 1615 can include a central stem 1628 sized and positioned to mate with a corresponding central bore 1608 in the translating magnet disc 1605. The coupling between the stem 1628 and the bore 1608 can be sealed by one or more O-rings (see FIG. 6B). The internal sun gear 1244 extending from a proximal end of the rotating magnet disc 1615 can additionally incorporate a stem having one or more O-rings to seal the fluid pathway that extends from the opening of the cutting tube 210 to the aspiration pump 245.

Figure 9C:
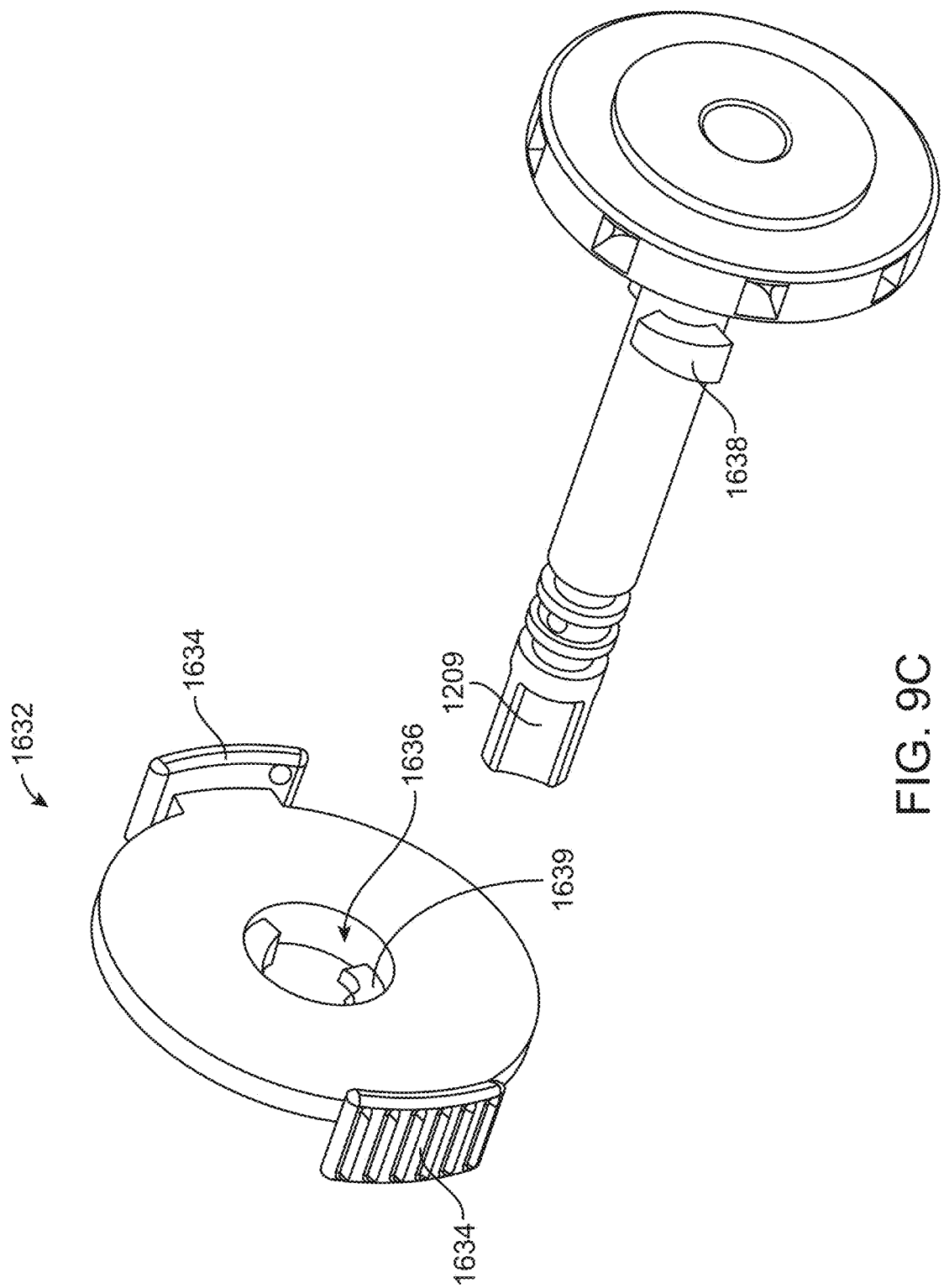
FIG. 9C shows a cutter switch configured to turn on/off oscillation of the cutter tube.

Despite being physically coupled, the pump and the oscillation can be functionally decoupled. The working portion 2005 can incorporate a cutter switch 1632 on a portion of the housing. The cutter switch 1632 can control whether the cutting tube 210 is activated or not when the trigger 228 is pressed. The cutter switch 1632 can lock out the oscillation mechanism so that no oscillation occurs upon activation of the trigger 228. The user can control whether the instrument cuts during aspiration or does not cut during aspiration. As best shown in FIG. 9C, the cutter switch 1632 can be a generally ring-shaped disc having an outer grip feature(s) 1634 and a central aperture 1636. The grip feature 1634 is configured to extend outside the housing of the working portion 2005 such that the user may engage and actuate the cutter switch 1632. In one implementation, the cutter switch 1632 is configured to be rotated around the longitudinal axis of the instrument to select between oscillation of the cutting tube and no oscillation of the cutting tube. It should be appreciated however that the actuation of the switch 1632 can vary. The cutter spline 1209 can extend through the central aperture 1636 of the cutter switch 1632. The cutter spline 1209 can include a ramp feature 1638 at its base that has a shape corresponding to a ramp feature 1639 surrounding the central aperture 1636 of the cutter switch 1632. When the cutter switch 1632 is rotated around the longitudinal axis in a first direction, the ramp feature 1639 of the central aperture 1636 and the ramp feature 1638 at the base of the cutter spline 1209 are disengaged such that the cutter spline 1209 can translate axially relative to the aperture 1636. When the cutter switch 1632 is rotated around the longitudinal axis in a second, opposite direction, the ramp feature 1639 of the central aperture 1636 engages the ramp feature 1638 at the base of the cutter spline 1209. The engagement of the ramp features 1638, 1639 cause axial translation of the cutter spline 1209 in a distal direction relative to the aperture 1636. The engagement of the ramp features with one another fixes the cutter spline 1209 against the cutter switch 1632 and prevents it from translating axially relative to the aperture 1638, effectively cutting off oscillation even while the magnetic drive continues to spin.

As discussed elsewhere herein the motor can be turned on/off with one or more of the user inputs such as a multi-way trigger 228. The effective aspiration delivered through the tube 210 can be a function of trigger actuation (e.g., depression by a finger or thumb). For example, the first 20% of the trigger stroke can turn the motor on. The first 0-10% of the trigger stroke can be a dead time. After the first 10% of trigger stroke up to about 20% the motor can be turned on so that vacuum builds. After 20% of trigger stroke, a valve may be opened to control aspiration achieved. The vacuum can be variable with the trigger position, for example, from 0-100%. The cut mode can be selectable with the cutter switch 1632 or another selector. The cut rate achieved for vitrectomy is preferably about 5000 CPMs, which is constant during use. The constant cut rate can be activated after 20% of trigger stroke.

The aspiration pump can be run in reverse to regurgitate fluid out the cutting tube 210. Tissues can be inadvertently captured or clogs can occur during a procedure. Running the aspiration pump in reverse can cause regurgitation of fluid out the tube 210 and release these tissues and/or help purge a clog. Running the aspiration pump forward to generate a vacuum or reverse to purge fluids out the tip can be linked to the position of the trigger 228. For example, during a procedure the trigger 228 can be depressed to turn on the aspiration pump and allow vacuum to build within the instrument. Upon release, the trigger 228 can return to its neutral position and aspiration is turned off. The user can then manually purge the tube 210 by urging the trigger 228 upward away from neutral position causing the aspiration pump to run in reverse and urge fluid through the tube 210 and out the distal opening. The instrument may be coupled to an irrigation source such that the aspiration pump run in reverse delivers irrigation fluid from the irrigation source out the tube 210.

The instrument can allow for at least two operating modes including (1) aspiration-only and (2) aspiration-plus-cutting. Use of the term "aspiration-only" is in the context of whether or not cutting is additionally being performed. It should be appreciated that "aspiration-only" may be concurrent with the delivery of irrigation fluid. As discussed above, the instrument can also run in an irrigation-delivery only mode. The aspiration delivered through the cutting tube 210 can be controlled by a bypass or bleed valve 1640 (see FIG. 6B). In some implementations, the bleed valve 1640 can be positioned distal to the aspiration pump 245 and proximal to the cutter assembly. The bleed valve 1640 can be used to modulate the effective flow rate of the aspiration pump 245 through the lumen of the cutting tube 210. The motor driving the pump can operate at a fixed speed resulting in the aspiration pump 245 operating at a fixed speed. The bleed valve 1640 allows a user to modulate the effective aspiration upon actuation of the trigger 228. The bleed valve 1640 can siphon off substantially all aspiration generated by the aspiration pump away from the lumen of the elongate member. When the bleed valve 1640 is open, the vacuum pump 245 is connected (i.e., bypassed) to the irrigation fluid so there is minimal to no aspiration delivered through the cutting tube 210. When the valve 1640 is closed, the bypass is closed and the vacuum pump 245 is directly connected to the cutting tube 210. Full aspiration is directed through the lumen of the cutting tube 210 when the bleed valve 1640 is fully closed.

The bleed valve 1640 can be coupled to actuation of the trigger 228 so that movement of the trigger 228 controls the position of the valve 1640. Coaxial irrigation can be routed through the bleed valve 1640 to minimize compliance to mitigate surge in the vacuum. For example, when the instrument is in a resting state (i.e., no actuation of the trigger 228), the bleed valve 1640 can be open to the atmosphere (or irrigation fluid) so that no aspiration is drawn through the cutting tube 210. A first amount of travel of the trigger 228 away from the resting state can activate the motor 230, which in turn drives the aspiration pump 245. The bleed valve 1640 can remain open such that no aspiration is delivered through the cutting tube 210 even if the motor is turning at full speed. Travel of the trigger 228 a further amount can start to close the bleed valve 1640 to increase slowly the aspiration delivered through the cutting tube 210. The greater the trigger 228 is actuated the greater the aspiration delivered through the cutting tube 210 until the bleed valve 1640 achieves the fully closed position. The valve 1640 can allow flow control of aspiration from near zero to 100% (650 mm Hg). In some implementations, the trigger stroke from 0 to 20% can be a dead band for starting the motor 230 and aspiration so that valve movement does not begin until after the trigger 228 reaches at least 20% of initial movement from resting position. The relationship between trigger movement and % of aspiration can be linear or near linear.

The configuration of the bleed valve 1640 can vary. In some implementations, the bleed valve 1640 can be a needle valve or butterfly valve (i.e., in-line linear or rotary). The movement of the trigger can be scaled down to movement of the valve 1640. The mechanical scaling of the trigger movement can incorporate a helical cam, rack and pinion cam, or linkage drive motion. The orientation can be in-line with the longitudinal axis of the device as shown in FIG. 6B or can be perpendicular either vertically or horizontally. In some implementations, the bleed valve 1640 can be a needle valve having an axial-aligned helical cam driven needle that moves relative to a valve seat in a fluidic channel. The thread pitch and angle of the valve seat can be designed to achieve the desired scaling relative to trigger motion. As the trigger travels away from the resting position, the needle is urged further toward the valve seat incrementally closing the valve. The valve 1640 can also be a rotary driven flat valve that offers a shorter length with a smaller angle on the valve seat. The flat valve can be aligned with the trigger axis to be drive directly from, for example, pivot of the trigger. In another implementation, the valve 1640 can be a vertical needle rack and pinion valve. The trigger 228 can move a gear rack along the longitudinal axis of the instrument. The gear rack can engage a pinion gear to urge the fluidic seal up and down relative to the valve seat in the fluidic channel. The scaling of the trigger movement can incorporate a lower friction.

Other Implementations

The drive for the aspiration pump need not be coupled to cutting tube motion. The drive mechanism 205 can be configured to allow a user to drive aspiration via the aspiration pump 245 independently from cutting via the cutting tube 210 in a seamless manner, for example, dependent upon the degree of actuation of the trigger 228. For example, the reusable driver portion 2010 of the instrument may include a clutch or gear train configured to decouple rotations of the aspiration pump 245 from oscillation of the cutting tube.

Figure 10:
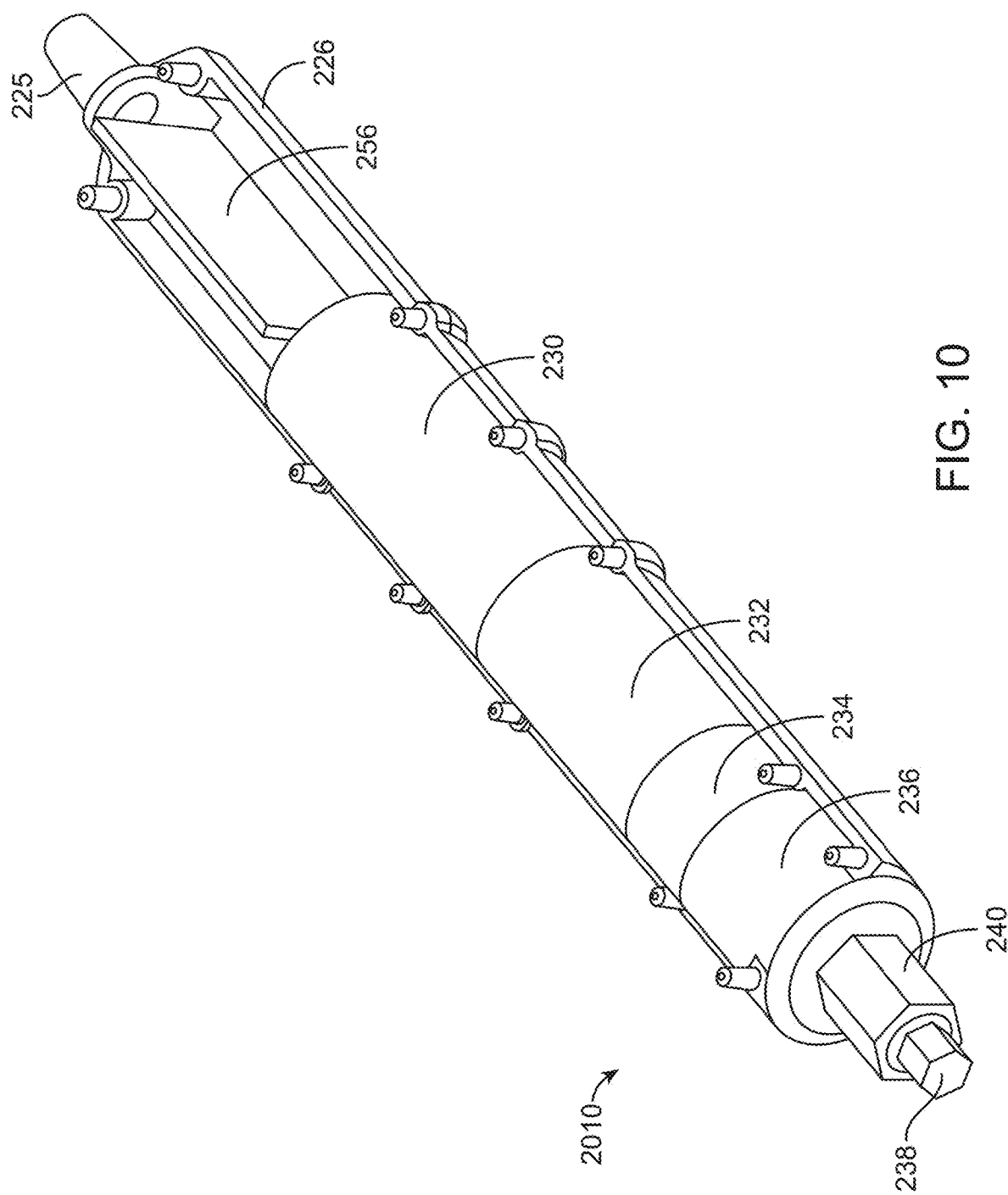
FIG. 10 shows an implementation of a reusable, durable driver portion according to an implementation.

FIG. 10 shows a reusable, driver portion 2010 for use with an instrument 200. A portion of the housing is removed revealing components of a drive mechanism 205. In an implementation, the drive mechanism 205 can include a motor 230 with or without a gear box or gearhead 232, a gear train 234 positioned between the gearhead 232 and a motor adaptor 236, and concentric motor drives including an inner drive shaft 238 extending through an outer drive shaft 240. Each of the inner and outer drive shafts 238, 240 can extend through the motor adaptor 236 and attach to gearhead drive shaft 243 of the gearhead 232. There can be clearance between the motor adaptor 236 and the shafts 238, 240 such that the shafts freely rotate with motor 230. The drive of the cutting tube 210 and the aspiration pump 245 can be decoupled due to the presence of the concentric drive shafts 238, 240 each driving either the cutting tube 210 or the aspiration pump 245.

FIG. 10 shows the gear train 234 is positioned between the gearhead 232 and the motor adaptor 236. In an implementation, the gear train 234 is a differential. Standard differentials allow a motor to drive two shafts at different RPMs. A standard differential has a ring gear connected to at least one spider gear. The spider gear can move along two axes of rotation—one along the axis of the ring gear and another around its own axis of rotation. Two side gears and the spider gear are meshed together. Power from a motor flows to the ring gear, the spider gear, and the two side gears to cause two shafts to rotate. The ring gear, spider gear, and side gears may all rotate as a single, solid unit such that both shafts rotate at the same RPM. The spider gear may also rotate around its own axis resulting in a combined rotation—rotation around the ring gear axis as well as spin around the spider gear's own axis. The side gears meshed with the spider gear(s) will result in the shafts moving at different RPM. Standard differentials rely on turning the power flow direction by 90 degrees to each of the shafts. In the present system, the differential gear train 234 does not turn the power flow away from an axis A of the motor drive shaft, but rather maintains the power flow of the motor 230 along the axis A of the motor drive shaft.

Figure 11A:
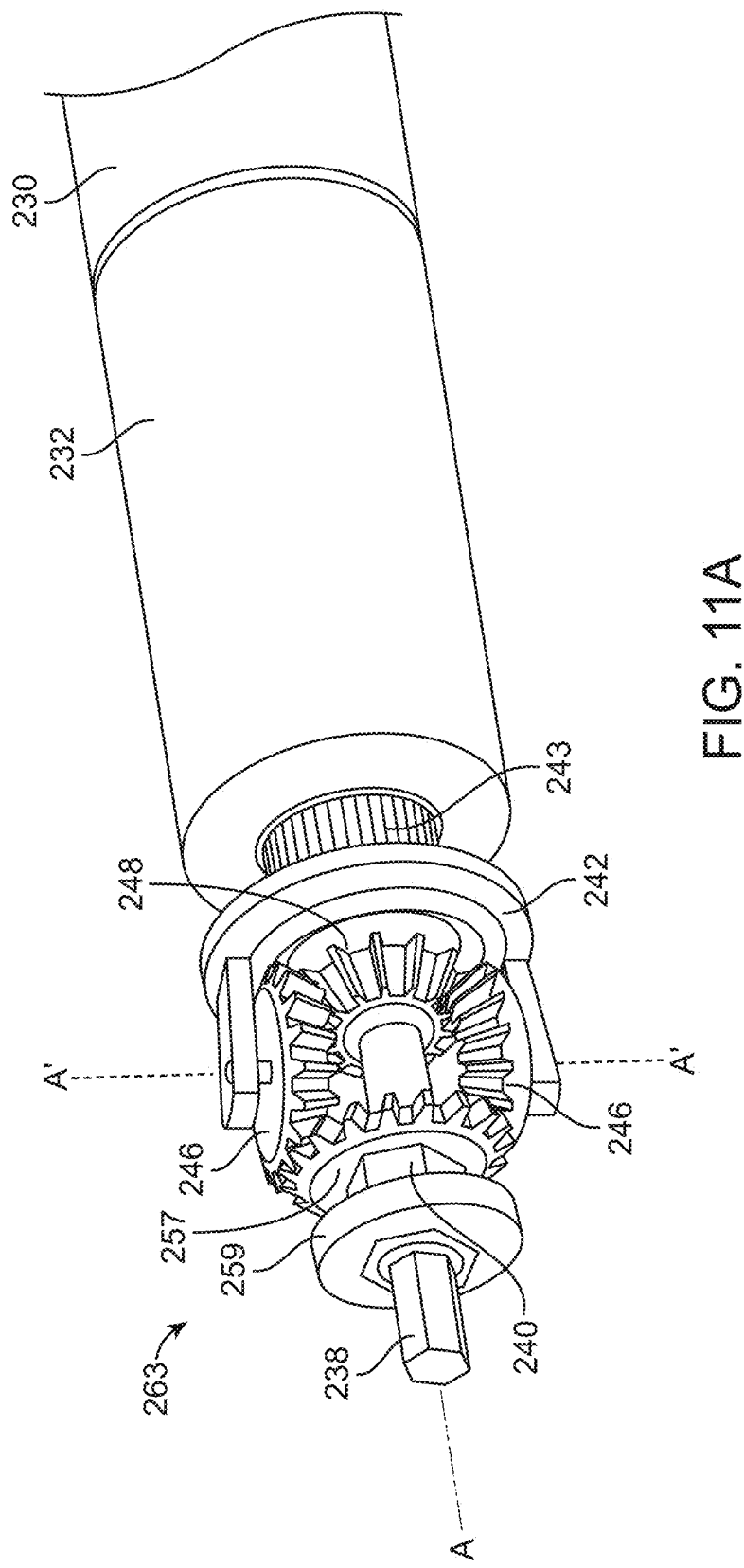
FIG. 11A shows an implementation of a drive system for the portion of FIG. 10 according to an implementation.

FIG. 11A shows an implementation of a differential gear train 234 of the drive mechanism 205 of the instrument 200. A gear carrier 242 is fixed to and driven by gearhead drive shaft 243 such that the gearhead 232 drives the gearhead drive shaft 243, which in turn drives the gear carrier 242 to rotate around a longitudinal axis A of the entire assembly. The gear carrier 242 turns with the gearhead 232 and gearhead drive shaft 243. The gear carrier 242 may be coupled to two opposing pinions 246 configured to rotate about two axes. The pinions 246 may rotate around the longitudinal axis A of the entire assembly as the gear carrier 242 turns. The pinions 246 may also spin around their own axes A'. The two pinions 246 mesh on a proximal end with a first side gear 248 configured concentrically with the gear carrier 242. The two pinions 246 mesh on a distal end with a second side gear 257. The inner drive shaft 238 can be fixedly joined to the first side gear 248 such that no relative movement between them occurs. The inner drive shaft 238 turns with the first side gear 248. The inner drive shaft 238 extends concentrically through the outer drive shaft 240. The outer drive shaft 240 can be fixedly joined to the second side gear 257 such that the second side gear 257 turns the outer concentric drive shaft 240. Power from the motor 230 drives the gearhead 232, which in turn drives the gearhead drive shaft 243, which in turn drives the gear carrier 242, which powers the differential gear train 234. The power from the gear carrier 242 drives the pinions 246, which drive either one or both of the side gears 248, 257. The differential gear train 234 of the drive mechanism 205 does not direct the power from the gearhead drive shaft 243, for example at right angles relative to the axis A, as happens in a standard automotive differential. Rather, the inner drive shaft 238 extends concentrically through the outer drive shaft 240 and is fixed to and driven by side gear 248. The differential drive gear can be incorporated within the driver portion of the instrument or within the disposable portion of the instrument.

The drive mechanism 205 can additionally include a second motor 259 that controls the speed of the outer concentric drive shaft 240. The second motor 259 can be a small, very low power motor. The second motor 259 can include a rotary encoder. The first motor 230 and gearhead drive shaft 243 can provide all the power for the drive system of the device and the second motor 259 can differentially split that power between the concentric drive shafts 238, 240. The configuration of the second motor 259 can vary. In some implementations, the second motor 259 is a pancake motor. A pancake motor is an example of a low RPM, high torque motor that can directly drive rotation of the drive shaft. In an implementation, the second motor 259 can be a pancake motor having a central bore having an inner diameter configured to receive the concentric drive shafts 238, 240 therethrough. The second motor 259 can include a first ring portion positioned concentrically within an inner diameter of an outer second ring portion of the motor 259. The inner, first portion of the motor 259 can rotate relative to the outer, second portion of the motor 259. The inner, first portion of the motor 259 can rotate and the outer, second portion of the motor 259 can be static, for example, attached to a region of the housing or a motor bracket. The second motor 259 can have an aspect ratio that is much flatter than a conventional motor that is typically cylinder shaped. The flat aspect ratio allows for positioning the second motor 259 within a tight space. It is preferable that the second motor 259 be relatively high torque in order to split the power between two drive shafts 238, 240. The second motor 259 is also preferably low RPM such that it can control directly rotation of a shaft without need for gear reduction. The inner, first portion of the second motor 259 can drive the outer drive shaft directly.

The first motor 230 powers both inner and outer shafts 238, 240 via the drivetrain between the two. The second motor 259 allows a user to select the RPMs of the outer shaft 240 and inner shaft 238. In order to run both shafts at the same speed, the second motor 259 rotates at the same RPM and rotational direction as the gearhead drive shaft 243.

The control processor 280 including software can be on a PCB 255 within the housing 226. The software is programmed or capable of being programmed to control the RPM of the output from the gearhead drive shaft 243 and the RPM of the outer concentric shaft 240 via the second motor 259 and encoder. The software therefore indirectly controls the output of the inner concentric drive shaft 238 by specifying the RPMs of the gearhead drive shaft 243 and the outer concentric shaft 240. In doing so, RPMs of the outer and inner concentric drive shafts 238, 240 can be independently specified.

Figure 11B:
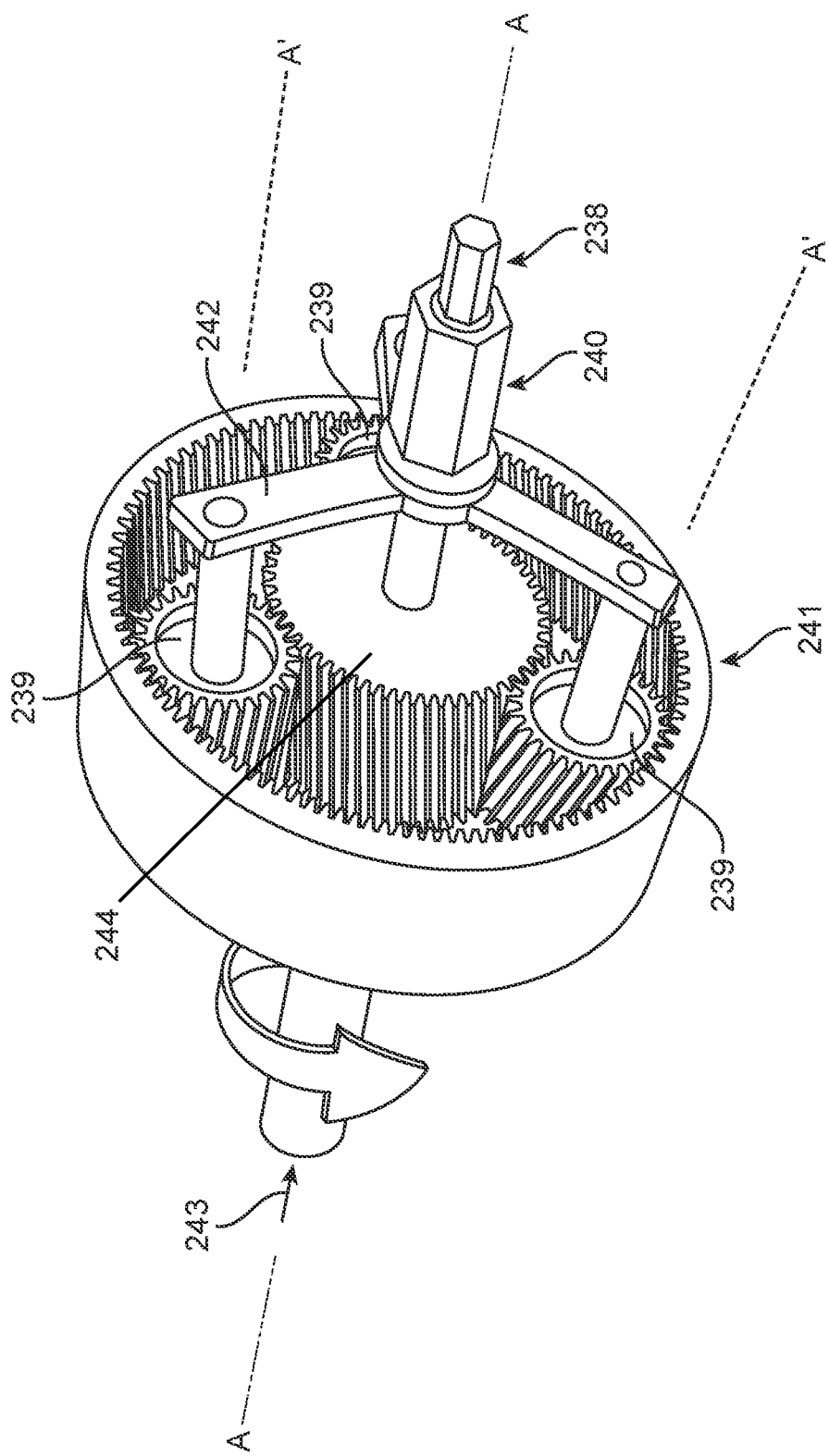
FIG. 11B shows an implementation of a drive system for the portion of FIG. 10 according to another implementation.

It should be appreciated that the configuration of the gear train 234 of the drive mechanism 205 may vary. In some implementations, the gear train 234 of the drive mechanism 205 configured to drive two shafts independently is a planetary gear train. FIG. 11B shows an implementation of a planetary gear train 234. As with the implementation described above with respect to FIG. 11A, the drive mechanism 205 can drive the pump independently from the cutting tube via concentric, coaxial drive shafts 238, 240. The gear train 234 of the drive mechanism shown in FIG. 11B can allow for at least two operating modes including (1) aspiration only and (2) aspiration-plus-cutting. A gear carrier 242 is fixed to and driven by gearhead drive shaft 243 such that the gearhead 232 drives the gearhead drive shaft 243, which in turn drives the gear carrier 242 to rotate around the longitudinal axis A of the entire assembly. The gear carrier 242 turns with the gearhead drive shaft 243. The gear carrier 242 may be coupled to a plurality of planet gears 239. The planet gears 239 may rotate around the longitudinal axis A of the entire assembly as the gear carrier 242 turns. The planet gears 239 may also spin around their own axes A'. The planet gears 239 mesh with a ring gear 241 encircling the planet gears 239 as well as with a sun gear 244 positioned within the planet gears 239 such that the planet gears 239 travel around the sun gear 244. The inner drive shaft 238 can be fixedly joined to the sun gear 244 such that no relative movement between the sun gear 244 and the inner drive shaft 238 occurs. The inner drive shaft 238 turns with the sun gear 244. The inner drive shaft 238 extends concentrically through the outer drive shaft 240. The outer drive shaft 240 can be fixedly joined to the gear carrier 242, which is fixedly joined to the gearhead drive shaft 243. Power from the motor 230 drives the gearhead 232, which in turn drives the gearhead drive shaft 243, which in turn drives the gear carrier 242, which powers the gear train 234. The gearhead drive shaft 243 directly drives the outer drive shaft 240.

In a first mode, the gear train 234 shown in FIG. 11B can allow the pump to run, but not activate cutting oscillating motion of the cutting tube. Thus, the first mode can be Inspiration/Aspiration "I/A" mode. Only the sun gear 244 and thus, the inner drive shaft 238 for the cutting tube is kept stationary while the other portions of the gear train 234 rotate. Friction in the disposable cutter system maintains the sun gear 244 stationary. In a second mode, the gear train 234 shown in FIG. 11B can allow for activation of cutting in addition to inspiration/aspiration via the pump. The sun gear 244 rotates while the ring gear 241 stays stationary. Unlike a differential gear train described above with respect to FIG. 11B, a planetary gear train need not include a second motor to drive the outer drive shaft 240 thereby providing a more compact, lower cost system. For example, the ring gear 241 can be prevented from rotating via an input by the user, such as a finger throttle on the instrument. Depressing the finger throttle can cause a component to contact a region of the ring gear 241 manually thereby acting as a break to stop its rotation. Preventing rotation of the ring gear 241 forces input power from the gearhead drive shaft 243 to transfer from the ring gear 241 to the sun gear 244. When this occurs, the cutting tube is powered to start oscillating due to rotation of the inner drive shaft 238 in addition to the already-rotating outer drive shaft 240. The more the ring gear 241 is slowed, the more the power is directed to the sun gear 244 and the inner drive shaft 238.

As mentioned above, the gear train 234 allows for driving the cutting and aspiration independently. FIGS. 10 and 11A-11B show the inner concentric drive shaft 238 extending through the outer concentric drive shaft 240, which in turn extends through the second motor 259. The inner drive shaft 238 may extend further distal to the outer drive shaft 240 and both the inner and outer drive shafts 238, 240 extend outside the distal end of housing 226 of the driver portion 2010. The combination of the inner and outer drive shafts 238, 240 extending outside the housing 226 of the driver portion 2010 form a concentric motor coupler 263 configured to engage with corresponding features within the working portion 2005. The coupler 263 drives the aspiration pump 245 and the cutting tube 210 of the working portion 2005. In some implementations, the inner drive shaft 238 powers cutting via oscillation of the cutting tube 210 and the outer drive shaft 240 powers aspiration through the cutting tube 210 via activation of the aspiration pump 245.

The inner drive shaft 238 may be coupled to the cutter cam 212 configured to convert rotary motion of the drive shaft 238 into linear motion of the cutting tube 210. The outer drive shaft 240 may be coupled to the piston cam 249 configured to convert rotary motion of the outer drive shaft 240 into linear motion of pistons 247 of the aspiration pump 245 to power aspiration through the cutting tube. The coupler 263 of the driver portion 2010 can insert into the proximal end of the working portion 2005 such that the shafts 238, 240 mate with their respective cams.

As mentioned above, the aspiration pump 245 of the instrument 200 can be a piston pump and can incorporate any of a variety of mechanisms configured to generate a negative pressure within the lumen of the elongate member (see FIG. 12). In some implementations, the aspiration pump 245 is a piston pump having a plurality of pistons 247 driven by a piston cam 249, which in turn is driven by the drive mechanism 205. The aspiration pump 245 is configured to provide smooth continuous and/or discontinuous pulsatile aspiration, for example, as described in U.S. Publication No. 2018/0318133, published Nov. 8, 2018, which is incorporated herein by reference. The pulsatile vacuum allows for application of full vacuum through the cutting tube 210 without risk for collapse of the anterior chamber. While at the peak of the pulse, the instrument 200 can generate a high vacuum. However, since it is pulsed, the average aspiration flow rate can be low enough for the irrigation inflow to maintain proper anterior chamber support even under these high vacuums at the pulse peak. Movement of the pistons 247 in a first direction within the pumping chambers creates a vacuum such that material from the eye is drawn into the lumen of the cutting tube 210. Movement of the pistons 247 in a second, opposite direction within the pumping chambers expels material from the pumping chamber and out of the instrument 200.

The pistons 247 can be moved in their respective pumping chambers by the piston cam 249 (see FIG. 12). FIG. 12 shows the cam surface 219 is configured to provide reciprocal linear motion of the pistons 247. The piston cam 249 is positioned proximal to the pistons 247 such that the cam surface 219 urges the pistons 247 distally towards the distal end of their respective pumping chambers upon rotation of the piston cam 249. The geometry of the cam surface 219 can be designed to provide different motion profiles of the pistons 247 in their respective piston chambers and thereby create different vacuum profiles (i.e. smooth continuous, continuous with spikes in negative pressure, or discontinuous pulsed negative pressure). The cam surface 219 can be elliptical, eccentric, egg, or snail-shaped. During a first fraction of rotation of the cam 249, the proximal piston heads 253b slide along the ramped portion of the cam surface 219 and the piston 247 is moved distally along the longitudinal axis A of the instrument 200. During a second fraction of rotation of the cam 249, the proximal piston heads 253b slide past the cam surface 219 that terminates at ledge. When the piston heads 253b drop off ledge the distally directed force against the pistons 247 by the cam 249 is released. The pistons 247 may also travel proximally due to a second ramp of the cam surface 219 allowing for slower retraction of the pistons 247 within their pumping chambers.

Springs 251 surrounding a central portion of the pistons 247 are biased to urge the proximal piston head 253b in a proximal direction towards the proximal end region of the piston chamber. The springs 251 are compressed as the piston 247 is urged by the cam surface 219 in a distal direction. Upon further rotation of the piston cam 249, the distally directed force against the proximal piston heads 253 is removed (i.e. due to the ledge or due to a second ramp) and the springs 251 urge the pistons 247 backwards creating a vacuum within the respective pumping chambers. A complete revolution of the piston cam 249 therefore allows for axial movement of each piston 247 in succession. For pulsatile vacuum, the piston heads 253b slide along the cam surface 219 and extend in the distal direction at a first rate and the piston heads 253b drop off the cam surface 219 and retract in the proximal direction at a second rate that is much faster than the first rate. For more continuous flow, the piston heads 253b slide along the ramps of the cam surface 219 more smoothly and in an overlapping manner.

FIG. 12 shows the camming mechanism for the cutting tube 210 as well as the camming mechanism for the aspiration pump 245. The camming mechanism for the cutting tube 210 can include the cutter cam 212 positioned distal to a cam follower 213. The camming mechanism for the aspiration pump 245 can include the piston cam 249. The piston cam 249 can include a generally cylindrical body defining a bore 261. The bore 261 may extend from a proximal receptacle 218 in the piston cam 249 towards the cam surface 219 on the distal end of the piston cam 249. The cam surface 219 on the distal end of the piston cam 249 can engage with proximal piston heads 253 of the pistons 247. The proximal receptacle 218 is positioned within a proximal end region of the working portion 2005.

The shafts 238, 240 may couple within the working portion 2005 via their outer surface geometry. As best shown in FIG. 10, each of the shafts 238, 240 may terminate in a hex head. The working portion 2005 may incorporate features having complementary geometry configured to mate with the hex heads of the shafts 238, 240. FIG. 12 shows the cutter cam 212 and the cam follower 213 may be positioned within the bore 261 of the piston cam 249. A thin-wall tube 221 can be positioned within the bore 261 between the piston cam 249 and the cutter cam 212. The tube 221 can include a proximal receptacle 222 arranged coaxially within the bore 261 such that the receptacle 222 of the tube 221 is positioned just distal to the receptacle 218 of the piston cam 249. The proximal receptacle 218 of the piston cam 249 may have a geometry complementary to the geometry of the outer drive shaft 240 of the motor coupler 263. For example, the outer drive shaft 240 may include a hex head and the proximal receptacle 218 of the piston cam 249 can engage with the geometry of the hex head such that the piston cam 249 turns with the outer drive shaft 240. Similarly, the proximal receptacle 222 of the tube 221 has a geometry complementary to the geometry of the inner drive shaft 238 of the motor coupler 263. The inner drive shaft 238 may include a hex head and engage with the proximal receptacle 222 of the tube 221 such that the tube 221 turns with the inner drive shaft 238.

The cutter cam 212 and cam follower 213 are configured to spin independent of the piston cam 249. The tube 221 can connect to the cutter cam 212, but not the piston cam 249 such that the piston cam 249 and the cutter cam 212 are configured to rotate independently of one another via their respective couplings with the drive shafts.

Still with respect to FIG. 12, the cutter cam 212 can include teeth 211 on its proximal-facing surface configured to engage corresponding teeth on the distal-facing surface of proximal cam follower 213. As cutter cam 212 rotates, the teeth 211 slide along teeth of the proximal cam follower 213. The cam follower 213, cutter spline 209, and cutting tube 210 are pushed backward or in a proximal direction P until the teeth 211 of the distal cutter cam 212 reach a step (not visible in FIG. 12) on the cam follower 213. At this point, the force of a spring 216 urges the cutting tube 210, the cutter spline 209, and the cam follower 213 forward or in a distal direction D. A cutter cushion 217 can be incorporated to provide dampening as the cutter spline 209 springs back toward the distal position. The cutter cushion 217 may reduce the noise that the instrument 200 makes during operation by dampening the cutter spline 209 as it is sprung forward. The cutting tube 210 oscillates back and forth as the cutter cam 212 and cam follower 213 spin.

The cutting tube 210 may be connected to the cam follower 213. The cam follower 213 can have camming surfaces on its distal end that engages with the cutter cam 212. The proximal end of the cam follower 213 can be connected to the spring 216 that pushes the cam follower 213 distally. As the cutter cam 212 rotates, the camming surfaces cause the cam follower 213 to move proximally, compressing the spring 216 further. The cam follower 213 may drop forward (i.e. distally) off the step at a certain point in the rotation. At this point, the spring 216 pushes the cam follower 213 quickly forward until the camming surfaces engage again. Through such a mechanism, the cutting tube 210 can retract with a retraction speed profile that is at least in part a function of the rotational speed of the cutter cam 212. The rotational speed of the cutter cam 212 can be controlled so that the maximum tip retraction speed remains below the critical 'cavitation threshold speed' that would otherwise result in cavitation in the eye. The cutting tube 210 can then extend with an extension speed profile that is at least in part a function of the force of the spring 216 and mass of the cutting tube assembly. In this way, the average retraction speed can be slow, i.e. below the cavitation threshold speed, but the average extension speed can be fast, i.e. close to or higher than the average retraction speed of a typical phacoemulsification tip. Thus, the benefits of mechanical jackhammering can be achieved while the deleterious effects of cavitation are entirely avoided.

When in use, the drive mechanism 205 is capable of retracting the cutting tube 210 in a proximal direction with a retraction speed profile and advancing the cutting tube 210 in a distal direction with an extension speed profile. The retraction speed profile can be different from the extension speed profile. Additionally, the movement profile of the cutting tube 210 can be coordinated with a vacuum profile. For example, while a pulse of vacuum is being applied through the cutting tube 210, the cutting tube 210 can be simultaneously fired in the distal direction D. Where the cutting tube 210 is described as moving in forward and distal directions relative to the treatment site, vibrations of the cutting tube 210 are considered as well. The cutting tube 210 can be vibrated in a similar fashion to conventional phacoemulsification machines. Thus, the cutting tube 210 can be vibrated while a pulse of vacuum is applied and at some phase in the vacuum pulse or thereafter, the vibration and the vacuum can be turned off such that the system comes to rest before initiating a vibration-vacuum sequence again. The coordination between the movement and/or vibration of the cutting tube 210 and the vacuum applied through the cutting tube 210 is described in U.S. Publication No. 2018/0318133, published Nov. 8, 2018, which is incorporated herein by reference.

As discussed above, the device can include a multi-way trigger 228 such as a finger-actuated throttle or trigger. The input provided by the user via the finger throttle can inform software what speed each drive shaft needs to be based on a throttle position map program. For example, the trigger 228 of the instrument 200 can be actuated to move a first amount. One or more sensors can assess the travel of the input 228 is greater than 0%, but less than a certain amount of total travel the input is capable of traveling, for example between about 0% to about 5%. A signal can be sent to the computing unit 115 of the system 100 causing the computing unit 115 to communicate with the fluid system 110 to open a valve 150 of the irrigation system. When the valve 150 opens, irrigation fluid from the irrigation source 130 can flow through irrigation line 155 towards the microsurgical instrument 200. This places the system 100 in an initial irrigation-only phase in which the line 155 is primed with irrigation fluid and the microsurgical instrument 200 is able to deliver irrigation fluid to the treatment site. The input 228 of the instrument 200 can be actuated to move a second amount. The one or more sensors can assess the travel of the input is greater than 5%, but less than a second amount of total travel, for example between about 6% up to about 20%. A low-level aspiration via pump 245 can begin drawing fluid from the microsurgical instrument 200 through the waste line 165. The valve 150 of the irrigation system can remain open such that irrigation fluid from the irrigation source 130 continues to be delivered toward the eye, preferably such that the fluid volume entering the eye is substantially equal to the fluid volume exiting the eye. This places the microsurgical instrument 200 in an irrigation-plus-aspiration phase. The background I/A-only flow can have a low flow rate such as about 2 cc/minute up to about 20 cc/minute at the 20% finger trigger position. The input 228 of the instrument 200 can be actuated to move a third amount. The one or more sensors can assess the travel of the input is greater than 20% up to about 100%. The vacuum within the hand-piece of the microsurgical instrument 200 via the aspiration pump 245 can ramp up. The valve 150 can remain open such that irrigation supply continues. The mechanical oscillation of the cutting phase can initiate once trigger position reaches a threshold (i.e. 20% travel) and further increase to higher frequencies as the trigger is further depressed. Once a procedure completes, the user can then adjust the trigger 228 of the microsurgical instrument 200 back down to 0% at which point the vacuum via the aspiration pump 245 ceases. The valve 150 can close a period after deactivating the pumps (e.g. about 2 s) thereby suspending irrigation toward the microsurgical instrument 200.

As described elsewhere herein, the inputs can activate one or more components of the system such that the pumping and cutting features can gradually ramp up with further actuation of the input, such as like a gas pedal. Generally, the greater the input is actuated, the greater the aspiration vacuum applied. The irrigation delivery can be passive and deliver fluid on demand. As fluid exits the eye, it can be replaced by a substantially equivalent volume at a substantially equivalent rate. The irrigation source can be held above the eye such that hydrostatic pressure maintains the positive pressure to the anterior chamber. The fluid path is substantially sealed such that when fluid is aspirated, the irrigation fluid immediately replaces it.

TABLE 1

| Throttle Position | User Experience | Motor/Gearhead RPM | Inner drive shaft RPM | Outer drive shaft RPM | |
|---|---|---|---|---|---|
| 0 | Nothing | 0 | 0 | 0 | Valve 150 fully closed |
| 1 | Irrigation | 0 | 0 | 0 | Valve 150 fully open |
| 2 | Irrigation + Aspiration | 0 - full | 0 | 0 - full | Motors 230, 259 turning at same speed as gearhead output shaft. Speeds increase as throttle depressed. |
| Transition from 2-3 | Irrigation + Aspiration | ~10% | 0 | 10% | Aspiration drops to low "background flow" level (e.g. ~4 cc/min) |
| 3 | Irrigation + Aspiration + Cutting | 10% - full | 0 - full | 10% - full | Background aspiration continues and slowest cutter speed begins. As finger throttle is further depressed, cutter speed and aspiration rate increase in concert. |

Table 1 illustrates an example of the multi-stage trigger and throttling to achieve different functions of the instrument 200 having two drive shafts. In throttle position 0, the trigger travels 0%, the motor 230 (and the second motor 259, if present) are not spinning and the aspiration, irrigation, and cutting functions are all off. The RPM of the motor 230, the inner drive shaft 238 and the outer drive shaft 240 are all zero and the BSS pinch valve 150 is fully closed. In throttle position 1, the trigger travels greater than 0% to an upper threshold value such as 5%, for example. The motors 230, 259 are still not spinning, but the pinch valve 150 opens to initiate irrigation flow. This position provides irrigation-only function to the instrument 200. The pinch valve 150 remains open in each throttle position other than 0. In throttle position 2, the trigger travels greater than the upper threshold value for position 1, for example, greater than 5% up to an upper threshold value for position 2, for example, 20% travel. Both the motor 230 and the second motor 259 begin turning. Motor 230 and second motor 259 turn at the same speed as the gearhead drive shaft 243. The result is the inner drive shaft 238 (the shaft coupled to the cutter cam 212) does not move. The instrument 200 provides irrigation (due to the valve 150 remaining open) and aspiration (due to motion of piston cam 249) is in an I/A mode. The speeds increase with further depression of the finger throttle thereby ramping up aspiration rate. In preparation for entering throttle position 3, motor 230 RPM drops to a low level (e.g. about 10%) such that aspiration drops to low background flow levels (e.g. 2-4 cc/min). The RPM of outer shaft 240 matches the RPM of gearhead drive shaft 243 such that inner drive shaft 238 RPMs remain at zero. This low background flow may help to attract tissues towards the distal end of the cutting tube 210 to improve cutting by drawing lens fragments into contact with the cutting tube 210 before cutting ensues. This transition is not noticeable by the user. In throttle position 3, the trigger travel reaches and exceeds the upper threshold value for position 2 (e.g. 20%) and the motor 230 begins increasing RPM. The motor 230 increases in RPM throughout throttle position 3. Second motor 259 slows relative to that of gearhead drive shaft 243. This initiates turning of inner drive shaft 238. The inner drive shaft 238 turns cutter cam 212, which translates rotary motion into linear motion of cutting tube 210. Cutting then ensues. As finger throttle is further depressed (e.g. throttle travels greater than the upper threshold of position 2 towards 100%), the cutter speed and the rate of aspiration increase in concert.

In alternative implementations, the inner drive shaft 238 is coupled to the piston cam 249 and the outer drive shaft 240 is coupled to the cutter cam 212. In position 2 of the finger throttle, the motor 230 may start turning while the second motor 259 stays stationary. In position 3 of the finger throttle, the motor 230 continues to turn and the second motor 259 starts turning slowly thereby increasing the inner drive shaft 238 rotation and initiating cutting motion of the cutting tube 210. As the finger throttle is further depressed beyond position 3, the speed of the cutting motion increases.

The gear train 234 can be configured such that it need not incorporate two motors 230, 259 to achieve independent actuation of the two drive shafts 238, 240. For example, the gear train 234 can be a planetary gear train 234 as described with respect to FIG. 11B. The inner drive shaft 238 (the shaft coupled to the cutter cam 212) does not move until reaching throttle position 3. Throttle position 3 may cause the motor 230 to increase in RPM and break (i.e., retard) the rotational speed of the ring gear 241. Any slowing of the ring gear 241 causes rotation of the sun gear 244 and thus, initiates rotation of the inner drive shaft 238. The inner drive shaft 238 can turn the cutter cam 212, which translates rotary motion into linear motion of the cutting tube 210.

One or more aspects of the microsurgical instrument 200 can be programmed by a user. A user may program, for example, one or more aspects of the drive mechanism 205 such as speed of aspiration pump 245, speed of oscillation of the cutting tube 210, limits of maximum speeds, disable/enable various modes (i.e. pulsed mode or burst mode vacuum), adjust parameters of modes (i.e. on time vs. off time during pulse mode), and various other controllable parameters of the instrument 200 as described elsewhere herein. A user can also program the microsurgical instrument 200 using an external computing device 300 in communication with the instrument 200 directly rather than through the instrument 200 or through the system 100. The instrument 200 and/or the system 100 can also be programmed to provide limits on a particular action upon actuation of the input 228. For example, the drive mechanism 205 of the instrument 200 can be programmed to have a minimum and/or maximum speed upon actuation of the input 228 or, in the case of fluid infusion and aspiration, the instrument 200 can be programmed to have a minimum and/or maximum fluid pressure upon actuation of an input 228. Thus, the instruments 200 described herein can be programmed using inputs adjustable by a user as well as by pre-programmed instructions that affect the one or more aspects of the instrument 200 upon actuation of the input 228.

The control processor can be programmed by an input on the device itself or programmed remotely such as by an external computing device 300 having an input. The control processor can operate according to program instructions stored in a memory. Any of a variety of adjustable functions of the instrument may be programmed this way including, but not limited to travel distance of the cutting tube 210, frequency of oscillation of the cutting tube 210, extension speed profile, retraction speed profile, or any other aspect of the motion profile of the cutting tube 210. One of more aspects of the aspiration pumps (e.g. pump 145 of the system 100 as well as aspiration pump 245 of the instrument 200) can also be programmed by a user to control the vacuum applied at the distal end region of the cutting tube 210 including, but not limited to flow rate of aspiration, minimum vacuum pressure, maximum vacuum pressure, frequency of vacuum pulses, or any other aspect of the vacuum profile.

Aspects of the subject matter described herein may be realized in digital electronic circuitry, integrated circuitry, specially designed ASICs (application specific integrated circuits), computer hardware, firmware, software, and/or combinations thereof. These various implementations may include an implementation in one or more computer programs that are executable and/or interpretable on a programmable system including at least one programmable processor, which may be special or general purpose, coupled to receive signals, data and instructions from, and to transmit signals, data, and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A device for performing an ophthalmic procedure in an eye, the device comprising:
    a hand-held portion;
    an elongate member extending from a distal end region of the hand-held portion, the elongate member comprising a lumen and an opening near a distal end region of the elongate member;
    an aspiration pump within the hand-held portion in fluid communication with the opening of the elongate member, wherein the aspiration pump comprises:
        a camshaft extending along a longitudinal axis and having a plurality of lobed cams;

tubing extending parallel to the longitudinal axis; and
a plurality of cam followers driven by the cams of the camshaft to move in a plane perpendicular to the longitudinal axis to sequentially compress the tubing; and
a drive mechanism configured to operatively couple with the camshaft, wherein the drive mechanism is configured to rotate the camshaft and drive oscillation of the elongate member.

2. The device of claim 1, wherein the tubing comprises a proximal flow path that splits into a pair of peripheral tubes positioned on either side of the camshaft, the pair of peripheral tubes combine distal to a pumping manifold to form a distal flow path in fluid communication with the lumen of the elongate member.

3. The device of claim 2, wherein the plurality of cam followers sequentially compressing the pair of peripheral tubes creates a substantially non-pulsatile aspiration.

4. The device of claim 3, wherein the substantially non-pulsatile aspiration is less than 3 cc/minute.

5. The device of claim 3, wherein the substantially non-pulsatile aspiration is between 3 cc/minute to 10 cc/minute.

6. The device of claim 3, wherein the substantially non-pulsatile aspiration is greater than 10 cc/minute up to 25 cc/minute.

7. The device of claim 1, wherein the elongate member is movable in a reciprocating motion relative to the hand-held portion.

8. The device of claim 1, wherein the elongate member is configured for lens fragmentation, lens emulsification, or anterior vitrectomy.

9. The device of claim 1, wherein the elongate member has a maximum cross-sectional diameter of about 1.25 mm.

10. The device of claim 1, wherein the elongate member has a maximum cross-sectional diameter that is no more than 3 mm.

11. The device of claim 1, wherein the elongate member is a vitrectomy probe that is between 20 gauge and 27 gauge.

12. The device of claim 1, wherein the elongate member is configured to slide reciprocally within an outer tube that is fixedly coupled within an interior of the hand-held portion.

13. The device of claim 12, wherein a distal tip of the elongate member forms a cutting edge.

14. The device of claim 13, wherein the outer tube comprises an opening through a side wall.

15. The device of claim 14, wherein the elongate member further comprises a side opening near its distal end region, wherein the elongate member is configured to create two cuts in concert with the outer tube, wherein a first cut of the two cuts is formed as a distal shaft edge of the elongate member advances distally through the outer tube and wherein a second cut of the two cuts is formed as a proximal shaft edge of the elongate member advances proximally through the outer tube.

16. The device of claim 1, wherein the elongate member comprises a proximal opening positioned within a chamber of a vacuum manifold in fluid communication with the aspiration pump.

17. The device of claim 1, wherein the elongate member is configured to oscillate at 300 cuts per minute.

18. The device of claim 1, wherein the elongate member is configured to oscillate at 500-600 cuts per minute.

19. The device of claim 1, wherein the elongate member is configured to oscillate up to 5000 cuts per minute.

20. The device of claim 1, wherein the elongate member is configured to oscillate up to 7500 cuts per minute.

21. The device of claim 1, further comprising a gear box configured to amplify an input from the aspiration pump to achieve an output of the elongate member configured for vitrectomy.

22. The device of claim 21, wherein the gear box is a planetary gear box.

23. The device of claim 1, further comprising gearing to ramp up input from the drive mechanism.

24. The device of claim 23, wherein the camshaft of the aspiration pump rotates at a fixed rate to deliver between about 15 cc/minute and 30 cc/minute of aspiration potential.

25. The device of claim 23, wherein the input from the drive mechanism is about 140 RPMs and the gearing has a ratio that is at least 3:1, 4:1, 5:1, 6:1, up to 30:1.

26. The device of claim 1, wherein the camshaft operatively interfaces with a cutter assembly configured to convert rotary motion of the camshaft with reciprocal linear motion of the elongate member.

27. The device of claim 26, wherein the cutter assembly comprises a ramp cam and a cutter return spring.

28. The device of claim 27, wherein proximal motion of the elongate member is a function of the ramp cam and distal motion of the elongate member is a function of the cutter return spring.

29. The device of claim 26, wherein the cutter assembly comprises a translating magnet disc and a rotating magnet disc.

30. The device of claim 29, wherein the translating magnet disc comprises one or more magnets and wherein the rotating magnet disc comprises one or more magnets.

31. The device of claim 30, wherein the one or more magnets of the translating magnet disc and the rotating magnet disc create a local magnetic field as the one or more magnets of the rotating magnet disc spin in and out of alignment with the one or more magnets of the translating magnet disc.

32. The device of claim 31, wherein the translating magnet disc is coupled to a cutter spline and the cutter spline is coupled to the elongate member such that the translating magnet disc, the cutter spline, and the elongate member all translate axially together.

33. The device of claim 32, wherein the translating magnet disc, cutter spline, and the elongate member are configured to move bidirectionally a distance axially along the longitudinal axis due to rotation of the camshaft.

34. The device of claim 30, wherein alignment of the one or more magnets of the rotating magnet disc with the one or more magnets of the translating magnet disc cause linear motion by magnetic attraction or magnetic repulsion.

35. The device of claim 30, wherein the rotating magnet disc comprises a plurality of magnets oriented relative to one another so that poles of the magnets alternate.

36. The device of claim 30, wherein rotation of the rotating magnet disc relative to the translating magnet disc causes the poles of the plurality of magnets to cause alternating repulsion and attraction with the one or more magnets of the translation magnet disc causing oscillation of the elongate member.

37. The device of claim 30, further comprising a second rotating magnet disc comprising one or more magnets, wherein the second rotating magnet disc is positioned distal to the translating magnet disc.

38. The device of claim 37, wherein alignment of the one or more magnets of the first and second rotating magnet discs with the one or more magnets of the translating magnet disc cause oscillation of the cutting tube.

39. The device of claim 38, wherein the one or more magnets of the second rotating magnet disc have poles arranged to cause repulsion of the one or more magnets of the translating magnet disc with the one or more magnets of the first rotating magnet disc have poles arranged to cause attraction, the repulsion and attraction creating a stronger magnetic field to urge the translating magnet disc to move linearly between the first and second rotating magnet discs.

40. The device of claim 39, wherein the second rotating magnet disc forms a distal hard stop and the first rotating magnet disc forms a proximal hard stop for the translating magnet disc.

41. The device of claim 26, further comprising a cutter switch configured to physically decouple rotation of the camshaft from oscillation of the elongate member.

42. The device of claim 41, wherein the cutter switch controls whether the elongate member oscillates upon activation of an input on the hand held portion.

43. The device of claim 41, wherein the cutter switch locks out oscillation of the elongate member during rotation of the cutter assembly.

44. The device of claim 1, further comprising a bleed valve functionally coupled to an input of the hand-held portion, the bleed valve configured to modulate effective flow rate of the aspiration pump through the lumen of the elongate member.

45. The device of claim 44, wherein the input is a trigger configured to be pressed.

46. The device of claim 45, wherein an open configuration of the bleed valve siphons substantially all aspiration generated by the aspiration pump away from the lumen of the elongate member.

47. The device of claim 45, wherein a closed configuration of the bleed valve directs full aspiration generated by the aspiration pump through the lumen of the elongate member.

48. The device of claim 45, wherein the bleed valve is a needle valve having an axially-aligned helical cam-driven needle movable relative to a valve seat in a fluidic channel.

49. The device of claim 48, wherein an open configuration of the needle valve connects the aspiration pump to an irrigation fluid line resulting in minimal aspiration through the lumen of the elongate member.

50. The device of claim 49, wherein a first amount of travel of the trigger away from a resting state activates the aspiration pump, wherein the needle valve remains open so that aspiration from the aspiration pump is not delivered through the lumen of the cutting tube.

51. The device of claim 50, wherein a second further amount of travel of the trigger away from the resting state urges the needle toward the valve seat.

52. The device of claim 50, wherein the first amount of travel is greater than zero and less than 20% of a trigger stroke.

53. The device of claim 51, wherein the second further amount of travel is at least 20% of a trigger stroke.

54. The device of claim 1, further comprising a drive mechanism configured to drive reciprocating motion of the elongate member and generate vacuum via the aspiration pump, wherein the reciprocating motion and vacuum are generated independently by the drive mechanism.

55. The device of claim 54, wherein the drive mechanism comprises at least a first motor and concentric drive shafts.

56. The device of claim 55, wherein the concentric drive shafts comprise an outer drive shaft operatively coupled to the aspiration pump and an inner drive shaft extending coaxially through the outer drive shaft and operatively coupled to the elongate member.

57. The device of claim 56, wherein the outer drive shaft and the inner drive shaft each terminates in a hex head.

58. The device of claim 57, wherein the drive mechanism further comprises a differential gear train or a planetary gear train.

59. A device for performing an ophthalmic procedure in an eye, the device comprising:
a hand-held portion;
an elongate member extending from a distal end region of the hand-held portion and configured to oscillate, the elongate member comprising a lumen and an opening near a distal end region of the elongate member;
an aspiration pump within the hand-held portion in fluid communication with the opening of the elongate member, wherein the aspiration pump comprises:
a camshaft extending along a longitudinal axis and having a plurality of lobed cams;
tubing extending parallel to the longitudinal axis; and
a plurality of cam followers driven by the cams of the camshaft to move in a plane perpendicular to the longitudinal axis to sequentially compress the tubing; and
a cutter switch configured to physically decouple rotation of the camshaft from oscillation of the elongate member.

60. The device of claim 59, wherein the cutter switch controls whether the elongate member oscillates upon activation of an input on the hand held portion.

61. The device of claim 59, further comprising a drive mechanism configured to operatively couple with the camshaft, wherein the drive mechanism is configured to rotate the camshaft and drive oscillation of the elongate member.

62. The device of claim 61, wherein the camshaft operatively interfaces with a cutter assembly configured to convert rotary motion of the camshaft with reciprocal linear motion of the elongate member.

63. The device of claim 62, wherein the cutter assembly comprises a ramp cam and a cutter return spring.

64. The device of claim 63, wherein proximal motion of the elongate member is a function of the ramp cam and distal motion of the elongate member is a function of the cutter return spring.

65. The device of claim 62, wherein the cutter switch locks out oscillation of the elongate member during rotation of the cutter assembly.

66. The device of claim 59, further comprising a bleed valve functionally coupled to an input of the hand-held portion, the bleed valve configured to modulate effective flow rate of the aspiration pump through the lumen of the elongate member.

67. The device of claim 66, wherein the input is a trigger configured to be pressed.

68. The device of claim 67, wherein an open configuration of the bleed valve siphons substantially all aspiration generated by the aspiration pump away from the lumen of the elongate member.

69. The device of claim 67, wherein a closed configuration of the bleed valve directs full aspiration generated by the aspiration pump through the lumen of the elongate member.

70. The device of claim 67, wherein the bleed valve is a needle valve having an axially-aligned helical cam-driven needle movable relative to a valve seat in a fluidic channel.

71. The device of claim 70, wherein an open configuration of the needle valve connects the aspiration pump to an irrigation fluid line resulting in minimal aspiration through the lumen of the elongate member.

72. The device of claim 71, wherein a first amount of travel of the trigger away from a resting state activates the aspiration pump, wherein the needle valve remains open so that aspiration from the aspiration pump is not delivered through the lumen of the cutting tube.

73. The device of claim 72, wherein a second further amount of travel of the trigger away from the resting state urges the needle toward the valve seat.

74. The device of claim 73, wherein the second further amount of travel is at least 20% of a trigger stroke.

75. The device of claim 72, wherein the first amount of travel is greater than zero and less than 20% of a trigger stroke.

76. The device of claim 59, wherein the tubing comprises a proximal flow path that splits into a pair of peripheral tubes positioned on either side of the camshaft, the pair of peripheral tubes combine distal to a pumping manifold to form a distal flow path in fluid communication with the lumen of the elongate member.

77. The device of claim 76, wherein the plurality of cam followers sequentially compressing the pair of peripheral tubes creates a substantially non-pulsatile aspiration.

78. The device of claim 59, wherein the elongate member is configured for lens fragmentation, lens emulsification, or anterior vitrectomy.

79. The device of claim 59, wherein the elongate member is configured to slide reciprocally within an outer tube that is fixedly coupled within an interior of the hand-held portion.

80. The device of claim 79, wherein a distal tip of the elongate member forms a cutting edge.

81. The device of claim 80, wherein the outer tube comprises an opening through a side wall.

82. The device of claim 81, wherein the elongate member further comprises a side opening near its distal end region, wherein the elongate member is configured to create two cuts in concert with the outer tube, wherein a first cut of the two cuts is formed as a distal shaft edge of the elongate member advances distally through the outer tube and wherein a second cut of the two cuts is formed as a proximal shaft edge of the elongate member advances proximally through the outer tube.

83. The device of claim 59, wherein the elongate member comprises a proximal opening positioned within a chamber of a vacuum manifold in fluid communication with the aspiration pump.

84. A device for performing an ophthalmic procedure in an eye, the device comprising:
  a hand-held portion;
  an elongate member extending from a distal end region of the hand-held portion, the elongate member comprising a lumen and an opening near a distal end region of the elongate member;
  an aspiration pump within the hand-held portion in fluid communication with the opening of the elongate member, wherein the aspiration pump comprises:
    a camshaft extending along a longitudinal axis and having a plurality of lobed cams;
    tubing extending parallel to the longitudinal axis; and
    a plurality of cam followers driven by the cams of the camshaft to move in a plane perpendicular to the longitudinal axis to sequentially compress the tubing; and
  a drive mechanism configured to drive reciprocating motion of the elongate member and to generate vacuum via the aspiration pump, wherein the reciprocating motion and vacuum are generated independently by the drive mechanism.

85. The device of claim 84, wherein the drive mechanism comprises at least a first motor and concentric drive shafts.

86. The device of claim 85, wherein the concentric drive shafts comprise an outer drive shaft operatively coupled to the aspiration pump and an inner drive shaft extending coaxially through the outer drive shaft and operatively coupled to the elongate member.

87. The device of claim 86, wherein the outer drive shaft and the inner drive shaft each terminates in a hex head.

88. The device of claim 87, wherein the drive mechanism further comprises a differential gear train or a planetary gear train.

* * * * *